United States Patent
Li et al.

(10) Patent No.: US 12,194,106 B2
(45) Date of Patent: Jan. 14, 2025

(54) ANTIBODIES TARGETING LIV-1 AND USES THEREOF

(71) Applicant: LANOVA MEDICINES LIMITED, Shanghai (CN)

(72) Inventors: Runsheng Li, Shanghai (CN); Wentao Huang, Shanghai (CN); Ying Qin Zang, Shanghai (CN); Zhifang Liu, Shanghai (CN); Yifan Li, Shanghai (CN)

(73) Assignee: LANOVA MEDICINES LIMITED, Shanghai (CN)

(*) Notice: Subject to any disclaimer, the term of this patent is extended or adjusted under 35 U.S.C. 154(b) by 0 days.

(21) Appl. No.: 18/656,166

(22) Filed: May 6, 2024

(65) Prior Publication Data

US 2024/0325555 A1    Oct. 3, 2024

Related U.S. Application Data

(63) Continuation of application No. PCT/CN2024/076796, filed on Feb. 7, 2024.

(30) Foreign Application Priority Data

Feb. 7, 2023   (WO) ................ PCT/CN2023/074833

(51) Int. Cl.
*A61K 47/68* (2017.01)
*A61P 35/00* (2006.01)
*C07K 16/28* (2006.01)

(52) U.S. Cl.
CPC .. *A61K 47/68031* (2023.08); *A61K 47/68033* (2023.08); *A61K 47/68037* (2023.08); *A61K 47/6849* (2017.08); *A61K 47/6855* (2017.08); *A61P 35/00* (2018.01); *C07K 16/2857* (2013.01); *C07K 2317/54* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| | | |
|---|---|---|
| 2013/0259860 A1 | 10/2013 | Smith et al. |
| 2020/0231699 A1 | 7/2020 | Terrett et al. |
| 2020/0283540 A1 | 9/2020 | Kennedy et al. |
| 2021/0030885 A1 | 2/2021 | Stevens et al. |
| 2022/0112274 A1 | 4/2022 | Onsum et al. |

FOREIGN PATENT DOCUMENTS

| | | |
|---|---|---|
| CN | 103533957 A | 1/2014 |
| CN | 111757892 A | 10/2020 |
| CN | 113015750 A | 6/2021 |
| CN | 114423464 A | 4/2022 |

(Continued)

OTHER PUBLICATIONS

International Search Report for PCT International Application No. PCT/CN2024/076796, dated May 16, 2024, 9 pages.

(Continued)

*Primary Examiner* — Karl J Puttlitz
(74) *Attorney, Agent, or Firm* — Sheppard, Mullin, Richter & Hampton LLP

(57) ABSTRACT

Provided are antibodies and fragments thereof having binding specificity to the liver receptor homolog 1 (LIV-1. SLC39A6 or ZIP6) protein as well as their derivatives and uses.

20 Claims, 17 Drawing Sheets
Specification includes a Sequence Listing.

(56) References Cited

FOREIGN PATENT DOCUMENTS

WO   2021016233 A1   1/2021
WO   2022067348 A1   3/2022

OTHER PUBLICATIONS

Written Opinion of the International Searching Authority for PCT International Application No. PCT/CN2024/076796, dated May 16, 2024, 5 pages.
Sussman, D. et al. "SGN-LIV1A: A Novel Antibody-Drug Conjugate Targeting LIV-1 for the Treatment of Metastatic Breast Cancer", Molecular Cancer Therapeutics, vol. 13, No. 12, Dec. 31, 2014 (Dec. 31, 2014), pp. 2991-3000.

ANTIBODIES TARGETING LIV-1 AND USES THEREOF

CROSS REFERENCE TO RELATED APPLICATIONS

The present application is a continuation of International Application No. PCT/CN2024/076796, filed Feb. 7, 2024, which claims priority to International Application No. PCT/CN2023/074833, filed Feb. 7, 2023, the content of each of which is incorporated herein by reference in its entirety in the present disclosure.

REFERENCE TO AN ELECTRONIC SEQUENCE LISTING

The contents of the electronic sequence listing (366242.xml; Size: 228,090 bytes; and Date of Creation: Feb. 7, 2024) is herein incorporated by reference in its entirety.

BACKGROUND

"Liver receptor homolog 1" (LIV-1), also known as "solute carrier family 39 member 6" (SLC39A6), or "zinc transporter ZIP6," is involved in the transport of metal ions such as zinc into cells. LIV-1 has been shown to be involved in regulating cellular processes such as cell growth, survival, and migration. It is expressed in a variety of tissues, including the liver, mammary glands, and prostate.

LIV-1 acts as a transcriptional co-activator, binding to specific target genes and regulating their expression, and it has been shown to play a role in promoting cell division, protecting cancer cells from programmed cell death, regulating cell migration, and modulating gene expression. LIV-1 has been shown to be expressed in estrogen receptor-positive breast cancers and prostate cancers.

LIV-1 is a promising target for the development of cancer treatments. Antibodies against LIV-1 with improved therapeutic efficacy, safety and developability are needed.

SUMMARY

New and improved antibodies targeting LIV-1 are disclosed herein, which exhibited comparable affinity to the LIV-1 protein to benchmark anti-LIV-1 antibodies. Also, as demonstrated in the experimental examples, the instant antibodies, in particular their humanized counterparts, are suitable for development as antibody-drug conjugates.

According, one embodiment of the present disclosure provides an antibody or antigen-binding fragment thereof that has binding specificity to the human liver receptor homolog 1 (LIV-1) protein, wherein the antibody or the fragment thereof comprises a heavy chain variable region (VH) comprising heavy chain complementarity determining regions (CDR) VH CDR1, VH CDR2, and VH CDR3, and a light chain variable region (VL) comprising VL CDR1, VL CDR2, and VL CDR3, and wherein the VH CDR1, VH CDR2, VH CDR3, VL CDR1, VL CDR2, and VL CDR3, respectively, comprise: (a) the amino acid sequences of SEQ ID NO:57-62; (b) the amino acid sequences of SEQ ID NO:165, 233, 167, 234, 169 and 170; (c) the amino acid sequences of SEQ ID NO: 165-170; (d) the amino acid sequences of SEQ ID NO:213, 243, 215, 216, 217 and 218; or (e) the amino acid sequences of SEQ ID NO:213-218.

In some embodiments, the VH CDR1 comprises the amino acid sequence of SEQ ID NO: 57, the VH CDR2 comprises the amino acid sequence of SEQ ID NO:58, the VH CDR3 comprises the amino acid sequence of SEQ ID NO:59, the VL CDR1 comprises the amino acid sequence of SEQ ID NO:60, the VL CDR2 comprises the amino acid sequence of SEQ ID NO: 61, and the VL CDR3 comprises the amino acid sequence of SEQ ID NO:62. In some embodiments, the VH comprises the amino acid sequence of SEQ ID NO: 1, 225, 226, 227, 228 or 229, and the VL comprises the amino acid sequence of SEQ ID NO:2, 230, 231, or 232. In some embodiments, the VH comprises the amino acid sequence of SEQ ID NO:227, and the VL comprises the amino acid sequence of SEQ ID NO:230.

In some embodiments, the VH CDR1 comprises the amino acid sequence of SEQ ID NO: 165, the VH CDR2 comprises the amino acid sequence of SEQ ID NO:233, the VH CDR3 comprises the amino acid sequence of SEQ ID NO:167, the VL CDR1 comprises the amino acid sequence of SEQ ID NO:234, the VL CDR2 comprises the amino acid sequence of SEQ ID NO: 169, and the VL CDR3 comprises the amino acid sequence of SEQ ID NO: 170. In some embodiments, the VH comprises the amino acid sequence of SEQ ID NO:235, 236 or 237, and the VL comprises the amino acid sequence of SEQ ID NO:238, 239, 240, 241 or 242. In some embodiments, the VH comprises the amino acid sequence of SEQ ID NO:235, and the VL comprises the amino acid sequence of SEQ ID NO:238.

In some embodiments, the VH CDR1, VH CDR2, VH CDR3, VL CDR1, VL CDR2, and VL CDR3, respective, comprise the amino acid sequences of SEQ ID NO:165-170. In some embodiments, the VH comprises the amino acid sequence of SEQ ID NO:37, and the VL comprises the amino acid sequence of SEQ ID NO:38.

In some embodiments, the VH CDR1 comprises the amino acid sequence of SEQ ID NO: 213, the VH CDR2 comprises the amino acid sequence of SEQ ID NO:243, the VH CDR3 comprises the amino acid sequence of SEQ ID NO:215, the VL CDR1 comprises the amino acid sequence of SEQ ID NO:216, the VL CDR2 comprises the amino acid sequence of SEQ ID NO: 217, and the VL CDR3 comprises the amino acid sequence of SEQ ID NO:218. In some embodiments, the VH comprises the amino acid sequence of SEQ ID NO:244, 245, 246, 247, 248, or 249, and the VL comprises the amino acid sequence of SEQ ID NO:250, 251 or 252. In some embodiments, the VH comprises the amino acid sequence of SEQ ID NO:244, and the VL comprises the amino acid sequence of SEQ ID NO:251.

In some embodiments, the VH CDR1, VH CDR2, VH CDR3, VL CDR1, VL CDR2, and VL CDR3, respective, comprise the amino acid sequences of SEQ ID NO: 213-218. In some embodiments, the VH comprises the amino acid sequence of SEQ ID NO:53, and the VL comprises the amino acid sequence of SEQ ID NO:54.

Also provided, in one embodiment, is a multispecific antibody comprising an antigen-binding fragment of the present disclosure and one or more antibody or antigen-binding fragment having binding specificity to a target antigen that is not LIV-1.

Also provided is a chimeric antigen receptor (CAR) comprising an antigen-binding fragment of the present disclosure, a transmembrane domain, a costimulatory domain, and a CD3ξ intracellular domain.

In yet another embodiment, the present disclosure provides an antibody-drug conjugate comprising a drug moiety conjugated to the antibody or antigen-binding fragment thereof of the present disclosure. In some embodiments, the drug moiety is a cytotoxic or cytostatic agent. In some embodiments, the drug moiety is a maytansinoid, an auristatin, or a macrocyclic ketone analogue. In some embodiments, the drug moiety comprises eribulin. In some embodiments, the drug moiety comprises monomethyl auristatin E (MMAE) or monomethyl auristatin F (MMAF). In some embodiments, the drug moiety is attached to the antibody or fragment thereof through a linker. In some embodiments, the linker is hydrolyzable under acidic conditions.

In some embodiments, the drug moiety comprises exatecan or DXd (exatecan derivative for ADC). In some embodiments, the drug moiety is attached to the antibody or fragment thereof through a linker. In some embodiments, the drug moiety and the linker are selected from the group consisting of:

FIG. 3 shows the internalization effect of the tested chimeric antibodies.

FIG. 4 shows the measured cytotoxic activities of the tested chimeric antibodies.

FIG. 5A-D show the FACS binding of the humanized antibodies to human and cynomolgus LIV-1.

FIG. 6 shows cross-reactivity of the humanized antibodies.

FIG. 7 shows the internalization effect of the humanized antibodies.

FIG. 8 shows FACS binding of the humanized antibodies and their antibody-drug conjugates to LIV-1 overexpression human cells.

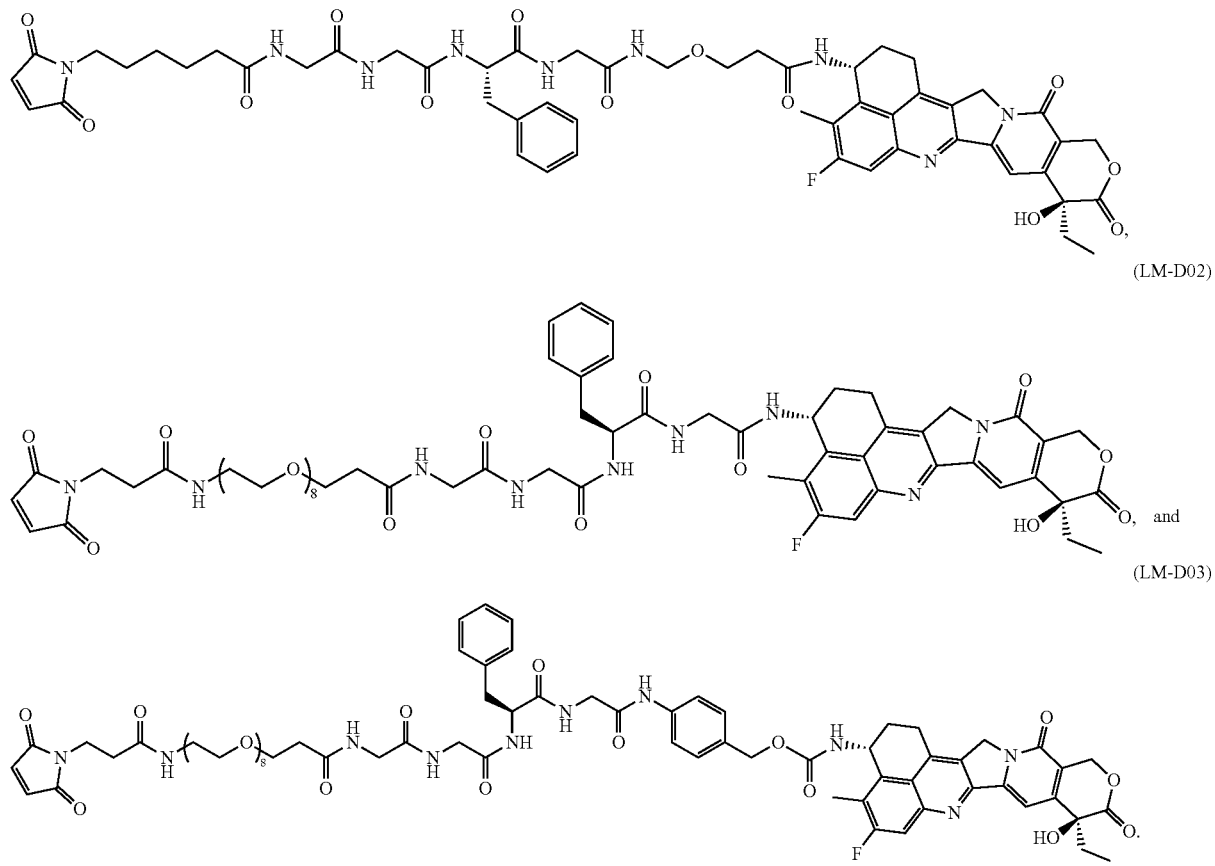

Methods and uses for treating diseases and conditions such as cancer are also provided. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

DETAILED DESCRIPTION

Definitions

Figure 1A:
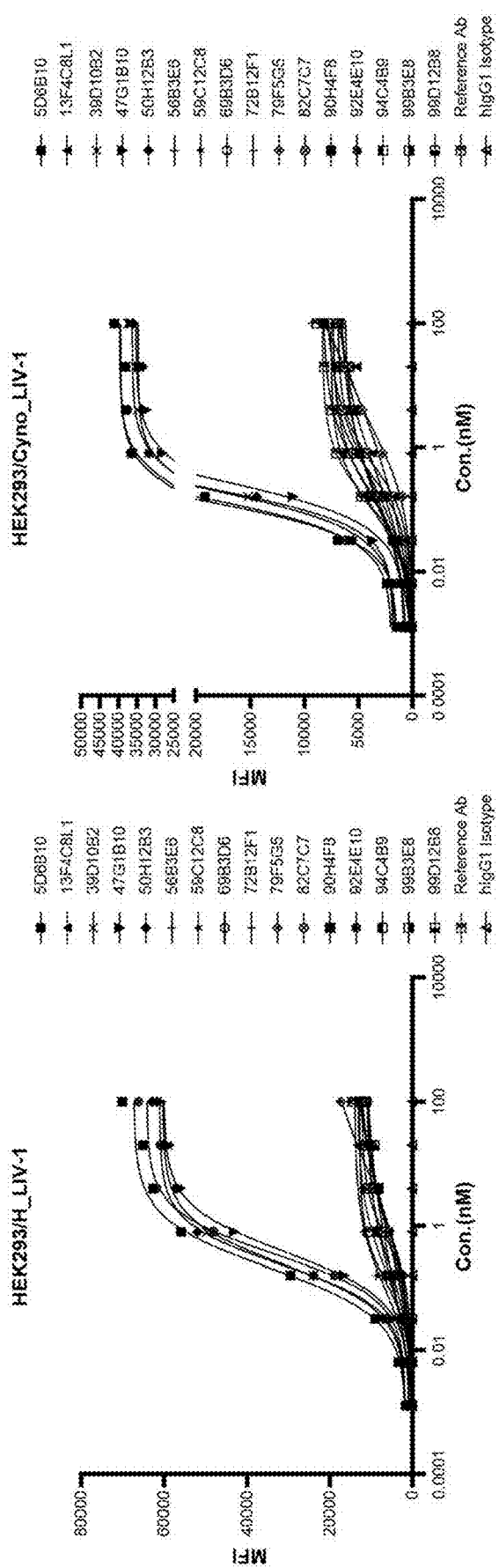
FIG. 1A-C show the results of FACS binding of the tested chimeric antibodies to human LIV-1 and cynomolgus LIV-1.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, u, a, δ, €) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-LIV-1 Antibodies and Fragments

The present disclosure provides anti-LIV-1 antibodies with high affinity and improved internalization inducing and cytotoxic activities. Twenty-eight new murine anti-LIV-1 antibodies were obtained, including 5D6B10, 13F4C8, 39D10B2, 47G1B10, 50H12B3, 56B3E6, 59C12C8, 69B3D6, 72B12F1, 79F5G5, 82C7C7, 90H4F8, 92E4E10, 94C4B9, 99B3E8, 99D12B8, 109C9D4, 112H11C12, 124H4D11, 127A2B9, 136F3D10C10, 135C6E7, 108H1D4, 248H1G3, 282G5A2, 286B5E6, 290F10G10, and 293F10B6.

Most of these antibodies exhibited excellent binding affinity to the LIV-1 protein. Three of them, 5D6B10, 124H4D11 and 290F10G10, were humanized and engaged in additional testing. These humanized antibodies, as well as their antibody-drug conjugates, demonstrated excellent therapeutic profiles, and some have outperformed the benchmark antibody.

In accordance with one embodiment of the present disclosure, provided is an antibody or fragment thereof that includes the heavy chain and light chain variable domains with the CDR regions of any one of antibodies 5D6B10, 13F4C8, 39D10B2, 47G1B10, 50H12B3, 56B3E6, 59C12C8, 69B3D6, 72B12F1, 79F5G5, 82C7C7, 90H4F8, 92E4E10, 94C4B9, 99B3E8, 99D12B8, 109C9D4, 112H11C12, 124H4D11, 127A2B9, 136F3D10C10, 135C6E7, 108H1D4, 248H1G3, 282G5A2, 286B5E6, 290F10G10, and 293F10B6.

Sequence analysis revealed that some of the CDRs can potentially be modified post-translationally. To avoid post-translational modification (PTM) risks and thus simplify manufacturing, the instant disclosure designed and tested certain de-risked versions of the CDRs. In some embodiments, the CDR region may be modified to remove residues that can be potentially subject to PTM. Example CDR sequences are provided in Table 1B and Tables 6B, 7B and 8B.

In some embodiments, provided is an antibody or antigen-binding fragment that is derived from antibody 5D6B10. In some embodiments, the VH CDR1 includes the amino acid sequence of SEQ ID NO: 57; the VH CDR2 includes the amino acid sequence of SEQ ID NO: 58; the VH CDR3 includes the amino acid sequence of SEQ ID NO: 59; the VL CDR1 includes the amino acid sequence of SEQ ID NO: 60; the VL CDR2 includes the amino acid sequence of SEQ ID NO: 61; and the VL CDR3 includes an amino acid sequence selected from the group consisting SEQ ID NO: 62.

An example chimeric VH sequence includes the amino acid sequence of SEQ ID NO: 1. An example chimeric VL sequence includes the amino acid sequence of SEQ ID NO: 2. In some embodiments, the VH includes the amino acid sequence of SEQ ID NO: 1 or a sequence having at least 75%, 80%, 85%, 90%, 95% or 99% sequence identity to SEQ ID NO: 1, while retaining the corresponding VH CDRs. In some embodiments, the VL includes the amino acid sequence of SEQ ID NO: 2 or a sequence having at least 75%, 80%, 85%, 90%, 95% or 99% sequence identity to SEQ ID NO: 2, while retaining the corresponding VL CDRs.

An example humanized VH sequence includes an amino acid sequence selected from the group consisting of SEQ ID NO: 225-229. An example humanized VL sequence includes an amino acid sequence selected from the group consisting of SEQ ID NO: 230-232.

In some embodiments, the VH includes an amino acid sequence of any one of SEQ ID NO: 225-229, or a sequence having at least 75%, 80%, 85%, 90%, 95% or 99% sequence identity to any one of SEQ ID NO: 225-229, while retaining the corresponding VH CDRs. In some embodiments, the VL includes an amino acid sequence of any one of SEQ ID NO: 230-232, or a sequence having at least 75%, 80%, 85%, 90%, 95% or 99% sequence identity to any one of SEQ ID NO: 230-232, while retaining the corresponding VL CDRs.

In one embodiment, the VH includes the amino acid sequence of SEQ ID NO:227 and the VL includes the amino acid sequence of SEQ ID NO:230. In one embodiment, the VH includes the amino acid sequence of SEQ ID NO:227 and the VL includes the amino acid sequence of SEQ ID NO:231. In one embodiment, the VH includes the amino acid sequence of SEQ ID NO:227 and the VL includes the amino acid sequence of SEQ ID NO:232.

In one embodiment, the VH includes the amino acid sequence of SEQ ID NO:225 and the VL includes the amino acid sequence of SEQ ID NO:230. In one embodiment, the VH includes the amino acid sequence of SEQ ID NO:225 and the VL includes the amino acid sequence of SEQ ID NO:231. In one embodiment, the VH includes the amino acid sequence of SEQ ID NO:225 and the VL includes the amino acid sequence of SEQ ID NO:232.

In one embodiment, the VH includes the amino acid sequence of SEQ ID NO:226 and the VL includes the amino acid sequence of SEQ ID NO:230. In one embodiment, the VH includes the amino acid sequence of SEQ ID NO:226 and the VL includes the amino acid sequence of SEQ ID NO:231. In one embodiment, the VH includes the amino acid sequence of SEQ ID NO:226 and the VL includes the amino acid sequence of SEQ ID NO:232.

In one embodiment, the VH includes the amino acid sequence of SEQ ID NO:228 and the VL includes the amino acid sequence of SEQ ID NO:230. In one embodiment, the VH includes the amino acid sequence of SEQ ID NO:228 and the VL includes the amino acid sequence of SEQ ID NO:231. In one embodiment, the VH includes the amino acid sequence of SEQ ID NO:228 and the VL includes the amino acid sequence of SEQ ID NO:232.

In one embodiment, the VH includes the amino acid sequence of SEQ ID NO:229 and the VL includes the amino acid sequence of SEQ ID NO:230. In one embodiment, the VH includes the amino acid sequence of SEQ ID NO:229 and the VL includes the amino acid sequence of SEQ ID NO:231. In one embodiment, the VH includes the amino acid sequence of SEQ ID NO:229 and the VL includes the amino acid sequence of SEQ ID NO:232.

Also provided, in some embodiments, are antibodies and antigen-binding fragments therefore that bind to the same epitope on LIV-1 as 5D6B10. Also provided, in some embodiments, are antibodies and antigen-binding fragments therefore that competes with 5D6B10 in binding to LIV-1.

In some embodiments, provided is an antibody or antigen-binding fragment that is derived from antibody 124H4D11. In some embodiments, the VH CDR1 includes the amino acid sequence of SEQ ID NO: 165; the VH CDR2 includes the amino acid sequence of SEQ ID NO: 166; the VH CDR3 includes the amino acid sequence of SEQ ID NO: 167; the VL CDR1 includes the amino acid sequence of SEQ ID NO: 168; the VL CDR2 includes the amino acid sequence of SEQ ID NO: 169; and the VL CDR3 includes an amino acid sequence selected from the group consisting SEQ ID NO: 170.

An example VH sequence includes the amino acid sequence of SEQ ID NO: 37. An example VL sequence includes the amino acid sequence of SEQ ID NO: 38. In some embodiments, the VH includes the amino acid sequence of SEQ ID NO: 37 or a sequence having at least 75%, 80%, 85%, 90%, 95% or 99% sequence identity to SEQ ID NO: 37, while retaining the corresponding VH CDRs. In some embodiments, the VL includes the amino acid sequence of SEQ ID NO: 38 or a sequence having at least 75%, 80%, 85%, 90%, 95% or 99% sequence identity to SEQ ID NO: 38, while retaining the corresponding VL CDRs.

In some embodiments, the VH CDR2 is PTM de-risked in which the potential PTM site NG is mutated to ND. In some embodiments, the VL CDR1 is PTM de-risked in which the potential PTM site NG is mutated to NA.

In some embodiments, the VH CDR1 includes the amino acid sequence of SEQ ID NO: 165; the VH CDR2 includes the amino acid sequence of SEQ ID NO: 233; the VH CDR3 includes the amino acid sequence of SEQ ID NO: 167; the VL CDR1 includes the amino acid sequence of SEQ ID NO: 234; the VL CDR2 includes the amino acid sequence of SEQ ID NO: 169; and the VL CDR3 includes an amino acid sequence selected from the group consisting SEQ ID NO: 170.

In some embodiments, the VH CDR1 includes the amino acid sequence of SEQ ID NO: 165; the VH CDR2 includes the amino acid sequence of SEQ ID NO: 233; the VH CDR3 includes the amino acid sequence of SEQ ID NO: 167; the VL CDR1 includes the amino acid sequence of SEQ ID NO: 168; the VL CDR2 includes the amino acid sequence of SEQ ID NO: 169; and the VL CDR3 includes an amino acid sequence selected from the group consisting SEQ ID NO: 170.

In some embodiments, the VH CDR1 includes the amino acid sequence of SEQ ID NO: 165; the VH CDR2 includes the amino acid sequence of SEQ ID NO: 166; the VH CDR3 includes the amino acid sequence of SEQ ID NO: 167; the VL CDR1 includes the amino acid sequence of SEQ ID NO: 234; the VL CDR2 includes the amino acid sequence of SEQ ID NO: 169; and the VL CDR3 includes an amino acid sequence selected from the group consisting SEQ ID NO: 170.

An example humanized VH sequence includes an amino acid sequence selected from the group consisting of SEQ ID NO: 235-237. An example humanized VL sequence includes an amino acid sequence selected from the group consisting of SEQ ID NO: 238-242.

In some embodiments, the VH includes an amino acid sequence of any one of SEQ ID NO: 235-237, or a sequence having at least 75%, 80%, 85%, 90%, 95% or 99% sequence identity to any one of SEQ ID NO: 235-237, while retaining the corresponding VH CDRs. In some embodiments, the VL includes an amino acid sequence of any one of SEQ ID NO: 238-242, or a sequence having at least 75%, 80%, 85%, 90%, 95% or 99% sequence identity to any one of SEQ ID NO: 238-242, while retaining the corresponding VL CDRs.

In one embodiment, the VH includes the amino acid sequence of SEQ ID NO:235 and the VL includes the amino acid sequence of SEQ ID NO:238. In one embodiment, the VH includes the amino acid sequence of SEQ ID NO:235 and the VL includes the amino acid sequence of SEQ ID NO:239. In one embodiment, the VH includes the amino acid sequence of SEQ ID NO:235 and the VL includes the amino acid sequence of SEQ ID NO:240. In one embodiment, the VH includes the amino acid sequence of SEQ ID NO:235 and the VL includes the amino acid sequence of SEQ ID NO:241. In one embodiment, the VH includes the amino acid sequence of SEQ ID NO:235 and the VL includes the amino acid sequence of SEQ ID NO: 242.

In one embodiment, the VH includes the amino acid sequence of SEQ ID NO:236 and the VL includes the amino acid sequence of SEQ ID NO:238. In one embodiment, the VH includes the amino acid sequence of SEQ ID NO:236 and the VL includes the amino acid sequence of SEQ ID NO:239. In one embodiment, the VH includes the amino acid sequence of SEQ ID NO:236 and the VL includes the amino acid sequence of SEQ ID NO:240. In one embodiment, the VH includes the amino acid sequence of SEQ ID NO:236 and the VL includes the amino acid sequence of SEQ ID NO:241. In one embodiment, the VH includes the amino acid sequence of SEQ ID NO:236 and the VL includes the amino acid sequence of SEQ ID NO: 242.

In one embodiment, the VH includes the amino acid sequence of SEQ ID NO:237 and the VL includes the amino acid sequence of SEQ ID NO:238. In one embodiment, the VH includes the amino acid sequence of SEQ ID NO:237 and the VL includes the amino acid sequence of SEQ ID NO:239. In one embodiment, the VH includes the amino acid sequence of SEQ ID NO:237 and the VL includes the amino acid sequence of SEQ ID NO:240. In one embodiment, the VH includes the amino acid sequence of SEQ ID NO:237 and the VL includes the amino acid sequence of SEQ ID NO:241. In one embodiment, the VH includes the amino acid sequence of SEQ ID NO:237 and the VL includes the amino acid sequence of SEQ ID NO: 242.

Also provided, in some embodiments, are antibodies and antigen-binding fragments therefore that bind to the same epitope on LIV-1 as 124H4D11. Also provided, in some embodiments, are antibodies and antigen-binding fragments therefore that competes with 124H4D11 in binding to LIV-1.

In some embodiments, provided is an antibody or antigen-binding fragment that is derived from antibody 290F10G10. In some embodiments, the VH CDR1 includes the amino acid sequence of SEQ ID NO: 213; the VH CDR2 includes the amino acid sequence of SEQ ID NO: 214; the VH CDR3 includes the amino acid sequence of SEQ ID NO: 215; the VL CDR1 includes the amino acid sequence of SEQ ID NO: 216; the VL CDR2 includes the amino acid sequence of SEQ ID NO: 217; and the VL CDR3 includes an amino acid sequence selected from the group consisting SEQ ID NO: 218.

An example VH sequence includes the amino acid sequence of SEQ ID NO: 53. An example VL sequence includes the amino acid sequence of SEQ ID NO: 54. In some embodiments, the VH includes the amino acid sequence of SEQ ID NO: 53 or a sequence having at least 75%, 80%, 85%, 90%, 95% or 99% sequence identity to SEQ ID NO: 53, while retaining the corresponding VH CDRs. In some embodiments, the VL includes the amino acid sequence of SEQ ID NO: 54 or a sequence having at least 75%, 80%, 85%, 90%, 95% or 99% sequence identity to SEQ ID NO: 54, while retaining the corresponding VL CDRs.

In some embodiments, the VH CDR2 is PTM de-risked in which the potential PTM site NG is mutated to NA. In some embodiments, the VH CDR1 includes the amino acid sequence of SEQ ID NO: 213; the VH CDR2 includes the amino acid sequence of SEQ ID NO: 243; the VH CDR3 includes the amino acid sequence of SEQ ID NO: 215; the VL CDR1 includes the amino acid sequence of SEQ ID NO: 216; the VL CDR2 includes the amino acid sequence of SEQ ID NO: 217; and the VL CDR3 includes an amino acid sequence selected from the group consisting SEQ ID NO: 218.

An example humanized VH sequence includes an amino acid sequence selected from the group consisting of SEQ ID NO: 244-249. An example humanized VL sequence includes an amino acid sequence selected from the group consisting of SEQ ID NO: 250-252.

In some embodiments, the VH includes an amino acid sequence of any one of SEQ ID NO: 244-249, or a sequence having at least 75%, 80%, 85%, 90%, 95% or 99% sequence identity to any one of SEQ ID NO: 244-249, while retaining the corresponding VH CDRs. In some embodiments, the VL includes an amino acid sequence of any one of SEQ ID NO: 250-252, or a sequence having at least 75%, 80%, 85%, 90%, 95% or 99% sequence identity to any one of SEQ ID NO: 250-252, while retaining the corresponding VL CDRs.

In one embodiment, the VH includes the amino acid sequence of SEQ ID NO:244 and the VL includes the amino acid sequence of SEQ ID NO:251. In one embodiment, the VH includes the amino acid sequence of SEQ ID NO:244 and the VL includes the amino acid sequence of SEQ ID NO:250. In one embodiment, the VH includes the amino acid sequence of SEQ ID NO:244 and the VL includes the amino acid sequence of SEQ ID NO:252.

In one embodiment, the VH includes the amino acid sequence of SEQ ID NO:245 and the VL includes the amino acid sequence of SEQ ID NO:251. In one embodiment, the VH includes the amino acid sequence of SEQ ID NO:245 and the VL includes the amino acid sequence of SEQ ID NO:250. In one embodiment, the VH includes the amino acid sequence of SEQ ID NO:245 and the VL includes the amino acid sequence of SEQ ID NO:252.

In one embodiment, the VH includes the amino acid sequence of SEQ ID NO:246 and the VL includes the amino acid sequence of SEQ ID NO:251. In one embodiment, the VH includes the amino acid sequence of SEQ ID NO:246 and the VL includes the amino acid sequence of SEQ ID NO:250. In one embodiment, the VH includes the amino acid sequence of SEQ ID NO:246 and the VL includes the amino acid sequence of SEQ ID NO:252.

In one embodiment, the VH includes the amino acid sequence of SEQ ID NO:247 and the VL includes the amino acid sequence of SEQ ID NO:251. In one embodiment, the VH includes the amino acid sequence of SEQ ID NO:247 and the VL includes the amino acid sequence of SEQ ID NO:250. In one embodiment, the VH includes the amino acid sequence of SEQ ID NO:247 and the VL includes the amino acid sequence of SEQ ID NO:252.

In one embodiment, the VH includes the amino acid sequence of SEQ ID NO:248 and the VL includes the amino acid sequence of SEQ ID NO:251. In one embodiment, the VH includes the amino acid sequence of SEQ ID NO:248 and the VL includes the amino acid sequence of SEQ ID NO:250. In one embodiment, the VH includes the amino acid sequence of SEQ ID NO:248 and the VL includes the amino acid sequence of SEQ ID NO:252.

In one embodiment, the VH includes the amino acid sequence of SEQ ID NO:249 and the VL includes the amino acid sequence of SEQ ID NO:251. In one embodiment, the VH includes the amino acid sequence of SEQ ID NO:249 and the VL includes the amino acid sequence of SEQ ID NO:250. In one embodiment, the VH includes the amino acid sequence of SEQ ID NO:249 and the VL includes the amino acid sequence of SEQ ID NO:252.

Also provided, in some embodiments, are antibodies and antigen-binding fragments therefore that bind to the same epitope on LIV-1 as 290F10G10. Also provided, in some embodiments, are antibodies and antigen-binding fragments therefore that competes with 290F10G10 in binding to LIV-1.

In some embodiments, provided is an antibody or antigen-binding fragment that is derived from antibody 13F4C8. In some embodiments, the VH CDR1, VH CDR2, VH CDR3, VL CDR1, VL CDR2, and VL CDR3, respectively, include the amino acid sequences of SEQ ID NO: 63-68. In some embodiments, the VH includes the amino acid sequence of SEQ ID NO: 3 or a sequence having at least 75%, 80%, 85%, 90%, 95% or 99% sequence identity to SEQ ID NO: 3, while retaining the corresponding VH CDRs. In some embodiments, the VL includes the amino acid sequence of SEQ ID NO: 4 or a sequence having at least 75%, 80%, 85%, 90%, 95% or 99% sequence identity to SEQ ID NO: 4, while retaining the corresponding VL CDRs. Also provided, in some embodiments, are antibodies and antigen-binding fragments therefore that bind to the same epitope on LIV-1 as 13F4C8. Also provided, in some embodiments, are antibodies and antigen-binding fragments therefore that competes with 13F4C8 in binding to LIV-1.

In some embodiments, provided is an antibody or antigen-binding fragment that is derived from antibody 39D10B2. In some embodiments, the VH CDR1, VH CDR2, VH CDR3, VL CDR1, VL CDR2, and VL CDR3, respectively, include the amino acid sequences of SEQ ID NO: 69-74. In some embodiments, the VH includes the amino acid sequence of SEQ ID NO: 5 or a sequence having at least 75%, 80%, 85%, 90%, 95% or 99% sequence identity to SEQ ID NO: 5, while retaining the corresponding VH CDRs. In some embodiments, the VL includes the amino acid sequence of SEQ ID NO: 6 or a sequence having at least 75%, 80%, 85%, 90%, 95% or 99% sequence identity to SEQ ID NO: 6, while retaining the corresponding VL CDRs. Also provided, in some embodiments, are antibodies and antigen-binding fragments therefore that bind to the same epitope on LIV-1 as 39D10B2. Also provided, in some embodiments, are antibodies and antigen-binding fragments therefore that competes with 39D10B2 in binding to LIV-1.

In some embodiments, provided is an antibody or antigen-binding fragment that is derived from antibody 47G1B10. In some embodiments, the VH CDR1, VH CDR2, VH CDR3, VL CDR1, VL CDR2, and VL CDR3, respectively, include the amino acid sequences of SEQ ID NO: 75-80. In some embodiments, the VH includes the amino acid sequence of SEQ ID NO: 7 or a sequence having at least 75%, 80%, 85%, 90%, 95% or 99% sequence identity to SEQ ID NO: 7, while retaining the corresponding VH CDRs. In some embodiments, the VL includes the amino acid sequence of SEQ ID NO: 8 or a sequence having at least 75%, 80%, 85%, 90%, 95% or 99% sequence identity to SEQ ID NO: 8, while retaining the corresponding VL CDRs. Also provided, in some embodiments, are antibodies and antigen-binding fragments therefore that bind to the same epitope on LIV-1 as 47G1B10. Also provided, in some embodiments, are antibodies and antigen-binding fragments therefore that competes with 47G1B10 in binding to LIV-1.

In some embodiments, provided is an antibody or antigen-binding fragment that is derived from antibody 50H12B3. In some embodiments, the VH CDR1, VH CDR2, VH CDR3, VL CDR1, VL CDR2, and VL CDR3, respectively, include the amino acid sequences of SEQ ID NO: 81-86. In some embodiments, the VH includes the amino acid sequence of SEQ ID NO: 9 or a sequence having at least 75%, 80%, 85%, 90%, 95% or 99% sequence identity to SEQ ID NO: 9, while retaining the corresponding VH CDRs. In some embodiments, the VL includes the amino acid sequence of SEQ ID NO: 10 or a sequence having at least 75%, 80%, 85%, 90%, 95% or 99% sequence identity to SEQ ID NO: 10, while retaining the corresponding VL CDRs. Also provided, in some embodiments, are antibodies and antigen-binding fragments therefore that bind to the same epitope on LIV-1 as 50H12B3. Also provided, in some embodiments, are antibodies and antigen-binding fragments therefore that competes with 50H12B3 in binding to LIV-1.

In some embodiments, provided is an antibody or antigen-binding fragment that is derived from antibody 56B3E6. In some embodiments, the VH CDR1, VH CDR2, VH CDR3, VL CDR1, VL CDR2, and VL CDR3, respectively, include the amino acid sequences of SEQ ID NO: 87-92. In some embodiments, the VH includes the amino acid sequence of SEQ ID NO: 11 or a sequence having at least 75%, 80%, 85%, 90%, 95% or 99% sequence identity to SEQ ID NO: 11, while retaining the corresponding VH CDRs. In some embodiments, the VL includes the amino acid sequence of SEQ ID NO: 12 or a sequence having at least 75%, 80%, 85%, 90%, 95% or 99% sequence identity to SEQ ID NO: 12, while retaining the corresponding VL CDRs. Also provided, in some embodiments, are antibodies and antigen-binding fragments therefore that bind to the same epitope on LIV-1 as 56B3E6. Also provided, in some embodiments, are antibodies and antigen-binding fragments therefore that competes with 56B3E6 in binding to LIV-1.

In some embodiments, provided is an antibody or antigen-binding fragment that is derived from antibody 59C12C8. In some embodiments, the VH CDR1, VH CDR2, VH CDR3, VL CDR1, VL CDR2, and VL CDR3, respectively, include the amino acid sequences of SEQ ID NO: 93-98. In some embodiments, the VH includes the amino acid sequence of SEQ ID NO: 13 or a sequence having at least 75%, 80%, 85%, 90%, 95% or 99% sequence identity to SEQ ID NO: 13, while retaining the corresponding VH CDRs. In some embodiments, the VL includes the amino acid sequence of SEQ ID NO: 14 or a sequence having at least 75%, 80%, 85%, 90%, 95% or 99% sequence identity to SEQ ID NO: 14, while retaining the corresponding VL CDRs. Also provided, in some embodiments, are antibodies and antigen-binding fragments therefore that bind to the same epitope on LIV-1 as 59C12C8. Also provided, in some embodiments, are antibodies and antigen-binding fragments therefore that competes with 59C12C8 in binding to LIV-1.

In some embodiments, provided is an antibody or antigen-binding fragment that is derived from antibody 69B3D6. In some embodiments, the VH CDR1, VH CDR2, VH CDR3, VL CDR1, VL CDR2, and VL CDR3, respectively, include the amino acid sequences of SEQ ID NO: 99-104. In some embodiments, the VH includes the amino acid sequence of SEQ ID NO: 15 or a sequence having at least 75%, 80%, 85%, 90%, 95% or 99% sequence identity to SEQ ID NO: 15, while retaining the corresponding VH CDRs. In some embodiments, the VL includes the amino acid sequence of SEQ ID NO: 16 or a sequence having at least 75%, 80%, 85%, 90%, 95% or 99% sequence identity to SEQ ID NO: 16, while retaining the corresponding VL CDRs. Also provided, in some embodiments, are antibodies and antigen-binding fragments therefore that bind to the same epitope on LIV-1 as 69B3D6. Also provided, in some embodiments, are antibodies and antigen-binding fragments therefore that competes with 69B3D6 in binding to LIV-1.

In some embodiments, provided is an antibody or antigen-binding fragment that is derived from antibody 72B12F1. In some embodiments, the VH CDR1, VH CDR2, VH CDR3, VL CDR1, VL CDR2, and VL CDR3, respectively, include the amino acid sequences of SEQ ID NO: 105-110. In some embodiments, the VH includes the amino acid sequence of SEQ ID NO: 17 or a sequence having at least 75%, 80%, 85%, 90%, 95% or 99% sequence identity to SEQ ID NO: 17, while retaining the corresponding VH CDRs. In some embodiments, the VL includes the amino acid sequence of SEQ ID NO: 18 or a sequence having at least 75%, 80%, 85%, 90%, 95% or 99% sequence identity to SEQ ID NO: 18, while retaining the corresponding VL CDRs. Also provided, in some embodiments, are antibodies and antigen-binding fragments therefore that bind to the same epitope on LIV-1 as 72B12F1. Also provided, in some embodiments, are antibodies and antigen-binding fragments therefore that competes with 72B12F1 in binding to LIV-1.

In some embodiments, provided is an antibody or antigen-binding fragment that is derived from antibody 79F5G5. In some embodiments, the VH CDR1, VH CDR2, VH CDR3, VL CDR1, VL CDR2, and VL CDR3, respectively, include the amino acid sequences of SEQ ID NO: 111-116. In some embodiments, the VH includes the amino acid sequence of SEQ ID NO: 19 or a sequence having at least 75%, 80%, 85%, 90%, 95% or 99% sequence identity to SEQ ID NO: 19, while retaining the corresponding VH CDRs. In some embodiments, the VL includes the amino acid sequence of SEQ ID NO: 20 or a sequence having at least 75%, 80%, 85%, 90%, 95% or 99% sequence identity to SEQ ID NO: 20, while retaining the corresponding VL CDRs. Also provided, in some embodiments, are antibodies and antigen-binding fragments therefore that bind to the same epitope on LIV-1 as 79F5G5. Also provided, in some embodiments, are antibodies and antigen-binding fragments therefore that competes with 79F5G5 in binding to LIV-1.

In some embodiments, provided is an antibody or antigen-binding fragment that is derived from antibody 82C7C7. In some embodiments, the VH CDR1, VH CDR2, VH CDR3, VL CDR1, VL CDR2, and VL CDR3, respectively, include the amino acid sequences of SEQ ID NO: 117-122. In some embodiments, the VH includes the amino acid sequence of SEQ ID NO: 21 or a sequence having at least 75%, 80%, 85%, 90%, 95% or 99% sequence identity to SEQ ID NO: 21, while retaining the corresponding VH CDRs. In some embodiments, the VL includes the amino acid sequence of SEQ ID NO: 22 or a sequence having at least 75%, 80%, 85%, 90%, 95% or 99% sequence identity to SEQ ID NO: 22, while retaining the corresponding VL CDRs. Also provided, in some embodiments, are antibodies and antigen-binding fragments therefore that bind to the same epitope on LIV-1 as 82C7C7. Also provided, in some embodiments, are antibodies and antigen-binding fragments therefore that competes with 82C7C7 in binding to LIV-1.

In some embodiments, provided is an antibody or antigen-binding fragment that is derived from antibody 90H4F8. In some embodiments, the VH CDR1, VH CDR2, VH CDR3, VL CDR1, VL CDR2, and VL CDR3, respectively, include the amino acid sequences of SEQ ID NO: 123-128. In some embodiments, the VH includes the amino acid sequence of SEQ ID NO: 23 or a sequence having at least 75%, 80%, 85%, 90%, 95% or 99% sequence identity to SEQ ID NO: 23, while retaining the corresponding VH CDRs. In some embodiments, the VL includes the amino acid sequence of SEQ ID NO: 24 or a sequence having at least 75%, 80%, 85%, 90%, 95% or 99% sequence identity to SEQ ID NO: 24, while retaining the corresponding VL CDRs. Also provided, in some embodiments, are antibodies and antigen-binding fragments therefore that bind to the same epitope on LIV-1 as 90H4F8. Also provided, in some embodiments, are antibodies and antigen-binding fragments therefore that competes with 90H4F8 in binding to LIV-1.

In some embodiments, provided is an antibody or antigen-binding fragment that is derived from antibody 92E4E10. In some embodiments, the VH CDR1, VH CDR2, VH CDR3, VL CDR1, VL CDR2, and VL CDR3, respectively, include the amino acid sequences of SEQ ID NO: 129-134. In some embodiments, the VH includes the amino acid sequence of SEQ ID NO: 25 or a sequence having at least 75%, 80%, 85%, 90%, 95% or 99% sequence identity to SEQ ID NO: 25, while retaining the corresponding VH CDRs. In some embodiments, the VL includes the amino acid sequence of SEQ ID NO: 26 or a sequence having at least 75%, 80%, 85%, 90%, 95% or 99% sequence identity to SEQ ID NO: 26, while retaining the corresponding VL CDRs. Also provided, in some embodiments, are antibodies and antigen-binding fragments therefore that bind to the same epitope on LIV-1 as 92E4E10. Also provided, in some embodiments, are antibodies and antigen-binding fragments therefore that competes with 92E4E10 in binding to LIV-1.

In some embodiments, provided is an antibody or antigen-binding fragment that is derived from antibody 94C4B9. In some embodiments, the VH CDR1, VH CDR2, VH CDR3, VL CDR1, VL CDR2, and VL CDR3, respectively, include the amino acid sequences of SEQ ID NO: 135-140. In some embodiments, the VH includes the amino acid sequence of SEQ ID NO: 27 or a sequence having at least 75%, 80%, 85%, 90%, 95% or 99% sequence identity to SEQ ID NO: 27, while retaining the corresponding VH CDRs. In some embodiments, the VL includes the amino acid sequence of SEQ ID NO: 28 or a sequence having at least 75%, 80%, 85%, 90%, 95% or 99% sequence identity to SEQ ID NO: 28, while retaining the corresponding VL CDRs. Also provided, in some embodiments, are antibodies and antigen-binding fragments therefore that bind to the same epitope on LIV-1 as 94C4B9. Also provided, in some embodiments, are antibodies and antigen-binding fragments therefore that competes with 94C4B9 in binding to LIV-1.

In some embodiments, provided is an antibody or antigen-binding fragment that is derived from antibody 99B3E8. In some embodiments, the VH CDR1, VH CDR2, VH CDR3, VL CDR1, VL CDR2, and VL CDR3, respectively, include the amino acid sequences of SEQ ID NO: 141-146. In some embodiments, the VH includes the amino acid sequence of SEQ ID NO: 29 or a sequence having at least 75%, 80%, 85%, 90%, 95% or 99% sequence identity to SEQ ID NO: 29, while retaining the corresponding VH CDRs. In some embodiments, the VL includes the amino acid sequence of SEQ ID NO: 30 or a sequence having at least 75%, 80%, 85%, 90%, 95% or 99% sequence identity to SEQ ID NO: 30, while retaining the corresponding VL CDRs. Also provided, in some embodiments, are antibodies and antigen-binding fragments therefore that bind to the same epitope on LIV-1 as 99B3E8. Also provided, in some embodiments, are antibodies and antigen-binding fragments therefore that competes with 99B3E8 in binding to LIV-1.

In some embodiments, provided is an antibody or antigen-binding fragment that is derived from antibody 99D12B8. In some embodiments, the VH CDR1, VH CDR2, VH CDR3, VL CDR1, VL CDR2, and VL CDR3, respectively, include the amino acid sequences of SEQ ID NO: 147-152. In some embodiments, the VH includes the amino acid sequence of SEQ ID NO: 31 or a sequence having at least 75%, 80%, 85%, 90%, 95% or 99% sequence identity to SEQ ID NO: 31, while retaining the corresponding VH CDRs. In some embodiments, the VL includes the amino acid sequence of SEQ ID NO: 32 or a sequence having at least 75%, 80%, 85%, 90%, 95% or 99% sequence identity to SEQ ID NO: 32, while retaining the corresponding VL CDRs. Also provided, in some embodiments, are antibodies and antigen-binding fragments therefore that bind to the same epitope on LIV-1 as 99D12B8. Also provided, in some embodiments, are antibodies and antigen-binding fragments therefore that competes with 99D12B8 in binding to LIV-1.

In some embodiments, provided is an antibody or antigen-binding fragment that is derived from antibody 109C9D4. In some embodiments, the VH CDR1, VH CDR2, VH CDR3, VL CDR1, VL CDR2, and VL CDR3, respectively, include the amino acid sequences of SEQ ID NO: 153-158. In some embodiments, the VH includes the amino acid sequence of SEQ ID NO: 33 or a sequence having at least 75%, 80%, 85%, 90%, 95% or 99% sequence identity to SEQ ID NO: 33, while retaining the corresponding VH CDRs. In some embodiments, the VL includes the amino acid sequence of SEQ ID NO: 34 or a sequence having at least 75%, 80%, 85%, 90%, 95% or 99% sequence identity to SEQ ID NO: 34, while retaining the corresponding VL CDRs. Also provided, in some embodiments, are antibodies and antigen-binding fragments therefore that bind to the same epitope on LIV-1 as 109C9D4. Also provided, in some embodiments, are antibodies and antigen-binding fragments therefore that competes with 109C9D4 in binding to LIV-1.

In some embodiments, provided is an antibody or antigen-binding fragment that is derived from antibody 112H11C12. In some embodiments, the VH CDR1, VH CDR2, VH CDR3, VL CDR1, VL CDR2, and VL CDR3, respectively, include the amino acid sequences of SEQ ID NO: 159-164. In some embodiments, the VH includes the amino acid sequence of SEQ ID NO: 35 or a sequence having at least 75%, 80%, 85%, 90%, 95% or 99% sequence identity to SEQ ID NO: 35, while retaining the corresponding VH CDRs. In some embodiments, the VL includes the amino acid sequence of SEQ ID NO: 36 or a sequence having at least 75%, 80%, 85%, 90%, 95% or 99% sequence identity to SEQ ID NO: 36, while retaining the corresponding VL CDRs. Also provided, in some embodiments, are antibodies and antigen-binding fragments therefore that bind to the same epitope on LIV-1 as 112H11C12. Also provided, in some embodiments, are antibodies and antigen-binding fragments therefore that competes with 112H11C12 in binding to LIV-1.

In some embodiments, provided is an antibody or antigen-binding fragment that is derived from antibody 127A2B9. In some embodiments, the VH CDR1, VH CDR2, VH CDR3, VL CDR1, VL CDR2, and VL CDR3, respectively, include the amino acid sequences of SEQ ID NO: 171-176. In some embodiments, the VH includes the amino acid sequence of SEQ ID NO: 39 or a sequence having at least 75%, 80%, 85%, 90%, 95% or 99% sequence identity to SEQ ID NO: 39, while retaining the corresponding VH CDRs. In some embodiments, the VL includes the amino acid sequence of SEQ ID NO: 40 or a sequence having at least 75%, 80%, 85%, 90%, 95% or 99% sequence identity to SEQ ID NO: 40, while retaining the corresponding VL CDRs. Also provided, in some embodiments, are antibodies and antigen-binding fragments therefore that bind to the same epitope on LIV-1 as 127A2B9. Also provided, in some embodiments, are antibodies and antigen-binding fragments therefore that competes with 127A2B9 in binding to LIV-1.

In some embodiments, provided is an antibody or antigen-binding fragment that is derived from antibody 136F3D10C10. In some embodiments, the VH CDR1, VH CDR2, VH CDR3, VL CDR1, VL CDR2, and VL CDR3, respectively, include the amino acid sequences of SEQ ID NO:177-182. In some embodiments, the VH includes the amino acid sequence of SEQ ID NO: 41 or a sequence having at least 75%, 80%, 85%, 90%, 95% or 99% sequence identity to SEQ ID NO: 41, while retaining the corresponding VH CDRs. In some embodiments, the VL includes the amino acid sequence of SEQ ID NO: 42 or a sequence having at least 75%, 80%, 85%, 90%, 95% or 99% sequence identity to SEQ ID NO: 42, while retaining the corresponding VL CDRs. Also provided, in some embodiments, are antibodies and antigen-binding fragments therefore that bind to the same epitope on LIV-1 as 136F3D10C10. Also provided, in some embodiments, are antibodies and antigen-binding fragments therefore that competes with 136F3D10C10 in binding to LIV-1.

In some embodiments, provided is an antibody or antigen-binding fragment that is derived from antibody 135C6E7. In some embodiments, the VH CDR1, VH CDR2, VH CDR3, VL CDR1, VL CDR2, and VL CDR3, respectively, include the amino acid sequences of SEQ ID NO: 183-188. In some embodiments, the VH includes the amino acid sequence of SEQ ID NO: 43 or a sequence having at least 75%, 80%, 85%, 90%, 95% or 99% sequence identity to SEQ ID NO: 43, while retaining the corresponding VH CDRs. In some embodiments, the VL includes the amino acid sequence of SEQ ID NO: 44 or a sequence having at least 75%, 80%, 85%, 90%, 95% or 99% sequence identity to SEQ ID NO: 44, while retaining the corresponding VL CDRs. Also provided, in some embodiments, are antibodies and antigen-binding fragments therefore that bind to the same epitope on LIV-1 as 135C6E7. Also provided, in some embodiments, are antibodies and antigen-binding fragments therefore that competes with 135C6E7 in binding to LIV-1.

In some embodiments, provided is an antibody or antigen-binding fragment that is derived from antibody 108H1D4. In some embodiments, the VH CDR1, VH CDR2, VH CDR3, VL CDR1, VL CDR2, and VL CDR3, respectively, include the amino acid sequences of SEQ ID NO:189-194. In some embodiments, the VH includes the amino acid sequence of SEQ ID NO: 45 or a sequence having at least 75%, 80%, 85%, 90%, 95% or 99% sequence identity to SEQ ID NO: 45, while retaining the corresponding VH CDRs. In some embodiments, the VL includes the amino acid sequence of SEQ ID NO: 46 or a sequence having at least 75%, 80%, 85%, 90%, 95% or 99% sequence identity to SEQ ID NO: 46, while retaining the corresponding VL CDRs. Also provided, in some embodiments, are antibodies and antigen-binding fragments therefore that bind to the same epitope on LIV-1 as 108H1D4. Also provided, in some embodiments, are antibodies and antigen-binding fragments therefore that competes with 108H1D4 in binding to LIV-1.

In some embodiments, provided is an antibody or antigen-binding fragment that is derived from antibody 248H1G3. In some embodiments, the VH CDR1, VH CDR2, VH CDR3, VL CDR1, VL CDR2, and VL CDR3, respectively, include the amino acid sequences of SEQ ID NO: 195-200. In some embodiments, the VH includes the amino acid sequence of SEQ ID NO: 47 or a sequence having at least 75%, 80%, 85%, 90%, 95% or 99% sequence identity to SEQ ID NO: 47, while retaining the corresponding VH CDRs. In some embodiments, the VL includes the amino acid sequence of SEQ ID NO: 48 or a sequence having at least 75%, 80%, 85%, 90%, 95% or 99% sequence identity to SEQ ID NO: 48, while retaining the corresponding VL CDRs. Also provided, in some embodiments, are antibodies and antigen-binding fragments therefore that bind to the same epitope on LIV-1 as 248H1G3. Also provided, in some embodiments, are antibodies and antigen-binding fragments therefore that competes with 248H1G3 in binding to LIV-1.

In some embodiments, provided is an antibody or antigen-binding fragment that is derived from antibody 282G5A2. In some embodiments, the VH CDR1, VH CDR2, VH CDR3, VL CDR1, VL CDR2, and VL CDR3, respectively, include the amino acid sequences of SEQ ID NO:201-206. In some embodiments, the VH includes the amino acid sequence of SEQ ID NO: 49 or a sequence having at least 75%, 80%, 85%, 90%, 95% or 99% sequence identity to SEQ ID NO: 49, while retaining the corresponding VH CDRs. In some embodiments, the VL includes the amino acid sequence of SEQ ID NO: 50 or a sequence having at least 75%, 80%, 85%, 90%, 95% or 99% sequence identity to SEQ ID NO: 50, while retaining the corresponding VL CDRs. Also provided, in some embodiments, are antibodies and antigen-binding fragments therefore that bind to the same epitope on LIV-1 as 282G5A2. Also provided, in some embodiments, are antibodies and antigen-binding fragments therefore that competes with 282G5A2 in binding to LIV-1.

In some embodiments, provided is an antibody or antigen-binding fragment that is derived from antibody 286B5E6. In some embodiments, the VH CDR1, VH CDR2, VH CDR3, VL CDR1, VL CDR2, and VL CDR3, respectively, include the amino acid sequences of SEQ ID NO: 207-212. In some embodiments, the VH includes the amino acid sequence of SEQ ID NO: 51 or a sequence having at least 75%, 80%, 85%, 90%, 95% or 99% sequence identity to SEQ ID NO: 51, while retaining the corresponding VH CDRs. In some embodiments, the VL includes the amino acid sequence of SEQ ID NO: 52 or a sequence having at least 75%, 80%, 85%, 90%, 95% or 99% sequence identity to SEQ ID NO: 52, while retaining the corresponding VL CDRs. Also provided, in some embodiments, are antibodies and antigen-binding fragments therefore that bind to the same epitope on LIV-1 as 286B5E6. Also provided, in some embodiments, are antibodies and antigen-binding fragments therefore that competes with 286B5E6 in binding to LIV-1.

In some embodiments, provided is an antibody or antigen-binding fragment that is derived from antibody 293F10B6. In some embodiments, the VH CDR1, VH CDR2, VH CDR3, VL CDR1, VL CDR2, and VL CDR3, respectively, include the amino acid sequences of SEQ ID NO:219-224. In some embodiments, the VH includes the amino acid sequence of SEQ ID NO: 55 or a sequence having at least 75%, 80%, 85%, 90%, 95% or 99% sequence identity to SEQ ID NO: 55, while retaining the corresponding VH CDRs. In some embodiments, the VL includes the amino acid sequence of SEQ ID NO: 56 or a sequence having at least 75%, 80%, 85%, 90%, 95% or 99% sequence identity to SEQ ID NO: 56, while retaining the corresponding VL CDRs. Also provided, in some embodiments, are antibodies and antigen-binding fragments therefore that bind to the same epitope on LIV-1 as 293F10B6. Also provided, in some embodiments, are antibodies and antigen-binding fragments therefore that competes with 13F4C8 in binding to LIV-1.

Also provided, in some embodiments, are antibodies and antigen-binding fragments that include CDR sequences derived from the presently disclosed CDR sequences, with one, two or three amino acid substitutions, deletions, and/or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Antibody-Drug Conjugates

In some embodiments, the antibodies or fragments may be conjugated to therapeutic agents, prodrugs, peptides, proteins, enzymes, viruses, lipids, biological response modifiers, pharmaceutical agents, or PEG.

In one embodiment, the antibodies or fragments of the disclosure are covalently attached to a drug moiety. The drug moiety may be, or be modified to include, a group reactive with a conjugation point on the antibody. For example, a drug moiety can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols.

In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 20, about 1 to about 10, about 2 to about 10, about 2 to about 9, about 1 to about 8, about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3.

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

The drug can be linked to the antibody or fragment by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio).

In some embodiments, the drug moiety is a cytotoxic or cytostatic agent, an immunosuppressive agent, a radioisotope, a toxin, or the like. The conjugate can be used for inhibiting the multiplication of a tumor cell or cancer cell, causing apoptosis in a tumor or cancer cell, or for treating cancer in a patient. The conjugate can be used accordingly in a variety of settings for the treatment of animal cancers. The conjugate can be used to deliver a drug to a tumor cell or cancer cell. Without being bound by theory, in some embodiments, the conjugate binds to or associates with a cancer cell expressing LIV-1, and the conjugate and/or drug can be taken up inside a tumor cell or cancer cell through receptor-mediated endocytosis.

In some embodiments, the drug moiety is a maytansinoid or an auristatin. In some embodiments, the drug moiety is a macrocyclic ketone analogue such as eribulin. In some embodiments, the drug moiety is a topoisomerase inhibitor, such as exatecan and exatecan derivatives.

Once inside the cell, one or more specific peptide sequences within the conjugate (e.g., in a linker) are hydrolytically cleaved by one or more tumor-cell or cancer-cell-associated proteases, resulting in release of the drug. The released drug is then free to migrate within the cell and induce cytotoxic or cytostatic or other activities. In some embodiments, the drug is cleaved from the antibody outside the tumor cell or cancer cell, and the drug subsequently penetrates the cell, or acts at the cell surface.

Examples of drug moieties or payloads are selected from the group consisting of eribulin (2-(3-Amino-2-hydroxypropyl) hexacosahydro-3-methoxy-26-methyl-20,27-bis(methylene) 11,15-18,21-24,28-triepoxy-7,9-ethano-12,15-methano-9H,15H-furo (3,2-i)furo(2',3'-5,6)pyrano(4,3-b)(1, 4)dioxacyclopentacosin-5-(4H)-one), DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[(1S)-2-phenyl-1-(2-thiazolyl)ethyl]amino]propyl]-1-pyrrolidinyl]-1-[(1S)-1-methylpropyl]-4-oxobutyl]-N-methyl-(9Cl)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino) heptanoyl-(αR,βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[N-[6-(2,5-dihydro-2,5-dioxo-1H-pyrrol-1-yl)-1-oxohexyl]-L-valyl-N5-(aminocarbonyl)-L-ornithyl]amino]phenyl]methoxy]carbonyl]-N-methyl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide).

DM1 is a derivative of the tubulin inhibitor maytansine while MMAD, MMAE, and MMAF are auristatin derivatives. In some embodiments, the drug moiety is selected from the group consisting of mc-MMAF and mc-Val-Cit-PABA-MMAE.

The antibodies or fragments may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

In some embodiments, examples of the payload-linker include:
(LM-D01)
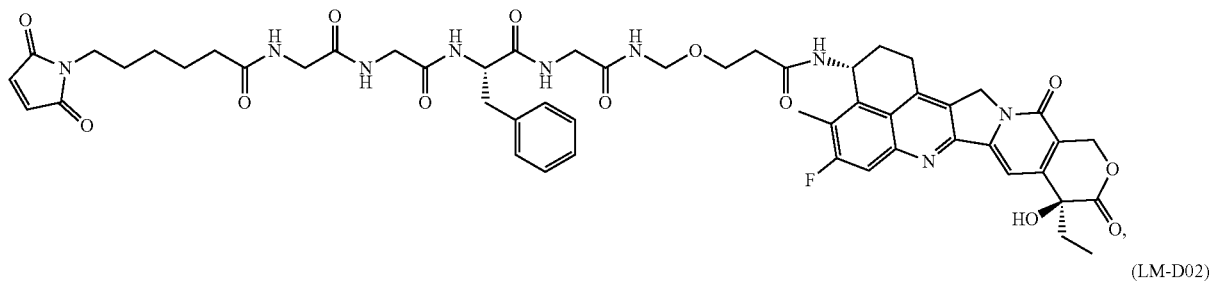
(LM-D02)
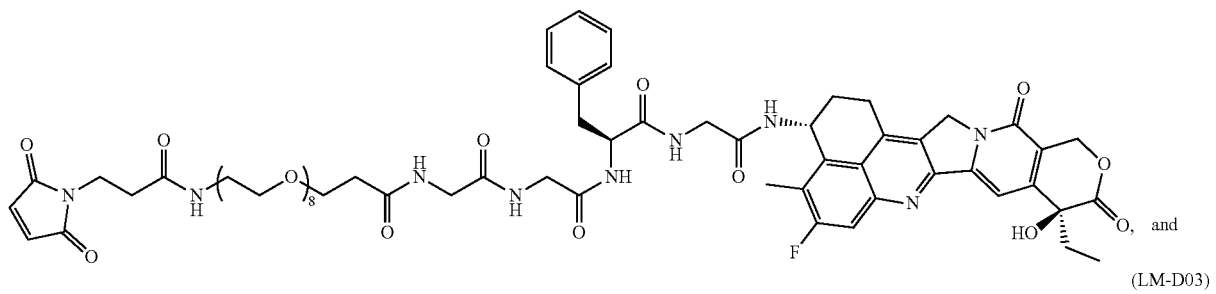
(LM-D03)
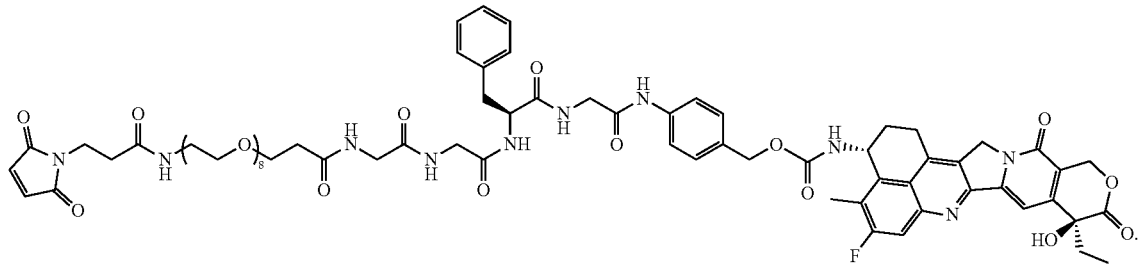
In some embodiments, provided is an ADC selected from:
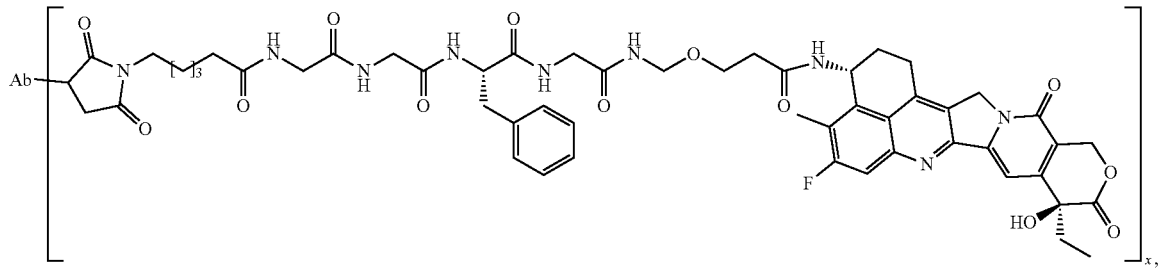
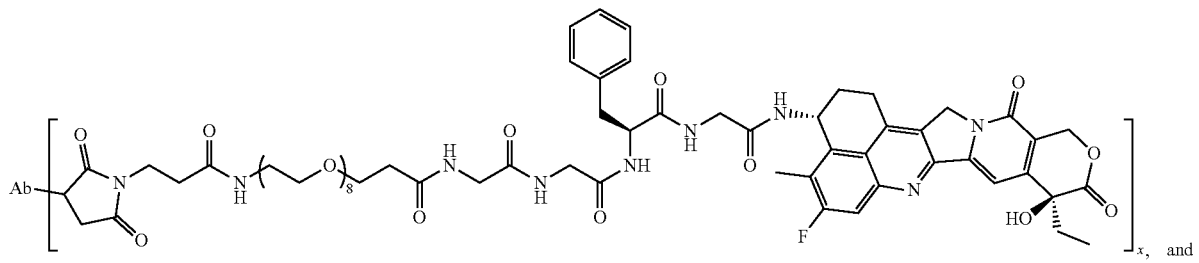

-continued

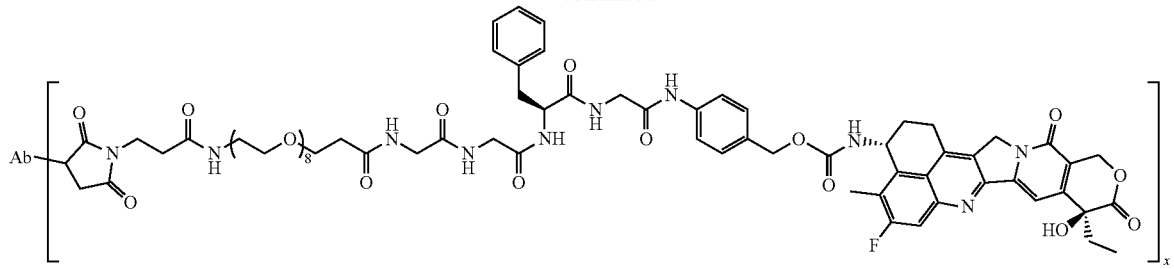

wherein Ab is an antibody or an antigen-binding fragment provided herein.

In some embodiments, x is 4. In some embodiments, x is 5. In some embodiments, x is 6. In some embodiments, x is 7. In some embodiments, x is 8. In some embodiments, x is 4, 6, or 8. In some embodiments, x is 4-8.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Multi-Functional Molecules

Multi-functional molecules that include an antibody or antigen-binding fragment specific to LIV-1, such as those disclosed herein, and one or more antibody or antigen-binding fragment having specificity to a second antigen.

In some embodiments, the second antigen is a protein expressed on an immune cell, such as a T cell, a B cell, a monocyte, a macrophage, a neutrophil, a dendritic cell, a phagocyte, a natural killer cell, an eosinophil, a basophil, and a mast cell.

In some embodiments, the second antigen is CD3, CD47, PD1, PD-L1, LAG3, TIM3, CTLA4, VISTA, CSFR1, A2AR, CD73, CD39, CD40, CEA, HER2, CMET, 4-1BB, OX40, SIRPA CD16, CD28, ICOS, CTLA4, BTLA, TIGIT, HVEM, CD27, VEGFR, or VEGF.

Different formats of bispecific antibodies are also provided. In some embodiments, each of the anti-LIV-1 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to LIV-1, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Chimeric Antigen Receptors

Also provided, in one embodiment, is a chimeric antigen receptor (CAR) that includes the antibody or fragment thereof of the present disclosure as a targeting unit. In some embodiments, the CAR includes an antibody or fragment thereof of the present disclosure, a transmembrane domain, a costimulatory domain, and a CD35 intracellular domain.

A transmembrane domain can be designed to be fused to the extracellular domain which includes the antibody or fragment, optionally through a hinge domain. It can similarly be fused to an intracellular domain, such as a costimulatory domain. In some embodiments, the transmembrane domain can include the natural transmembrane region of a costimulatory domain (e.g., the TM region of a CD28T or 4-1BB employed as a costimulatory domain) or the natural transmembrane domain of a hinge region (e.g., the TM region of a CD8 alpha or CD28T employed as a hinge domain).

In some embodiments, the transmembrane domain can include a sequence that spans a cell membrane, but extends into the cytoplasm of a cell and/or into the extracellular space. For example, a transmembrane can include a membrane-spanning sequence which itself can further include 1, 2, 3, 4, 5, 6, 7, 8, 9, 10 or more amino acids that extend into the cytoplasm of a cell, and/or the extracellular space. Thus, a transmembrane domain includes a membrane-spanning region, yet can further comprise an amino acid(s) that extend beyond the internal or external surface of the membrane itself; such sequences can still be considered to be a "transmembrane domain".

In some embodiments, the transmembrane domain is fused to the cytoplasmic domain through a short linker. Optionally, the short peptide or polypeptide linker, preferably between 2 and 10 amino acids in length can form the linkage between the transmembrane domain and a proximal cytoplasmic signaling domain of the chimeric receptor. A glycine-serine doublet (GS), glycine-serine-glycine triplet (GSG), or alanine-alanine-alanine triplet (AAA) provides a suitable linker.

In some embodiments, the CAR further includes a costimulatory domain. In some embodiments, the costimulatory domain is positioned between the transmembrane domain and an activating domain. Example costimulatory domains include, but are not limited to, CD2, CD3 delta, CD3 epsilon, CD3 gamma, CD4, CD7, CD8a, CD8, CD11a (ITGAL), CD11b (ITGAM), CD11c (ITGAX), CD11d (ITGAD), CD18 (ITGB2), CD19 (B4), CD27 (T FRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAMI), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD 100 (SEMA4D), CD 103 (ITGAE), CD134 (OX40), CD137 (4-1BB), CD150 (SLAMF1), CD158A (KIR2DL1), CD158B (KIR2DL2), CD158B2 (KIR2DL3), CD158C (KIR3DP1), CD158D (KIRDL4), CD158F1 (KIR2DL5A), CD158F2 (KIR2DL5B), CD158K (KTR3DL2), CD160 (BY55), CD162 (SELPLG), CD226 (DNAMI), CD229 (SLAMF3), CD244 (SLAMF4), CD247 (CD3-zeta), CD258 (LIGHT), CD268 (BAFFR), CD270 (T FSF14), CD272 (BTLA), CD276 (B7-H3), CD279 (PD-1), CD314 (KG2D), CD319 (SLAMF7), CD335 (K-p46), CD336 (K-p44), CD337 (K-p30), CD352 (SLAMF6), CD353 (SLAMF8), CD355 (CRTAM), CD357 (TNFRSF 18), inducible T cell co-stimulator (ICOS), LFA-1 (CD 11a/CD 18), KG2C, DAP-10, ICAM-1, Kp80 (KLRFI), IL-2R beta, IL-2R gamma, IL-7R alpha, LFA-1, SLAMF9, LAT, GADS (GrpL), SLP-76 (LCP2), PAGI/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof.

In some embodiments, the cytoplasmic portion of the CAR also includes a signaling/activation domain. In one embodiment, the signaling/activation domain is the CD38 domain, or is an amino acid sequence having at least about 80%, 85%, 90%, 95%, 98% or 99% sequence identity to the CD3ξ domain.

Polynucleotides, mRNA, and Methods of Expressing or Preparing Antibodies

The present disclosure also provides polynucleotides or nucleic acid molecules encoding the antibodies, variants or derivatives thereof of the disclosure, or the CAR. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

In some embodiments, the polynucleotide is an mRNA molecule. In some embodiments, the mRNA can be introduced into a target cell for expressing the antibody or fragment thereof.

mRNAs may be synthesized according to any of a variety of known methods. For example, the mRNAs may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of antibody-coding mRNA, a DNA template is transcribed in vitro. A suitable DNA template typically has a promoter, for example a T3, T7 or SP6 promoter, for in vitro transcription, followed by desired nucleotide sequence for desired antibody encoding (e.g., heavy chain or light chain encoding) mRNA and a termination signal.

Desired antibody encoding (e.g., heavy chain or light chain encoding) mRNA sequence may be determined and incorporated into a DNA template using standard methods. For example, starting from a desired amino acid sequence (e.g., a desired heavy chain or light chain sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

The mRNA may be synthesized as unmodified or modified mRNA. Typically, mRNAs are modified to enhance stability. Modifications of mRNA can include, for example, modifications of the nucleotides of the RNA. A modified mRNA can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, 13-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, the mRNAs (e.g., heavy chain and light chain encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, the mRNAs (e.g., heavy chain and light chain encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, the mRNAs (e.g., heavy chain and light chain encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, the mRNAs (e.g., heavy chain and light chain encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5)A and G(5)ppp(5')G.

In some embodiments, the mRNAs (e.g., heavy chain and light chain encoding mRNAs) include a 3' poly(A) tail structure. A poly-A tail on the 3' terminus of mRNA typically includes about 10 to 300 adenosine nucleotides (e.g., about 10 to 200 adenosine nucleotides, about 10 to 175 adenosine nucleotides, about 10 to 150 adenosine nucleotides, about 10 to 125 adenosine nucleotides, 10 to 100 adenosine nucleotides, about 10 to 75 adenosine nucleotides, about 20 to 70 adenosine nucleotides, or about 20 to 60 adenosine nucleotides). In some embodiments, antibody encoding mRNAs (e.g., heavy chain and light chain encoding mRNAs) include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNAs (e.g., heavy chain and light chain encoding mRNAs) include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length (e.g., about 50 and 400 nucleotides in length, about 50 and 300 nucleotides in length, about 50 and 200 nucleotides in length, or about 50 and 100 nucleotides in length).

In some embodiments, a 5' region of an mRNA (e.g., heavy chain and light chain encoding mRNAs) includes a sequence encoding a signal peptide, such as those described herein. In particular embodiments, a signal peptide derived from human growth hormone (hGH) is incorporated in the 5' region. Typically, a signal peptide encoding sequence is linked, directly or indirectly, to the heavy chain or light chain encoding sequence at the N-terminus.

The present technology may be used to deliver any antibody known in the art and antibodies that can be produced against desired antigens using standard methods. The present invention may be used to deliver monoclonal antibodies, polyclonal antibodies, antibody mixtures or cocktails, human or humanized antibodies, chimeric antibodies, or bi-specific antibodies.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants, derivatives or antibody-drug conjugates of the present disclosure may be used in certain treatment and diagnostic methods.

The present disclosure is further directed to antibody-based therapies which involve administering the antibodies, fragments, or antibody-drug conjugates of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. As provided above, LIV-1 can be overexpressed in tumor cells, in particular gastric, pancreatic, esophageal, ovarian, and lung tumors. Inhibition of LIV-1 has been shown to be useful for treating the tumors.

Accordingly, in some embodiments, provided are methods for treating a cancer in a patient in need thereof. The method, in one embodiment, entails administering to the patient an effective amount of an antibody, fragment, or antibody-drug conjugate of the present disclosure. In some embodiments, at least one of the cancer cells (e.g., stromal cells) in the patient over-express LIV-1.

Cellular therapies, such as chimeric antigen receptor (CAR) T-cell therapies, are also provided in the present disclosure. A suitable cell can be used, that is put in contact with an anti-LIV-1 antibody of the present disclosure (or alternatively engineered to express an anti-LIV-1 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is one or more of gastric, pancreatic, esophageal, ovarian, and lung cancers.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, fragments, or antibody-drug conjugates or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies, fragments, or antibody-drug conjugates of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges.

The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antibodies, fragments, or antibody-drug conjugates of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-$\alpha$.

In additional embodiments, the compositions of the disclosure are administered in combination with other therapeutic or prophylactic regimens, such as, for example, radiation therapy.

Compositions

The present disclosure also provides pharmaceutical compositions. Such compositions comprise an effective amount of an antibody, fragment, or antibody-drug conjugate, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Murine Monoclonal Antibodies Against Human LIV-1

Balb/c and C57/BL6 mice were immunized with eukaryotic expression vectors, encoding human LIV-1 fragments. 50 µg of plasmid DNA was injected into the quadriceps (intramuscular, i.m.) on day 1 and 10. The presence of antibodies directed against human LIV-1 in the serum of the mice was monitored on day 20 by flow cytometry, using HEK293 cells transiently transfected with a nucleic acid encoding human LIV-1. Mice with detectable immune responses were boosted three and two days prior to fusion by intraperitoneal injection of HEK293 cells transiently transfected with a nucleic acid encoding human LIV-1.

Hybridoma cells were harvested and total RNA was extracted using Tri Reagent as described above for spleen tissue. cDNA was prepared using SuperScript III kit according to the manufacturer's instruction. The resulting cDNA product was used as template for PCR with primers, the resulting PCR product was cleaned up using a PCR clean-up kit and sequenced with the same primer. Sequencing reactions were performed on cleaned PCR product to obtain DNA sequences for the antibodies, 5D6B10, 13F4C8, 39D10B2, 47G1B10, 50H12B3, 56B3E6, 59C12C8, 69B3D6, 72B12F1, 79F5G5, 82C7C7, 90H4F8, 92E4E10, 94C4B9, 99B3E8, 99D12B8, 109C9D4, 112H11C12, 124H4D11, 127A2B9, 136F3D10C10, 135C6E7, 108H1D4, 248H1G3, 282G5A2, 286B5E6, 290F10G10, and 293F10B6. Their variable (VH and VL) sequences are shown in Table 1A below, and their CDR sequences are summarized in Table 1B.

TABLE 1A

Sequences of the variable regions of the antibodies

| Antibody | Sequence | SEQ ID NO: |
|---|---|---|
| 5D6B10 VH | QVQLKQSGPGLVQPSQSLSITCTVSGFSLTTYGIHWVRQSPGKGLEWLGVIWTGGTTDYNAAFISRLSISKDNSKSQVFFKMNSLQANDTAIYYCARGPSSYWGQGTLVTVSA | 1 |
| 5D6B10 VL | DIVMTQSQKFMSTVGDRVSVTCKASQNVDTNVVWYQQKPGQSPKALIHSASYRYSGVPDRFTGSGSGTDFTLTISNVQSEDLAEYFCQQYNNYPWTFGGGTKLEIK | 2 |
| 13F4C8 VH | QVQLQQPGSELVRPGASVKLSCKASGYTFTSSWMHWLKQRPGHGLAWIGRIYPGSGSTVYDEKFKSKAILTVDTSSNTAYMQLSSLTSEDSAVYYCTRSMVTAAWFAYWGQGTLVTVSA | 3 |
| 13F4C8 VL | DFLMTQTPLSLPVSLGDQASISCRSSRSIVHSNGNTYLEWYLQKPGQSPKLLIYKVSNRFSGVPDRFSGSGSGTDFTLKISRVEAEDLGLYYCFQGSHVPYTFGGGTKLEIK | 4 |
| 39D10B2 VH | QVQLKQSGPGLVQPSQSLSITCTVSGFSLTTYGVHWVRQSPGKGLEWLGVIWTGGTTDYNAAFISRLSISKDNSKSQVFFKMNSLQANDTAMYYCARGPSSYWGQGTLVTVSA | 5 |
| 39D10B2 VL | DIVMTQSQKFMSTVGDRVSVTCKASQNVDTNVVWYQQKPGQSPKALIHSASYRYSGVPDRFTGSGSGTDFTLTISNVQSEDLAEYFCQQYNNYPWTFGGGTKLEIK | 6 |
| 47G1B10 VH | QVQLKQSGPGLVQPSQSLSITCTVSGFSLTTYGVHWVRQSPGKGLEWLGVIWTGGTTDYNAAFISRLSISKDNSKSQVFFKMNSLQANDTAIYYCARGPSSYWGQGTLVTVSA | 7 |
| 47G1B10 VL | DIVMTQSQKFMSTVGDRVSVTCKASQNVDTNVVWYQQKPGQSPKALIHSASYRYSGVPDRFTGSGSGTDFTLTISNVQSEDLAEYFCQQYNNYPWTFGGGTKLEIK | 8 |
| 50H12B3 VH | QVQLKQSGPGLVQPSQSLSITCTVSGFSLTSYGVHWVRQSPGKGLEWLGVIWTGGTTDYNAAFKSRLSISKDNSKSQVFFKMNSLQANDTAIYYCARGPSSYWGQGTLVTVSA | 9 |
| 50H12B3 VL | DIVMTQSQKFMSTVGDRVSVTCKASQNVDTNVVWYQQKPGQSPKALIHSTSYRYSGVPDRFTGSGSGTDFTLTISNVQSEDLAEYFCQQYNNYPWTFGGGTKLEIK | 10 |
| 56B3E6 VH | EVQLQQSGAELVRSGASVKLSCTASGFNIKDYYIHWVKQRPEQGLEWIGWIDPENDDTEYAPKFQGKATMTADTSSNTAYLHLSSLTSEDTAVYYCPHGGGFRVFDSWGQGTTLTVSS | 11 |
| 56B3E6 VL | DVLMTQTPLSLPVSLGDQASISCRSSQDIVHSNGNTYLEWYLQKPGQSPKLLIYKVSNRFSGVPDRFSGSGSGTDFTLKISRVEAEDLGVYYCFQGSHVPWTFGGGTKLEIK | 12 |
| 59C12C8 VH | EVQLQQSGAELVRSGASVKLSCTASDFNIEDYYIHWVKQRPEQGLEWIGWIDPENGDTEYAPKFQGKATMTADTSSNTAYLQLSSLTSEDTAVYYCPHGGGFRVFDYWGQGTTLTVSS | 13 |
| 59C12C8 VL | DVLMTQTPLSLPVSLGDQASISCRSSQRIVHSNGNTYLEWYLQKPGQSPKLLIYKVSNRFSGVPDRFSGSGSGTDFTLKISRVEAEDLGVYYCFQGSHVPWTFGGGTKLEIK | 14 |
| 69B3D6 VH | QVQLQQSGPELVKPGASVRISCKASGYTFTSYHMHWVKQRPGQGLEWIGWIYPGNVKNQSNEKFKGKATLTADKSSSTAYMQLSSLTSEDSAVYFCARSDITRAFFAYWGQGTLVTVSA | 15 |

TABLE 1A-continued

Sequences of the variable regions of the antibodies

| Antibody | Sequence | SEQ ID NO: |
|---|---|---|
| 69B3D6 VL | DVLMTQTPLSLPVSLGDQASISCRSSQSIVHSNGNTYLEWYLQKPGQSPK LLIYKVSNRFSGVPDRFSGSGSGTDFTLKISRVEAEDLGVYYCFQGSHVP YTFGGGTKLEIK | 16 |
| 72B12F1 VH | EVQLQQSGAELVKPGASVKLSCTASGFNIKDTYMHWVKQRPEQGLEWIGR IDPANGNTKNDPRFQGKATITADTSSNTAYLQLSRLTSEDTAVYYCAGGG ITTVVPDHWGQGTTLTVSS | 17 |
| 72B12F1 VL | DVVMTQTPLSLPVSLGDQASISCRSSQSLVHSNGNTYLQWYLQKPGQSPK LLIYKVSNRFSGVPDRFSGSGSGTDFTLKISRVEAEDLGVYFCSQSTHVP YTFGGGTKLEIK | 18 |
| 79F5G5 VH | EVQLQQSGAELVRSGASVKLSCTASGFNIKDYYMHWVKQRPEQGLEWIGW IDPENGDTEYAPKFQGKATLTADTSSNTAYLQLSSLTFEDTAVYYCPHGG GLRVFDYWGQGTSLTVSS | 19 |
| 79F5G5 VL | DVLMTQIPLSLSVSLGDQASISCRSSQSIVHSNGNTYLEWYLQKPGQSPK LLIYKVSNRFSGVPDRFSGSGSGTDFTLKISRVEAEDLGVYYCFQGSHVP WTFGGGTKLEIK | 20 |
| 82C7C7 VH | EVQLQQSGAELVKPGASIKLSCTPSGFNIKDTFIHWVKQRPEQGLEWIGR IDPANGNTRYDPKFQGKATITADTSSNTAYLQLISLTSEDTAVYYCAGGS ISTVVPDYWGQGTTLTVSS | 21 |
| 82C7C7 VL | DVVVTQTPLSLPVSLGDQASISCRSSQSLVHNNGNTYLHWYLQKPGQSPK LLIYKVSNRFSGVPDRFSGSGSGTDFTLKISRVEAEDLGVYFCSQSTHVP YTFGGGTKLEIK | 22 |
| 90H4F8 VH | QVQLQQSGPELVKPGASVRISCKASGYTFTSYHMHWVKQRPGQGLEWIGW IYPGNVKNQSNEKFKGKATLTADKSSSTAYMHLSSLTSEDSAVYFCARSD ITRAFFAYWGQGTLVTVSA | 23 |
| 90H4F8 VL | DVLMTQTPLSLPVSLGDQASISCRSSQSIVHSNGNTYLEWYLQKPGQSPK LLIYKVSNRFSGVPDRFSGSGSGTDFTLKISRVEAEDLGVYYCFQGSHGP YTFGGGTKLEIK | 24 |
| 92E4E10 VH | EVQLQQSGTVLARPGASVKISCKASGYRFTSYWMHWVKQRPGQGLEWIGA IYPGNSDTTYNQKFKGKAKLTAVTSASTAYMDLSSLTNEDSAVYYCTSLL LRSPFDYWGQGTTLTVSS | 25 |
| 92E4E10 VL | DVVMTQTPLTLSVTIGQPASISCKSSQSLLDSDGKTNLNWLLQRPGQSPK RLIYLVSKLDSGVPDRFTGSGSGTDFTLKISRVEAEDLGVYYCCQGIQFP RTFGGGTKLEIK | 26 |
| 94C4B9 VH | EVQLQQSGTVLARPGASVKMSCKASGYTFINYWMHWVKQRPGQGLEWIGA FYPGNSDTSYNQKFKDKAKLTAVTSTSTAYMEFSSLTNEDSAVYYCTRDF TAVPYFDYWGQGTTLTVSS | 27 |
| 94C4B9 VL | DILMTQTPLSLPVSLGDQASISCRSSQSIVHSNGNTYLEWYLQKPGQSPK LLIYKVSNRFSGVPDRFSGSGSGTDFTLKISRVEAEDLGVYYCFQGSYVP LTFGVGTKLELK | 28 |
| 99B3E8 VH | EVQLQQSGTVLARPGTSVKMSCKASGYTFINYWMHWVRQRPGQGLEWIGA FYPGNSDTSYNQNFKDKAKLTAVTSTSTAYMEFSSLTNEDSAVYYCTRDF TAVPFFDYWGQGTTLTVSS | 29 |
| 99B3E8 VL | DVLMTQTPLSLPVSLGDQASISCRSSQSIVHSNGNTYLEWYLQKPGQSPK LLIYKVSNRFSGVPDRFSGSGSGTDFTLKISRVEAEDLGVYYCFQGSYVP LTFGVGTKLELK | 30 |
| 99D12B8 VH | QVHLQQSGPELVRPGASVRISCKASNYTFTSYYLHWVKQRPGQGLEWIGW IYPGNGNTQYNGKFKGQATLTADKSSSTADIHFSSLTSEDSAVYFCARSD ISRAFFAYWGQGTLVTVSA | 31 |
| 99D12B8 VL | QVHLQQSGPELVRPGASVRISCKASNYTFTSYYLHWVKQRPGQGLEWIGW IYPGNGNTQYNGKFKGQATLTADKSSSTADIHFSSLTSEDSAVYFCARSD ISRAFFAYWGQGTLVTVSA | 32 |
| 109C9D4 VH | EVKLVESGGGLVQPGGSRKLSCAASGFTFSDYGMAWVRQAPGKGPEWVTF ISNLAYSIYYADTVTGRFTISRENAKNTLYLEMSSLRSEDTAMYYCARVE ENGNYFDYWGQGTTLTVSS | 33 |

TABLE 1A-continued

Sequences of the variable regions of the antibodies

| Antibody | Sequence | SEQ ID NO: |
|---|---|---|
| 109C9D4 VL | DIQMTQTTSSLSASLGDRVTIRCRASQDIGIYLHWYQQKPDGTVKLLIYYTSRLHSGVPSRFSGSRSGTDYSLTIGNLEQEDIATYFCLQGNTIPPTFGGGTKLEIK | 34 |
| 112H11C12 VH | QVQLQQPGAELVRPGASVKLSCKASGYTFTSYWMNWVKQRPGQGLKWIGMIDPSNSKTHYNQMFKDKATLTVDKSSNTAYMQLSSLTSEDSAVYYCARTSTTMATFAYWGQGTLVSVSA | 35 |
| 112H11C12 VL | DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQASHFPLTFGAGTELDLN | 36 |
| 124H4D11 VH | EVPLQQSGAELVRSGASVKLSCTASGFNIKDYYMHWVKQRPEQGLEWIGWIDPENGDTEYDPKFQGKATMTADTSSNTADLQLSSLTSEDTAVYYCNARYYAFDYWGQGTTLTVSS | 37 |
| 124H4D11 VL | DVLMTQTPLSLPVSLGDQASISCRSSQSIVHSNGNTYLEWYLQKPGQSPKLLIYKVSNRFSGVPDRFSGSGSGTEFTLKISRVEAEDLGVYYCFQGSQVPPTFGGGTRLEIK | 38 |
| 127A2B9 VH | EVQLQESGPSLVKPSQTLSLTCSVTGDSITSGYWNWIRKLPGNKLEYMGYISYSGSTYYNPSLKSRISITRDTSKNQYYLQLNSVTTEDTATYYCARIYYDYDGYFDVWGAGTTVTVSS | 39 |
| 127A2B9 VL | DIVMTQAAPSVPVTPGESVSISCRSSKSLLHSNGNTFLYWFLQRPGQSPQLLIYRMSNLASGVPDRFSGSGSGTAFTLRISRVEAEDVGVYYCMQHLEYPYTFGGGTKLEIK | 40 |
| 136F3D10C10 VH | QVQLQQSGPELVKPGASVRIFCKASGYTFTSFHIHWVKQRPGQGLEWIGWIYPGNDNTDHNEKFKGKATLSADKSSSTVYMQLSSLTSEDSAVYFCGRSNYYGPLFAYWGQGTLVTVSA | 41 |
| 136F3D10C10 VL | DILMTQTPLSLPVSLGDQASISCRSSQNIVRSNGNTYLEWYLQKPGQSPKVLIYRVSNRFSGVPDRFSGSGSGTDFTLKISRVEAEDLGVYYCFQGSYVPYTFGGGTKLEIK | 42 |
| 135C6E7 VH | EVQLVESGGGLVQPKGSLKLSCAASGFTFNTYAMNWVRQAPGKGLEWVARIRSKYNSYATYYADSVKDRFTISRDDSQSILYLQMNNLKTEDTAMYYCVRHEDYDGGFAYWGQGTLVTVSA | 43 |
| 135C6E7 VL | DIVMSQSPSSLAVSVGEKVTMSCKSSQSLFKSRTRKNYLAWYQQKPGQSPKLLIYWASTRESGVPDRFTGSGSGTDFTLTISSVQAEDLAVYYCKESYNLMYTFGGGTKLEIK | 44 |
| 108H1D4 VH | EVKLVESGGDLVQPGGSRKLSCAASGFTFSDYGMAWFRQAPGKGPEWVAFISNLAYNIYYADTVTGRFTISRENARNTLYLEMSSLRSEDTAMYYCAREGGITTVPATDYFDYWGQGTTLTVSS | 45 |
| 108H1D4 VL | DIQMTQTTSSLSASLGDRVTFSCRASQDIRNYLNWYQQKPDGTVKLLIYYTSRLHSGVPSRFSGSGSGTDYSLTINNLEQEDLATYFCQQVNALPLT**FGAGTKLELK | 46 |
| 248H1G3 VH | EVQLQQSGPELMKRGASVKISCKTSTFTFTEFTIHWVKQSHGKSLEWIGGINPNTGGTSYNQNFTGKATLTVDKSSITAYMELRSLTSEDSAIYYCAPNWDGYWFFDVWGAGTTVTVSS | 47 |
| 248H1G3 VL | DIQMTQSPASLSASVGETVTITCRASGNIQNYLAWYQQKQGKSPQLLVYGAKTLADGVPSRFSGSGSGTQFSLKINSLQPEDFGSYYCQHFWSPPLTFGAGTKLELK | 48 |
| 282G5A2 VH | QVQLQQSGAELVRPGTSVKVSCKASGYALTKYLIEWIKQRPGQGLEWIGVINPGNAGNNYNEKFKGKATLTVDQSSTAYMQLSSLTSEDSAVYFCARRGRDYAMDNWGQGTSVTVSS | 49 |
| 282G5A2 VL | EIVLTQSPAIMSASLGEKVTMSCRASSSINYIYWYQQKSDASPKLWIYYTSNLAPGVPARFSGSGSGNSYSLTISSMEDEDAATYYCQQFTSSPLTFGAGTKLELK | 50 |
| 286B5E6 VH | QVTLKESGPGILQPSQTLSLTCSFSGFSLSTSGMGVSWIRQPSGKGLEWLAHIFWDDDKRYNPSLKSRLTLSKDTSSNQVFLKITSVDTADTATYYCARRARHNYPWFPYWGQGTLVTVSA | 51 |
| 286B5E6 VL | DIVLTQSPASLAVSLGQRATISCKASQSVDYDGDSYMNWYQQKPGQPPKLLIYAASNLESGIPARFSGSGSGTDFTLNIHPVEEEDAATYYCQQSNEGPYTFGGGTKLEIK | 52 |

TABLE 1A-continued

Sequences of the variable regions of the antibodies

| Antibody | Sequence | SEQ ID NO: |
|---|---|---|
| 290F10G10 VH | IQLQQSGAELARPGASVKLSCKASGYTFTSYWIHWVKERPGQGLEWIGTIYPGDGDTRSTQKFKDKATVTAEKSSSTVYMQLSSLASEDSAVYYCTRSLIHDDYDKYYFDYWGQGTTLTVSS | 53 |
| 290F10G10 VL | DIQMTQSPSSLSASLGGKVTITCKARQDINKYIAWYQHKPGKGPRLLIHYTSILQPGIPSRFSGSGSGRDYSFSISNLEPEDIATYYCLQYDYFFTFGSGTKLEIK | 54 |
| 293F10B6 VH | QVTLKESGPGMLQPSQTLNLTCSFSGFSLNTSGMGVSWIRQPSGKGLEWLAHIFWDDDKRYNPSLKSRLTISKDVSSNQVFLKITSVDTADTATYFCARRARNNYPWFPYWGQGTLVTVSA | 55 |
| 293F10B6 VL | DIVLTQSPASLAVSLGQRATISCKASQSVDYDGDSYMNWYQQKPGQPPKLLIYAASNLDSGIPARFSGSGSGTDFTLNIHPMEDEDVATYYCQQSNGAPFTFGGGTKLEIK | 56 |

TABLE 1B

CDR Sequences

| Antibody | Sequence | SEQ ID NO: |
|---|---|---|
| 5D6B10 VH | TYGIH | 57 |
| | VIWTGGTTDYNAAFIS | 58 |
| | GPSSY | 59 |
| 5D6B10 VL | KASQNVDTNVV | 60 |
| | SASYRYS | 61 |
| | QQYNNYPWT | 62 |
| 13F4C8 VH | SSWMH | 63 |
| | RIYPGSGSTVYDEKFKS | 64 |
| | SMVTAAWFAY | 65 |
| 13F4C8 VL | RSSRSIVHSNGNTYLE | 66 |
| | KVSNRFS | 67 |
| | FQGSHVPYT | 68 |
| 39D10B2 VH | TYGVH | 69 |
| | VIWTGGTTDYNAAFIS | 70 |
| | GPSSY | 71 |
| 39D10B2 VL | KASQNVDTNVV | 72 |
| | SASYRYS | 73 |
| | QQYNNYPWT | 74 |
| 47G1B10 VH | TYGVH | 75 |
| | VIWTGGTTDYNAAFIS | 76 |
| | GPSSY | 77 |
| 47G1B10 VL | KASQNVDTNVV | 78 |
| | SASYRYS | 79 |
| | QQYNNYPWT | 80 |
| 50H12B3 VH | SYGVH | 81 |
| | VIWTGGTTDYNAAFKS | 82 |
| | GPSSY | 83 |
| 50H12B3 VL | KASQNVDTNVV | 84 |
| | STSYRYS | 85 |
| | QQYNNYPWT | 86 |
| 56B3E6 VH | DYYIH | 87 |
| | WIDPENDDTEYAPKFQG | 88 |
| | GGGFRVFDS | 89 |
| 56B3E6 VL | RSSQDIVHSNGNTYLE | 90 |
| | KVSNRFS | 91 |
| | FQGSHVPWT | 92 |
| 59C12C8 VH | DYYIH | 93 |
| | WIDPENGDTEYAPKFQG | 94 |
| | GGGFRVFDY | 95 |
| 59C12C8 VL | RSSQRIVHSNGNTYLE | 96 |
| | KVSNRFS | 97 |
| | FQGSHVPWT | 98 |
| 69B3D6 VH | SYHMH | 99 |
| | WIYPGNVKNQSNEKFKG | 100 |
| | SDITRAFFAY | 101 |
| 69B3D6 VL | RSSQSIVHSNGNTYLE | 102 |
| | KVSNRFS | 103 |
| | FQGSHVPYT | 104 |
| 72B12F1 VH | DTYMH | 105 |
| | RIDPANGNTKNDPRFQG | 106 |
| | GGITTVVPDH | 107 |
| 72B12F1 VL | RSSQSLVHSNGNTYLQ | 108 |
| | KVSNRFS | 109 |
| | SQSTHVPYT | 110 |
| 79F5G5 VH | DYYMH | 111 |
| | WIDPENGDTEYAPKFQG | 112 |
| | GGGLRVFDY | 113 |
| 79F5G5 VL | RSSQSIVHSNGNTYLE | 114 |
| | KVSNRFS | 115 |
| | FQGSHVPWT | 116 |
| 82C7C7 VH | DTFIH | 117 |
| | RIDPANGNTRYDPKFQG | 118 |
| | GSISTVVPDY | 119 |
| 82C7C7 VL | RSSQSLVHNNGNTYLH | 120 |
| | KVSNRFS | 121 |
| | SQSTHVPYT | 122 |
| 90H4F8 VH | SYHMH | 123 |
| | WIYPGNVKNQSNEKFKG | 124 |
| | SDITRAFFAY | 125 |
| 90H4F8 VL | RSSQSIVHSNGNTYLE | 126 |
| | KVSNRFS | 127 |
| | FQGSHGPYT | 128 |

TABLE 1B-continued

CDR Sequences

| Antibody | Sequence | SEQ ID NO: |
|---|---|---|
| 92E4E10 VH | SYWMH | 129 |
| | AIYPGNSDTTYNQKFKG | 130 |
| | LLLRSPFDY | 131 |
| 92E4E10 VL | KSSQSLLDSDGKTNLN | 132 |
| | LVSKLDS | 133 |
| | CQGIQFPRT | 134 |
| 94C4B9 VH | NYWMH | 135 |
| | AFYPGNSDTSYNQKFKD | 136 |
| | DFTAVPYFDY | 137 |
| 94C4B9 VL | RSSQSIVHSNGNTYLE | 138 |
| | KVSNRFS | 139 |
| | FQGSYVPLT | 140 |
| 99B3E8 VH | NYWMH | 141 |
| | AFYPGNSDTSYNQNFKD | 142 |
| | DFTAVPFFDY | 143 |
| 99B3E8 VL | RSSQSIVHSNGNTYLE | 144 |
| | KVSNRFS | 145 |
| | FQGSYVPLT | 146 |
| 99D12B8 VH | SYYLH | 147 |
| | WIYPGNGNTQYNGKFKG | 148 |
| | SDISRAFFAY | 149 |
| 99D12B8 VL | SYYLH | 150 |
| | WIYPGNGNTQYNGKFKG | 151 |
| | SDISRAFFAY | 152 |
| 109C9D4 VH | DYGMA | 153 |
| | FISNLAYSIYYADTVTG | 154 |
| | VEENGNYFDY | 155 |
| 109C9D4 VL | RASQDIGIYLH | 156 |
| | YTSRLHS | 157 |
| | LQGNTIPPT | 158 |
| 112H11C12 VH | SYWMN | 159 |
| | MIDPSNSKTHYNQMFKD | 160 |
| | TSTTMATFAY | 161 |
| 112H11C12 VL | RSSQSIVHSNGNTYLE | 162 |
| | KVSNRFS | 163 |
| | FQASHFPLT | 164 |
| 124H4D11 VH | DYYMH | 165 |
| | WIDPENGDTEYDPKFQG | 166 |
| | RYYAFDY | 167 |
| 124H4D11 VL | RSSQSIVHSNGNTYLE | 168 |
| | KVSNRFS | 169 |
| | FQGSQVPPT | 170 |
| 127A2B9 VH | SGYWN | 171 |
| | YISYSGSTYYNPSLKS | 172 |
| | IYYDYDGYFDV | 173 |
| 127A2B9 VL | RSSKSLLHSNGNTFLY | 174 |
| | RMSNLAS | 175 |
| | MQHLEYPYT | 176 |
| 136F3D10C10 VH | SFHIH | 177 |
| | WIYPGNDNTDHNEKFKG | 178 |
| | SNYYGPLFAY | 179 |
| 136F3D10C10 VL | RSSQNIVRSNGNTYLE | 180 |
| | RVSNRFS | 181 |
| | FQGSYVPYT | 182 |
| 135C6E7 VH | TYAMN | 183 |
| | RIRSKYNSYATYYADSVKD | 184 |
| | HEDYDGGFAY | 185 |
| 135C6E7 VL | KSSQSLFKSRTRKNYLA | 186 |
| | WASTRES | 187 |
| | KESYNLMYT | 188 |
| 108H1D4 VH | DYGMA | 189 |
| | FISNLAYNIYYADTVTG | 190 |
| | EGGITTVPATDYFDY | 191 |
| 108H1D4 VL | RASQDIRNYLN | 192 |
| | YTSRLHS | 193 |
| | QQVNALPLT | 194 |
| 248H1G3 VH | EFTIH | 195 |
| | GINPNTGGTSYNQNFTG | 196 |
| | NWDGYWFFDV | 197 |
| 248H1G3 VL | RASGNIQNYLA | 198 |
| | GAKTLAD | 199 |
| | QHFWSPPLT | 200 |
| 282G5A2 VH | KYLIE | 201 |
| | VINPGNAGNNYNEKFKG | 202 |
| | RGRDYAMDN | 203 |
| 282G5A2 VL | RASSSINYIY | 204 |
| | YTSNLAP | 205 |
| | QQFTSSPLT | 206 |
| 286B5E6 VH | TSGMGVS | 207 |
| | HIFWDDDKRYNPSLKS | 208 |
| | RARHNYPWFPY | 209 |
| 286B5E6 VL | KASQSVDYDGDSYMN | 210 |
| | AASNLES | 211 |
| | QQSNEGPYT | 212 |
| 290F10G10 VH | SYWIH | 213 |
| | TIYPGDGDTRSTQKFKD | 214 |
| | SLIHDDYDKYYFDY | 215 |
| 290F10G10 VL | KARQDINKYIA | 216 |
| | YTSILQP | 217 |
| | LQYDYFFT | 218 |
| 293F10B6 VH | TSGMGVS | 219 |
| | HIFWDDDKRYNPSLKS | 220 |
| | RARNNYPWFPY | 221 |
| 293F10B6 VL | KASQSVDYDGDSYMN | 222 |
| | AASNLDS | 223 |
| | QQSNGAPFT | 224 |

Example 2. FACS Binding of Chimeric Antibodies to Cell-Expressed Human and Cyno LIV-1

In this example, cell based binding of chimeric Abs on human and cyno LIV-1 overexpressing HEK 293 cells were assessed using flow cytometry.

Briefly, cells were incubated with chimeric Abs (from 100 nM, 5 folds dilution, 8 points). After incubation at 4° C. for 60 minutes, the cells were washed with 2% FBS/PBS buffer twice, then stained with fluorescent conjugated secondary antibody at 4° C. for 30 minutes. After that the cells were washed twice and resuspended in 80 µL of 2% FBS/PBS buffer. Fluorescent signal of binding was detected using Agilent. The EC50 was calculated using the GraphPad Software (LaJolla, CA).

Figure 1B:
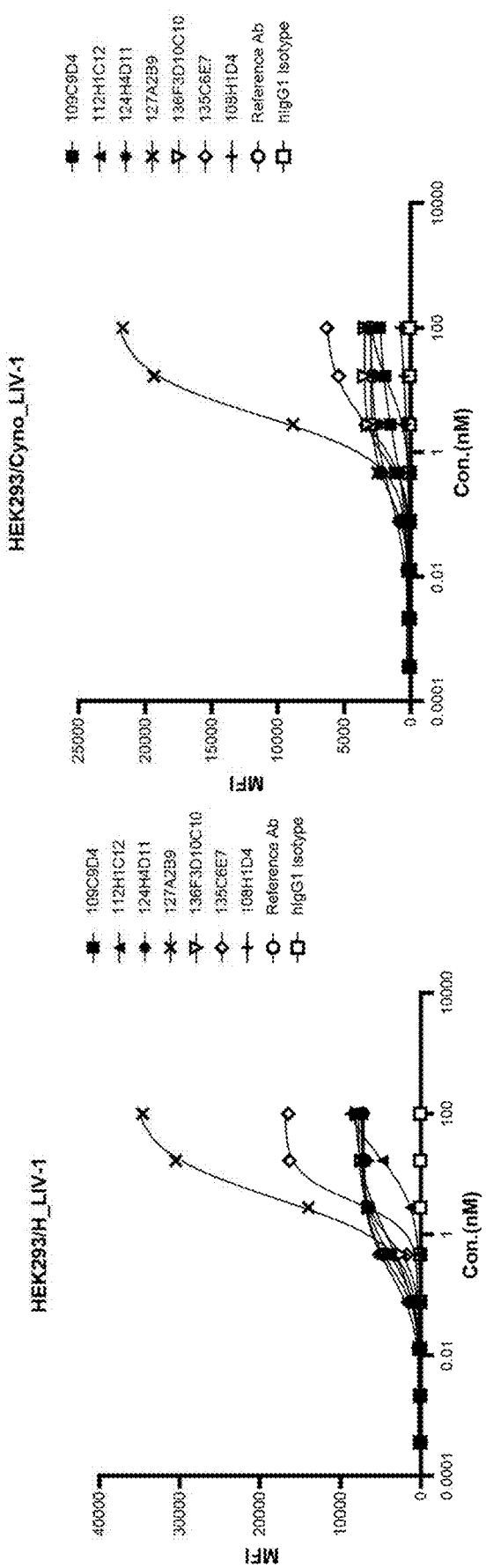
Figure 1C:
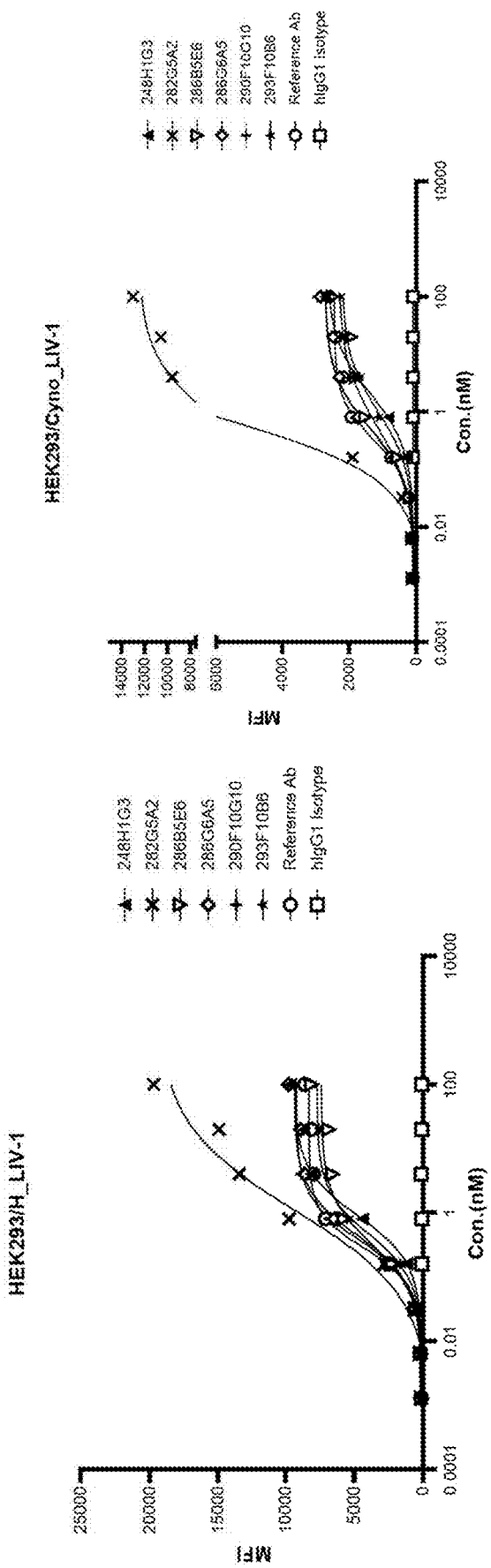

The results are shown in FIG. 1A-C and Table 2. Many of the tested chimeric antibodies showed strong binding to both human and cyno LIV-1 expressed on cells.

TABLE 2

FACS Binding of chimeric Abs to Human LIV-1 and Cynomolgus LIV-1

| | HEK293/H_LIV-1 | | HEK293/Cyno_LIV-1 | |
|---|---|---|---|---|
| Antibody | $EC_{50}$ (nM) | Top (MFI) | $EC_{50}$ (nM) | Top (MFI) |
| 5D6B10 | 0.21 | 70115 | 0.17 | 41097 |
| 13F4C8L1 | 1.83 | 13016 | 438.10 | 8568 |
| 39D10B2 | 0.24 | 61755 | 0.21 | 37345 |
| 47G1B10 | 0.37 | 60896 | 0.30 | 36712 |
| 50H12B3 | 0.23 | 63000 | 0.21 | 35876 |
| 56B3E6 | 0.13 | 13349 | 0.21 | 9285 |
| 59C12C8 | 0.10 | 15111 | 0.11 | 8055 |
| 69B3D6 | 0.18 | 11491 | 0.17 | 6605 |
| 72B12F1 | 0.79 | 10701 | 0.36 | 7466 |
| 79F5G5 | 9.45 | 17464 | 1.85 | 7015 |
| 82C7C7 | 0.61 | 12343 | 0.50 | 7128 |
| 90H4F8 | 1.08 | 12250 | 0.43 | 6876 |
| 92E4E10 | 0.34 | 66208 | 0.15 | 41341 |
| 94C4B9 | 0.22 | 11561 | 0.15 | 7857 |
| 99B3E8 | 1.04 | 12635 | 0.34 | 8241 |
| 99D12B8 | 0.18 | 11250 | 0.11 | 6870 |
| Reference Ab | 0.19 | 14566 | 0.13 | 8894 |
| hIgG1 Isotype | NA | 183 | NA | 181 |
| 109C9D4 | 0.43 | 7343 | 1.33 | 2344 |
| 112H1C12 | 20.70 | 8804 | 12.01 | 2927 |
| 124H4D11 | 0.23 | 7982 | 0.20 | 3367 |
| 127A2B9 | 4.03 | 34628 | 3.92 | 21712 |
| 136F3D10C10 | 0.85 | 7909 | 0.76 | 3446 |
| 135C6E7 | 3.60 | 16451 | 2.69 | 6288 |
| 108H1D4 | 0.90 | 8800 | 130.00 | 762 |
| Reference Ab | 0.27 | 7277 | 0.21 | 3122 |
| hIgG1 Isotype | NA | 114 | NA | 99 |
| 248H1G3 | 0.89 | 9643 | 2.05 | 2700 |
| 282G5A2 | 1.12 | 19700 | 0.87 | 13033 |
| 286B5E6 | 0.32 | 8086 | 0.55 | 2487 |
| 286G6A5 | 0.44 | 9773 | 0.53 | 2856 |
| 290F10G10 | 0.38 | 9570 | 0.53 | 2942 |
| 293F10B6 | 0.45 | 8103 | 0.98 | 2254 |
| Reference Ab | 0.27 | 8592 | 0.32 | 2583 |
| hIgG1 Isotype | NA | 106 | NA | 101 |

Example 3. ADCC of Chimeric Abs on LIV-1-Expressing Cells

This example tested the ADCC activities of certain chimeric antibodies.

The ADCC Reporter Bioassay uses an alternative readout at an earlier point in ADCC MOA pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC MOA is quantified through the luciferase produced as a result of NFAT pathway activation; luciferase activity in the effector cell is quantified with luminescence readout. Serial dilutions of chimeric Abs were incubated for 6 hours at 37° C. with engineered Jurkat effector cells (ADCC Bioassay Effector Cells) and ADCC Bioassay target Cells (expressing LIV-1). Luciferase activity was quantified using ONE-Glo™ Luciferase Assay Buffer Reagent.

Figure 2:
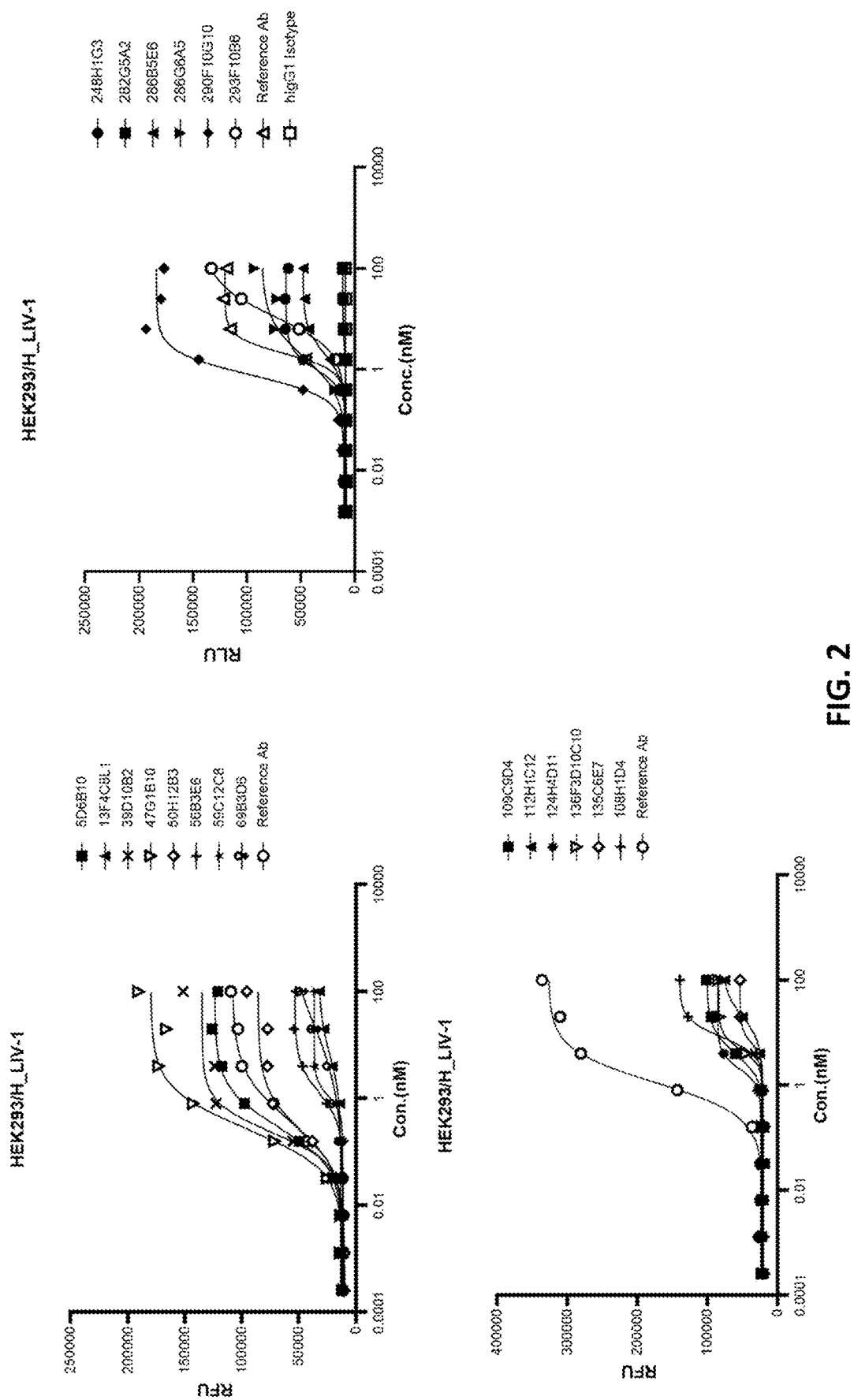
FIG. 2 shows the results of ADCC testing of the tested chimeric antibodies on human LIV-1-expressing cells.

As shown in FIG. 2 and Table 3, many of the tested antibodies exhibited potent ADCC activities.

TABLE 3

ADCC Activities

| Antibody name | $EC_{50}$ (nM) | Top (RFU) |
|---|---|---|
| 5D6B10 | 0.3 | 121246 |
| 13F4C8L1 | 6.7 | 32075 |
| 13F4C8L2 | 52.1 | 42072 |
| 39D10B2 | 0.2 | 151407 |
| 47G1B10 | 0.3 | 190562 |
| 50H12B3 | 0.2 | 95584 |
| 56B3E6 | 1.3 | 52317 |
| 59C12C8 | 1.1 | 36258 |
| 69B3D6 | 25.3 | 47150 |
| Reference Ab | 0.4 | 109598 |
| 109C9D4 | 4.1 | 101482 |
| 112H1C12 | 20.5 | 74698 |
| 124H4D11 | 2.1 | 81886 |
| 136F3D10C10 | 4.8 | 83939 |
| 135C6E7 | 6.4 | 53082 |
| 108H1D4 | 8.3 | 139242 |
| Reference Ab | 1.1 | 336625 |
| 248H1G3 | 0.5 | 61641 |
| 282G5A2 | 1.2 | 11345 |
| 286B5E6 | 1.1 | 47783 |
| 286G6A5 | 0.9 | 93062 |
| 290F10G10 | 0.4 | 176963 |
| 293F10B6 | 7.9 | 132929 |
| Reference Ab | 1.1 | 118626 |
| hIgG1 Isotype | NA | 9347 |

Example 4. Internalization Effect of Chimeric Antibodies

This example tested the internalization activities of certain chimeric antibodies.

Optimal Leads and human IgG1 isotype were conjugated with pHAb dye, which is not fluorescent at neutral pH but becomes highly fluorescent at acidic pH in lysosome with internalization. Human LIV-1 expressing HEK293 engineering cells (HEK293/H_LIV-1) were incubated with Abs-pHdye for 24 hours at 37° C. Cells were washed twice and resuspended in 120 μL of 2% FBS/PBS buffer. Results were measured by Envison. The EC50 was calculated using GraphPad Software (LaJolla, CA).

Figure 3:
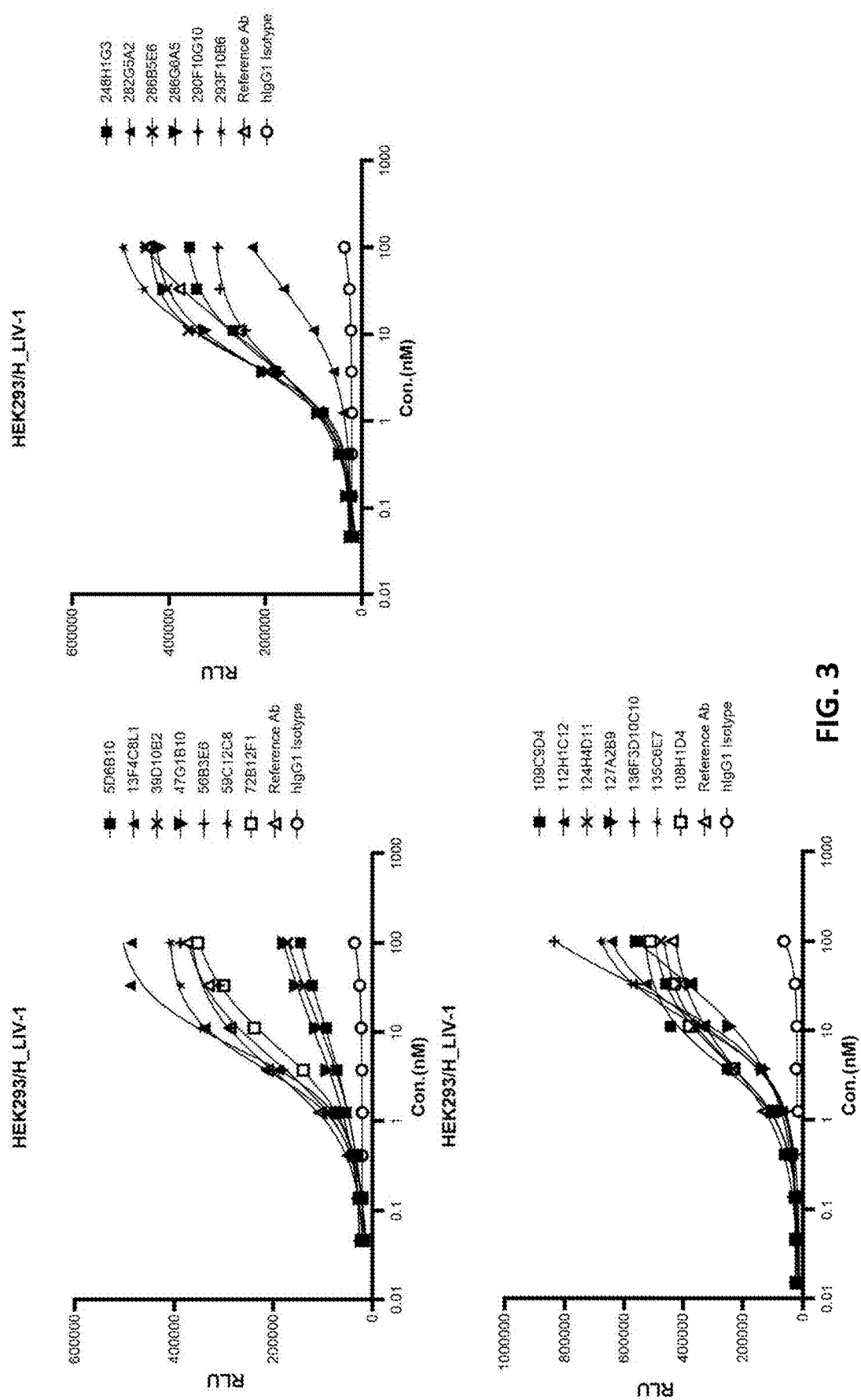

The results are shown in FIG. 3 and Table 4. Most of the tested chimeric antibodies exhibited potent internalization effects.

TABLE 4

Internalization Effect of chimeric Abs

| Antibody name | $EC_{50}$ (nM) | Top (RFU) |
|---|---|---|
| 5D6B10 | 12.7 | 144853 |
| 13F4C8L1 | 6.5 | 487219 |
| 39D10B2 | 16.9 | 170709 |
| 47G1B10 | 10.1 | 178467 |
| 56B3E6 | 5.0 | 387582 |
| 59C12C8 | 3.9 | 408188 |
| 72B12F1 | 7.2 | 352689 |
| Reference Ab | 3.5 | 373629 |
| hIgG1 Isotype | NA | 36521 |
| 109C9D4 | 4.2 | 553762 |
| 112H1C12 | 13.2 | 642671 |
| 124H4D11 | 4.3 | 474386 |
| 127A2B9 | 51.8 | 558283 |
| 136F3D10C10 | 32.2 | 834584 |
| 135C6E7 | 12.4 | 674578 |
| 108H1D4 | 4.8 | 511444 |
| Reference Ab | 3.9 | 435772 |
| hIgG1 Isotype | NA | 63980 |
| 248H1G3 | 4.6 | 357095 |

TABLE 4-continued

| Internalization Effect of chimeric Abs | | |
|---|---|---|
| Antibody name | EC<sub>50</sub> (nM) | Top (RFU) |
| 282G5A2 | 41.2 | 226797 |
| 286B5E6 | 4.6 | 448115 |
| 286G6A5 | 4.6 | 420494 |
| 290F10G10 | 3.5 | 298438 |
| 293F10B6 | 6.1 | 494634 |
| Reference Ab | 11.1 | 446949 |
| hIgG1 Isotype | NA | 36521 |

Example 5. Cytotoxic Activities of Chimeric Antibodies

This example measured the cytotoxic activities of some of the chimeric antibodies.

The human LIV-1 expressing HEK293 engineering cells (HEK293/H_LIV-1) were seeded to a 96-well plate. The cells were treated with chimeric Abs complex (utilize MMAE-labeled IgG directed against the Fc portion of an intact IgG primary antibody to form a labeling complex) at respective concentrations for 5 days. The cell viability was measured by Cell Titer-Glo reagent, and the luciferase activity was detected by Envison. The results indicated that these chimeric Abs have strong killing activity against Human LIV-1 overexpressed cell line.

Figure 4:
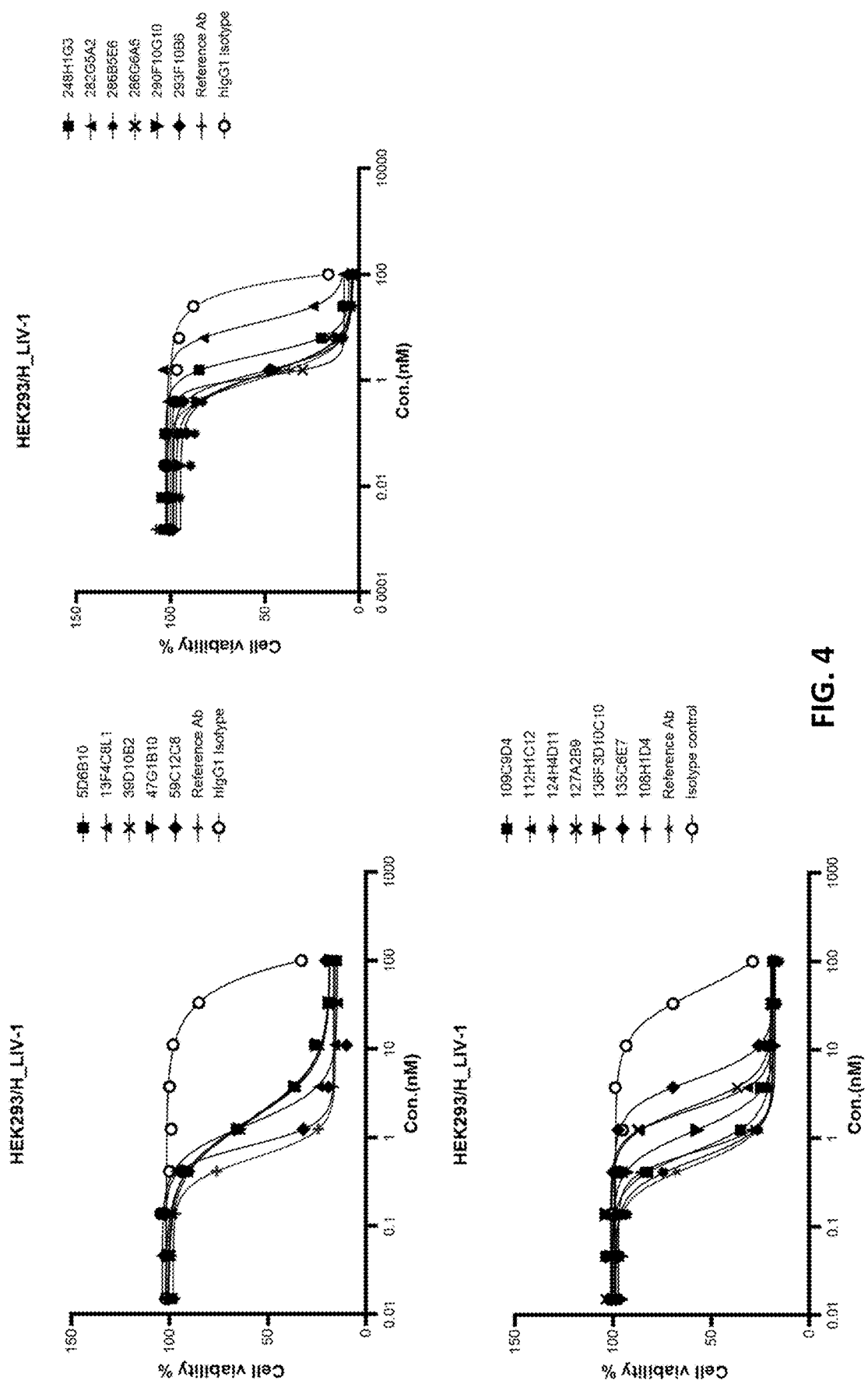
Figure 5A:
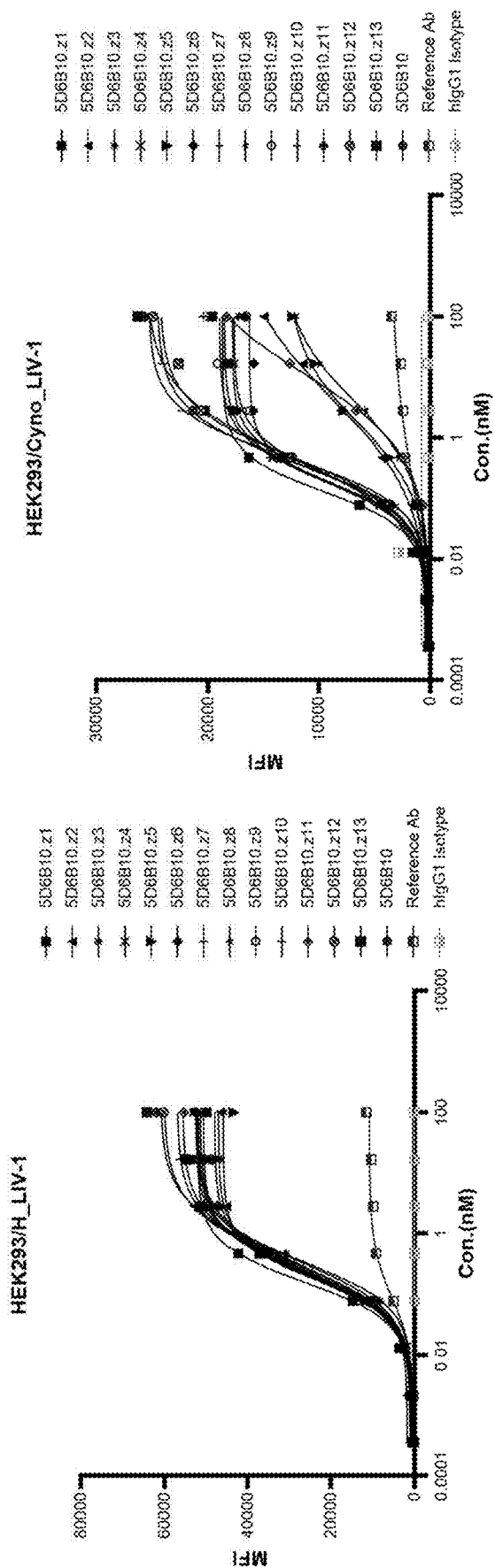
Figure 5B:
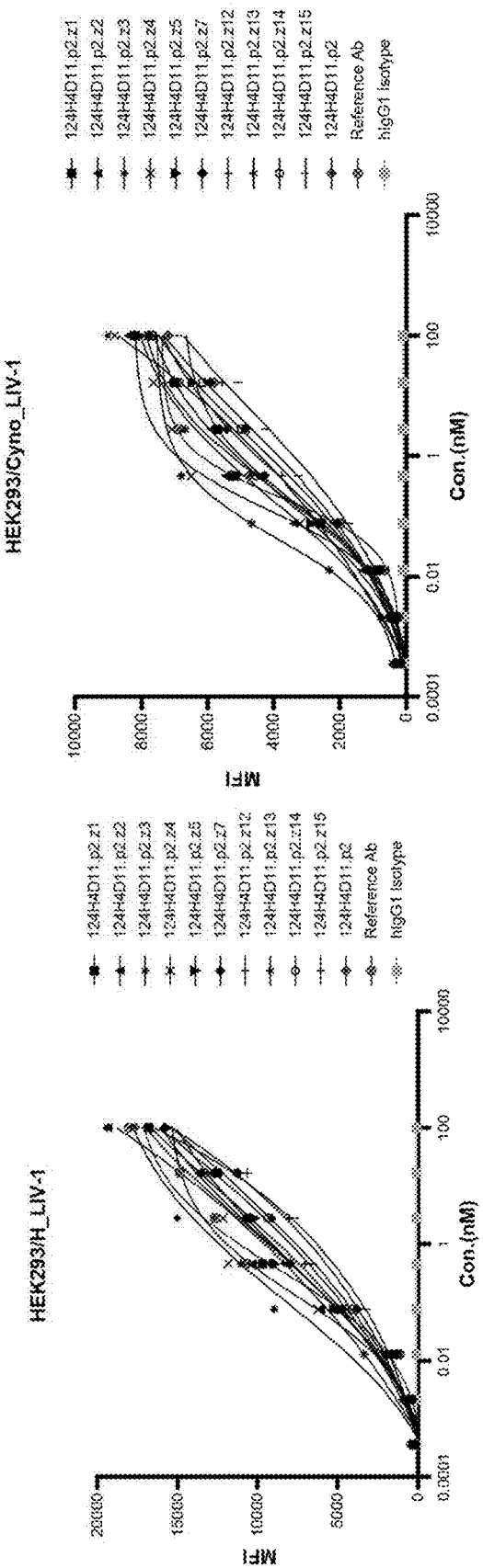
Figure 5C:
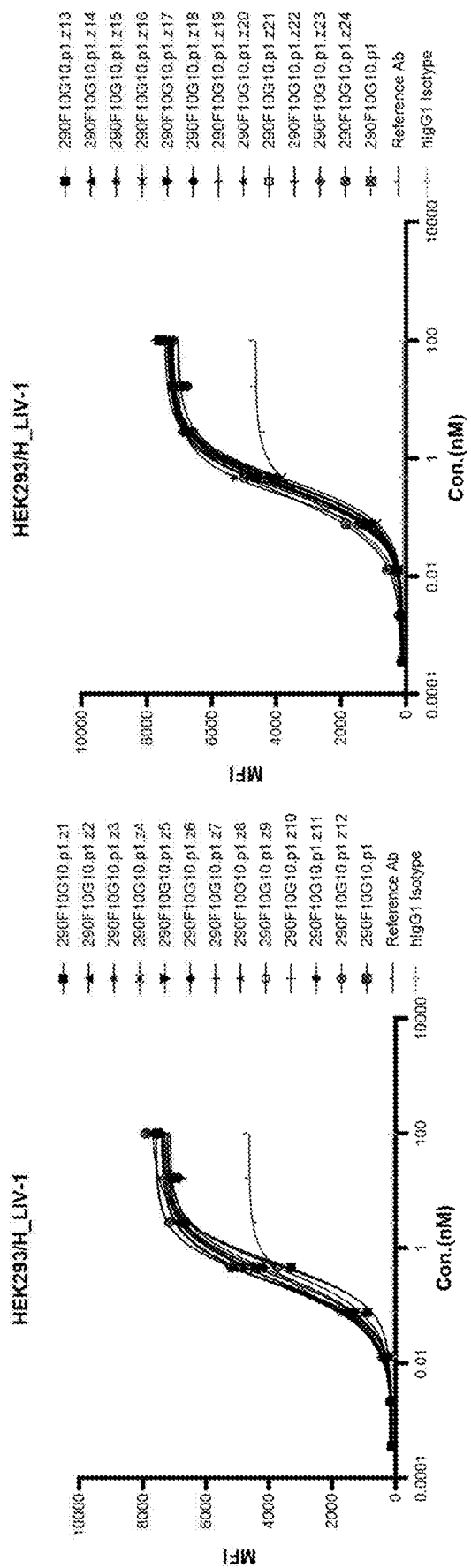
Figure 5D:
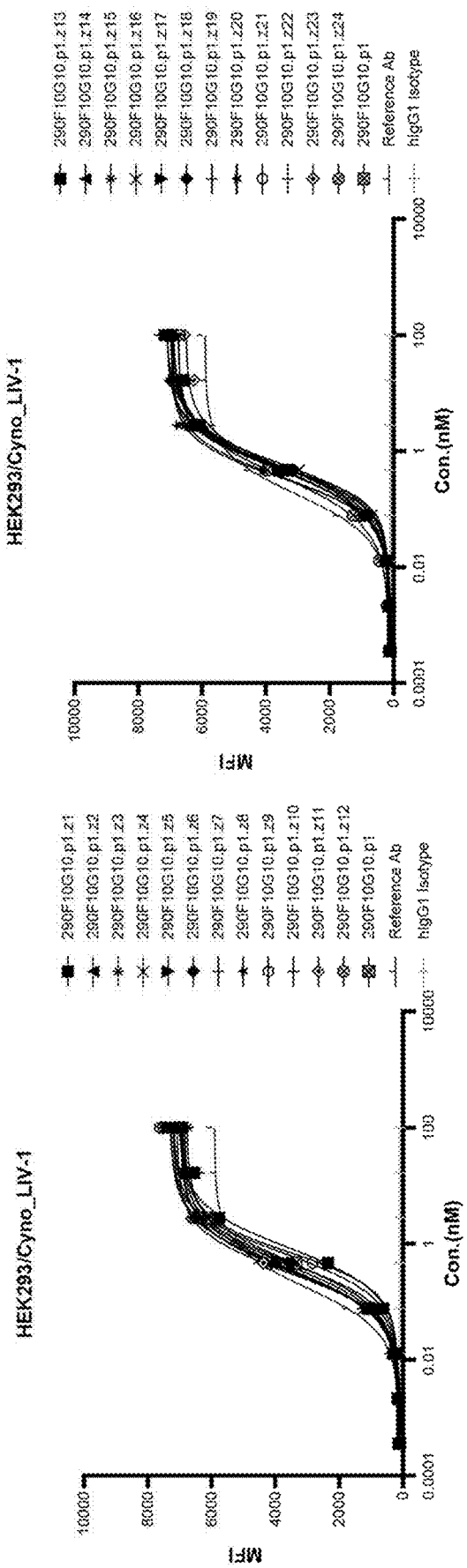

The results are shown in FIG. 4 and Table 5. The tested chimeric antibodies exhibited potent cytotoxic activities.

TABLE 5

| Cytotoxic activities of chimeric Abs | | |
|---|---|---|
| Antibody | IC$_{50}$ (nM) | Cell viability(%) |
| 5D6B10 | 1.55 | 16.38 |
| 13F4C8L1 | 1.42 | 15.14 |
| 39D10B2 | 1.54 | 16.16 |
| 47G1B10 | 1.53 | 17.69 |
| 59C12C8 | 0.81 | 20.32 |
| Reference Ab | 0.59 | 15.59 |
| hIgG1 Isotype | NA | 32.90 |
| 109C9D4 | 0.69 | 18.54 |
| 112H1C12 | 2.08 | 18.03 |
| 124H4D11 | 0.57 | 15.42 |
| 127A2B9 | 2.25 | 17.76 |
| 136F3D10C10 | 1.21 | 16.33 |
| 135C6E7 | 4.60 | 17.56 |
| 108H1D4 | 0.70 | 17.34 |
| Reference Ab | 0.49 | 16.59 |
| hIgG1 Isotype | NA | 29.03 |
| 248H1G3 | 2.99 | 3.31 |
| 282G5A2 | 12.10 | 8.58 |
| 286B5E6 | 1.39 | 4.88 |
| 286G6A5 | 1.15 | 3.74 |
| 290F10G10 | 1.33 | 3.46 |
| 293F10B6 | 1.46 | 3.41 |
| Reference Ab | 1.05 | 2.9 |
| hIgG1 Isotype | NA | 16.43 |

Example 6. Humanization of Lead Chimeric Antibodies

Chimeric antibodies 5D6B10, 124H4D11 and 290F10G10 were selected for humanization.

The variable region genes of each of these antibodies were employed to create humanized MAbs. The amino acid sequences of the VH and VL of MAb were compared against the available database of human Ig gene sequences to find the overall best-matching human germline Ig gene sequences. In addition, potential post-translational modification (PTM) sites (e.g., NG) were mutated (e.g., NG to NA or ND) to reduce PTM risks. The amino acid sequences of the humanized antibodies are listed in Tables 6-8 below.

TABLE 6A

| Humanized sequences-5D6B10 | | |
|---|---|---|
| Antibody chain | Sequence | SEQ ID NO: |
| 5D6B10 VH_2 (3-33) | QVQLVESGGGVVQPGRSLRLSCAVS*GFSLTTYGIH*WVRQAPGKGLEWLA*VIWTGGTTDYNAAFIS*RFTIS<u>K</u>DNS<u>KST</u>LYLQMNSLRAEDTAVYYCAR*GPSSY*WGQGTLVTVSS | 225 |
| 5D6B10 VH_3 (3-33) | QVQLVESGGGVVQPGRSLRLSCTVS*GFSLTTYGIH*WVRQSPGKGLEWLG*VIWTGGTTDYNAAFIS*RLTIS<u>K</u>DNS<u>KST</u>LYFQMNSLR<u>A</u>EDTAVYYCAR*GPSSY*WGQGTLVTVSS | 226 |
| 5D6B10 VH_4 (3-33) | QVQLVQSGGGVVQPGRSLRLSCTVS*GFSLTTYGIH*WVRQSPGKGLEWLG*VIWTGGTTDYNAAFIS*RLTIS<u>K</u>DNS<u>KSTV</u>YFQMNSLQ<u>A</u>EDTAIYYCAR*GPSSY*WGQGTLVTVSS | 227 |
| 5D6B10 VH_2 (4-4) | QVQLQESGPGLVKPSGTLSLTCAVS*GFSLTTYGIH*WVRQSPGKGLEWLG*VIWTGGTTDYNAAFIS*RLTIS<u>K</u>D<u>KS</u>KNQVS<u>LKL</u>SSVT<u>A</u>ADTAVYYCAR*GPSSY*WGQGTLVTVSS | 228 |
| 5D6B10 VH_3 (4-4) | QVQLQQSGPGLVKPSGTLSLTCTVS*GFSLTTYGIH*WVRQSPGKGLEWLG*VIWTGGTTDYNAAFIS*RLTIS<u>K</u>D<u>KS</u>KNQVFFKMSS<u>LT</u>ADTAVYYCAR*GPSSY*WGQGTLVTVSS | 229 |
| 5D6B10 VL_2 | EIVMTQSPATLSVSPGERATLSC*KASQNVDTNVV*WYQQKPGQSPRALIY*SASYRYS*GVPARFSGSGSGTEFTLTISSLQSEDFAVYFCQQ*YNNYPWT*FGQGTKVEIK | 230 |
| 5D6B10 VL_3 | EIVMTQSPATLSVSPGERATVSC*KASQNVDTNVV*WYQQKPGQSPRALIH*SASYRYS*GVPDRFSGSGSGTDFTLTISSLQSEDFAVYFCQQ*YNNYPWT*FGQGTKVEIK | 231 |

TABLE 6A-continued

Humanized sequences-5D6B10

| Antibody chain | Sequence | SEQ ID NO: |
|---|---|---|
| 5D6B10 VL_4 | DIVMTQSPATLSVSPGERVTVSCKAS*QNVDTNVV*WYQQKPGQSPRAL IHSASYRYSGVPDRFSGSGSGTDFTLTISSVQSEDFAVYFC*QQYNNY* *PWT*FGGGTKLEIK | 232 |

TABLE 6B

CDR-5D6B10

| Antibody chain | Sequence | SEQ ID NO: |
|---|---|---|
| 5D6B10 VH | TYGIH | 57 |
|  | VIWTGGTTDYNAAFIS | 58 |
|  | GPSSY | 59 |

TABLE 6B-continued

CDR-5D6B10

| Antibody chain | Sequence | SEQ ID NO: |
|---|---|---|
| 5D6B10 VL | KASQNVDTNVV | 60 |
|  | SASYRYS | 61 |
|  | QQYNNYPWT | 62 |

TABLE 7A

Humanized sequences with PTM sites removed-124H4D11

| Antibody chain | Sequence | SEQ ID NO: |
|---|---|---|
| 124H4D11.p2 VH_2 | QVQLVQSGAEVVKPGASVKVSCKAS*GFNIKDYYMH*WVRQAPGQGLEW IG*WIDPENDDTEYDPKFQ*GRVTMTADTSTSTVYMELSSLRSEDTAVY YCAA*RYYAFDY*WGQGTMVTVSS | 235 |
| 124H4D11.p2 VH_3 | QVPLVQSGAEVVKPGASVKVSCKAS*GFNIKDYYMH*WVRQAPGQGLEW IG*WIDPENDDTEYDPKFQ*GRATMTADTSTSTAYMELSSLRSEDTAVY YCNAR*YYAFDY*WGQGTTVTVSS | 236 |
| 124H4D11.p2 VH_4 | QVPLVQSGAEVVKPGASVKLSCKAS*GFNIKDYYMH*WVKQAPGQGLEW IG*WIDPENDDTEYDPKFQ*GRATMTADTSTSTAYLELSSLRSEDTAVY YCNAR*YYAFDY*WGQGTTVTVSS | 237 |
| 124H4D11.p2 VL_2 (2-30) | DVLMTQSPLSLPVTLGQPASISCR*SSQSIVHSNANTYLE*WYLQRPGQ SPRLLIY*KVSNRFS*GVPDRFSGSGSGTDFTLKISRVEAEDVGVYYCF *QGSQVPPT*FGQGTKLEIK | 238 |
| 124H4D11.p2 VL_3 (2-30) | DVLMTQSPLSLPVTLGQPASISCR*SSQSIVHSNANTYLE*WYLQRPGQ SPKLLIY*KVSNRFS*GVPDRFSGSGSGTEFTLKISRVEAEDLGVYYCF *QGSQVPPT*FGGGTKLEIK | 239 |
| 124H4D11.p2 VL_2 (1-39) | DVQMTQSPSSLSASVGDRVTITCR*SSQSIVHSNANTYLE*WYLQKPGK SPKLLIY*KVSNRFS*GVPDRFSGSGSGTDFTLTISSLQPEDFATYYCF *QGSQVPPT*FGQGTRLEIK | 240 |
| 124H4D11.p2 VL_3 (1-39) | DVLMTQSPSSLSASVGDRVTITCR*SSQSIVHSNANTYLE*WYLQKPGK SPKLLIY*KVSNRFS*GVPDRFSGSGSGTEFTLTISSVQPEDFAVYYCF *QGSQVPPT*FGQGTRLEIK | 241 |
| 124H4D11.p2 VL_4 (1-39) | DVLMTQSPSSLSVSVGDRATISCR*SSQSIVHSNANTYLE*WYLQKPGK SPKLLIY*KVSNRFS*GVPDRFSGSGSGTEFTLTISSVQPEDFGVYYCF *QGSQVPPT*FGGGTRLEIK | 242 |

TABLE 7B

PTM site removed CDR-124H4D11

| Antibody chain | Sequence | SEQ ID NO: |
|---|---|---|
| 124H4D11 VH | DYYMH | 165 |
|  | WIDPENDDTEYDPKFQG | 233 |
|  | RYYAFD$\underline{\text{Y}}$ | 167 |
| 124H4D11 VL | RSSQSIVHSN$\underline{\text{A}}$NTYLE | 234 |
|  | KVSNRFS | 169 |
|  | FQGSQVPPT | 170 |

TABLE 8

Humanized sequences with PTM sites removed-290F10G10

| Antibody chain | Sequence | SEQ ID NO: |
|---|---|---|
| 290F10G10.p1 VH_1 | EVQLVQSGAEVKKPGASVKVSCKASGYTFT*SYWIH*WVRQAPGQGLEWMGT*IYPGD*$\underline{\text{A}}$*DTRSTQKFKD*RVTMTADTSTSTVYMELSSLRSEDTAVYCAR*SLIH*$\underline{\text{DD}}$*$\underline{\text{Y}}$DKYYFDY*WGQGTT$\underline{\text{V}}$TVSS | 244 |
| 290F10G10.p1 VH_2 | EVQLVQSGAEVKKPGASVKVSCKASGYTFT*SYWIH*WVRQAPGQGLEWMGT*IYPGD*$\underline{\text{A}}$*DTRSTQKFKD*RVTVTADKSTSTVYMELSSLRSEDTAVYCAR*SLIH*$\underline{\text{DD}}$*$\underline{\text{Y}}$DKYYFDY*WGQGTT$\underline{\text{V}}$TVSS | 245 |
| 290F10G10.p1 VH_3 | EVQLVQSGAEVKKPGASVKVSCKASGYTFT*SYWIH*WVRQAPGQGLEWIGT*IYPGD*$\underline{\text{A}}$*DTRSTQKFKD*KATVTADKSTSTVYMELSSLRSEDTAVYCAR*SLIH*$\underline{\text{DD}}$*$\underline{\text{Y}}$DKYYFDY*WGQGTT$\underline{\text{V}}$TVSS | 246 |
| 290F10G10.p1 VH_4 | EVQLVQSGAEVKKPGASVKVSCKASGYTFT*SYWIH*WVRQAPGQGLEWMGT*IYPGD*$\underline{\text{A}}$*DTRSTQKFKD*RVTVTADKSTSTVYMELSSLRSEDTAVYCTR*SLIH*$\underline{\text{DD}}$*$\underline{\text{Y}}$DKYYFDY*WGQGTT$\underline{\text{V}}$TVSS | 247 |
| 290F10G10.p1 VH_5 | EVQLVQSGAEVKKPGASVKVSCKASGYTFT*SYWIH*WVRQAPGQGLEWIGT*IYPGD*$\underline{\text{A}}$*DTRSTQKFKD*KATVTADKSTSTVYMELSSLRSEDTAVYCTR*SLIH*$\underline{\text{DD}}$*$\underline{\text{Y}}$DKYYFDY*WGQGTT$\underline{\text{V}}$TVSS | 248 |
| 290F10G10.p1 VH_6 | EIQLVQSGAEVKKPGASVKVSCKASGYTFT*SYWIH*WVRE APGQGLEWIGT*IYPGD*$\underline{\text{A}}$*DTRSTQKFKD*KATVTADKSTSTVYMELSSLRSEDTAVYCTR*SLIH*$\underline{\text{DD}}$*$\underline{\text{Y}}$DKYYFDY*WGQGTT$\underline{\text{V}}$TVSS | 249 |
| 290F10G10.p1 VL_1 | DIQMTQSPSSLSASVGDRVTITC*KARQDINKYIA*WYQQKPGKAPKLLIYY*TSILQP*GVPSRFSGSGSG$\underline{\text{R}}$D$\underline{\text{Y}}$TFTISSLQPEDIATYYC*LQYDYFFT*FGGGTKVEIK | 250 |
| 290F10G10.p1 VL_2 | DIQMTQSPSSLSASVGDRVTITC*KARQDINKYIA*WYQQKPGKAPKLLIHY*TSILQP*GIPSRFSGSGSG$\underline{\text{R}}$D$\underline{\text{Y}}$TFTISSLQPEDIATYYC*LQYDYFFT*FGGGTKVEIK | 251 |
| 290F10G10.p1 VL_3 | DIQMTQSPSSLSASVGDRVTITC*KARQDINKYIA*WYQHKPGKGPKLLIHY*TSILQP*GIPSRFSGSGSG$\underline{\text{R}}$D$\underline{\text{Y}}$TFTISSLQPEDIATYYC*LQYDYFFT*FGGGTKVEIK | 252 |

TABLE 8B

PTM site removed CDR-290F10G10

| Antibody chain | Sequence | SEQ ID NO: |
|---|---|---|
| 290F10G10 VH | SYWIH | 213 |
|  | TIYPGD$\underline{\text{A}}$DTRSTQKFKD | 243 |
|  | SLIHDD$\underline{\text{Y}}$DKYYFDY | 215 |
| 290F10G10 VL | KARQDINKYIA | 216 |
|  | YTSILQP | 217 |
|  | LQYDYFFT | 218 |

The humanized VH and VL genes were produced synthetically and then respectively cloned into vectors containing the human gamma 1 and human kappa constant domains. The pairing of the human VH and the human VL created the humanized antibodies (see Table 9).

TABLE 9A

Humanized antibodies-5D6B10

| VL<br>VH | 5D6B10<br>VL_2 | 5D6B10<br>VL_3 | 5D6B10<br>VL_4 |
|---|---|---|---|
| 5D6B10 VH_2 (3-33) | 5D6B10.Z1 | 5D6B10.Z2 | 5D6B10.Z3 |
| 5D6B10 VH_3 (3-33) | 5D6B10.Z4 | 5D6B10.Z5 | 5D6B10.Z6 |
| 5D6B10 VH_4 (3-33) | 5D6B10.Z7 | 5D6B10.Z8 | 5D6B10.Z9 |
| 5D6B10 VH_2 (4-4) | 5D6B10.Z10 | 5D6B10.Z11 | 5D6B10.Z12 |
| 5D6B10 VH_3 (4-4) | 5D6B10.Z13 | 5D6B10.Z14 | 5D6B10.Z15 |

TABLE 9B

Humanized antibodies-124H4D11.p2

| VL<br>VH | 124H4D11.p2<br>VL_2 (1-39) | 124H4D11.p2<br>VL_3 (1-39) | 124H4D11.p2<br>VL_4 (1-39) | 124H4D11.p2<br>VL_2 (2-30) | 124H4D11.p2<br>VL_3 (2-30) |
|---|---|---|---|---|---|
| 124H4D11.p2 VH_2 | 124H4D11.p2.z1 | 124H4D11.p2.z2 | 124H4D11.p2.z3 | 124H4D11.p2.z4 | 124H4D11.p2.z5 |
| 124H4D11.p2 VH_3 | 124H4D11.p2.z6 | 124H4D11.p2.z7 | 124H4D11.p2.z8 | 124H4D11.p2.z9 | 124H4D11.p2.z10 |
| 124H4D11.p2 VH_4 | 124H4D11.p2.z11 | 124H4D11.p2.z12 | 124H4D11.p2.z13 | 124H4D11.p2.z14 | 124H4D11.p2.z15 |

TABLE 9C

Humanized antibodies-290F10G10.p1

| VH<br>VL | 290F10G10.p1<br>VL_1 | 290F10G10.p1<br>VL_2 | 290F10G10.p1<br>VL_3 |
|---|---|---|---|
| 290F10G10.p1 VH_1 | 290F10G10.p1.Z1 | 290F10G10.p1.Z2 | 290F10G10.p1.Z3 |
| 290F10G10.p1 VH_2 | 290F10G10.p1.Z4 | 290F10G10.p1.Z5 | 290F10G10.p1.Z6 |
| 290F10G10.p1 VH_3 | 290F10G10.p1.Z7 | 290F10G10.p1.Z8 | 290F10G10.p1.Z9 |
| 290F10G10.p1 VH_4 | 290F10G10.p1.Z10 | 290F10G10.p1.Z11 | 290F10G10.p1.Z12 |
| 290F10G10.p1 VH_5 | 290F10G10.p1.Z13 | 290F10G10.p1.Z14 | 290F10G10.p1.Z15 |
| 290F10G10.p1 VH_6 | 290F10G10.p1.Z16 | 290F10G10.p1.Z17 | 290F10G10.p1.Z18 |

Example 7. FACS Binding of Humanized Antibodies to Human LIV-1

In this example, cell based binding of humanized antibodies (hu Abs) on human LIV-1-expressing cells were assessed using flow cytometry.

Cell based binding of hu-Abs on human LIV-1 expressing cells were assessed using flow cytometry. Briefly, the HEK293/H_LIV-1 cells were incubated with hu-Abs (from 100 nM, 6 folds dilution, 8 points). After incubation at 4° C. for 60 minutes, the cells were washed with FACS buffer twice, then stained with fluorescent conjugated secondary antibody at 4° C. for 30 minutes. After that the cells were washed twice and analyzed by flow cytometry.

As shown in FIG. 5A-D and Table 10, the hu-Abs bound to human LIV-1 with high affinity.

TABLE 10

FACS binding of humanized antibodies

| Antibody | HEK293/H_LIV-1 $EC_{50}$ (nM) | HEK293/H_LIV-1 Top (MFI) | HEK293/Cyno_LIV-1 $EC_{50}$ (nM) | HEK293/Cyno_LIV-1 Top (MFI) |
|---|---|---|---|---|
| 5D6B10.z1 | 0.16 | 49847 | 0.13 | 19596 |
| 5D6B10.z2 | 0.18 | 46685 | 4.56 | 14947 |
| 5D6B10.z3 | 0.33 | 51243 | 0.23 | 17243 |
| 5D6B10.z4 | 0.28 | 53014 | 0.20 | 19787 |
| 5D6B10.z5 | 0.17 | 43358 | 1.72 | 12378 |
| 5D6B10.z6 | 0.24 | 52653 | 0.16 | 16697 |
| 5D6B10.z7 | 0.22 | 50675 | 0.19 | 20407 |
| 5D6B10.z8 | 0.19 | 45702 | 4.00 | 12100 |
| 5D6B10.z9 | 0.24 | 52636 | 0.23 | 16533 |
| 5D6B10.z10 | 0.42 | 63801 | 0.47 | 25814 |
| 5D6B10.z11 | 0.29 | 55299 | 11.55 | 18288 |
| 5D6B10.z12 | 0.30 | 60258 | 0.46 | 24945 |
| 5D6B10.z13 | 0.33 | 64301 | 0.50 | 26318 |
| 5D6B10 | 0.29 | 61936 | 0.39 | 25667 |
| Reference Ab | 0.09 | 11647 | 0.21 | 3498 |
| hIgG1 Isotype | NA | 188 | NA | 169 |
| 124H4D11.p2.z1 | 0.89 | 16840 | 0.29 | 8198 |
| 124H4D11.p2.z2 | NA | 19387 | 0.20 | 8393 |
| 124H4D11.p2.z3 | 0.12 | 19390 | 0.04 | 8296 |
| 124H4D11.p2.z4 | 0.13 | 16871 | 0.13 | 8838 |
| 124H4D11.p2.z5 | 0.58 | 15646 | 0.25 | 8070 |
| 124H4D11.p2.z7 | 37.23 | 15844 | 1.48 | 7752 |
| 124H4D11.p2.z12 | NA | 15751 | 3.80 | 7568 |
| 124H4D11.p2.z13 | 7.48 | 17036 | NA | 9028 |
| 124H4D11.p2.z14 | NA | 16783 | 0.50 | 7670 |
| 124H4D11.p2.z15 | NA | 16806 | 5.37 | 6914 |
| 124H4D11.p2 | 1.75 | 17688 | 0.17 | 7197 |
| Reference Ab | 0.37 | 18079 | 0.21 | 7826 |
| hIgG1 Isotype | NA | 118 | NA | 118 |

| Antibody to human LIV-1 | $EC_{50}$ (nM) | Top (MFI) |
|---|---|---|
| 290F10G10.p1.z1 | 0.56 | 7538 |
| 290F10G10.p1.z2 | 0.24 | 7663 |
| 290F10G10.p1.z3 | 0.27 | 7599 |
| 290F10G10.p1.z4 | 0.24 | 7791 |
| 290F10G10.p1.z5 | 0.32 | 7387 |
| 290F10G10.p1.z6 | 0.35 | 7424 |
| 290F10G10.p1.z7 | 0.28 | 7684 |

TABLE 10-continued

| | | |
|---|---|---|
| 290F10G10.p1.z8 | 0.27 | 7545 |
| 290F10G10.p1.z9 | 0.51 | 7945 |
| 290F10G10.p1.z10 | 0.49 | 7292 |
| 290F10G10.p1.z11 | 0.25 | 7822 |
| 290F10G10.p1.z12 | 0.26 | 7924 |
| 290F10G10.p1 | 0.33 | 7530 |
| Reference Ab | 0.13 | 4702 |
| hIgG1 Isotype | NA | 99 |
| 290F10G10.p1.z13 | 0.32 | 7631 |
| 290F10G10.p1.z14 | 0.30 | 7406 |
| 290F10G10.p1.z15 | 0.27 | 7548 |
| 290F10G10.p1.z16 | 0.43 | 7443 |
| 290F10G10.p1.z17 | 0.39 | 7522 |
| 290F10G10.p1.z18 | 0.36 | 7429 |
| 290F10G10.p1.z19 | 0.32 | 7550 |
| 290F10G10.p1.z20 | 0.21 | 7253 |
| 290F10G10.p1.z21 | 0.37 | 7177 |
| 290F10G10.p1.z22 | 0.35 | 7741 |
| 290F10G10.p1.z23 | 0.33 | 7153 |
| 290F10G10.p1.z24 | 0.24 | 7486 |
| 290F10G10.p1 | 0.33 | 7530 |
| Reference Ab | 0.13 | 4702 |
| hIgG1 Isotype | NA | 99 |

| Antibody to cyno LIV-1 | $EC_{50}$ (nM) | Top (MFI) |
|---|---|---|
| 290F10G10.p1.z1 | 0.85 | 7187 |
| 290F10G10.p1.z2 | 0.38 | 7471 |
| 290F10G10.p1.z3 | 0.40 | 6749 |
| 290F10G10.p1.z4 | 0.34 | 7144 |
| 290F10G10.p1.z5 | 0.50 | 7370 |
| 290F10G10.p1.z6 | 0.46 | 6892 |
| 290F10G10.p1.z7 | 0.37 | 7147 |
| 290F10G10.p1.z8 | 0.36 | 7191 |
| 290F10G10.p1.z9 | 0.68 | 7626 |
| 290F10G10.p1.z10 | 0.69 | 6741 |
| 290F10G10.p1.z11 | 0.32 | 7409 |
| 290F10G10.p1.z12 | 0.38 | 7514 |
| 290F10G10.p1 | 0.49 | 6973 |
| Reference Ab | 0.18 | 5983 |
| hIgG1 Isotype | NA | 99 |
| 290F10G10.p1.z13 | 0.46 | 7181 |
| 290F10G10.p1.z14 | 0.48 | 7224 |
| 290F10G10.p1.z15 | 0.36 | 7209 |
| 290F10G10.p1.z16 | 0.61 | 6916 |
| 290F10G10.p1.z17 | 0.51 | 6822 |
| 290F10G10.p1.z18 | 0.56 | 7036 |
| 290F10G10.p1.z19 | 0.48 | 7289 |
| 290F10G10.p1.z20 | 0.35 | 7091 |
| 290F10G10.p1.z21 | 0.51 | 6695 |
| 290F10G10.p1.z22 | 0.57 | 7333 |
| 290F10G10.p1.z23 | 0.49 | 6564 |
| 290F10G10.p1.z24 | 0.37 | 6995 |
| 290F10G10.p1 | 0.49 | 6973 |
| Reference Ab | 0.18 | 5983 |
| hIgG1 Isotype | NA | 99 |

Example 8. Crossreactivity of Humanized Antibodies

Humanized antibodies 5D6B10.z7, 124H4D11.p2.z4 and 290F10G10.p1.z2 were selected for further testing. In this example, FACS cross binding of these selected antibodies to LIV-1 of different species were assessed using flow cytometry.

Cell based binding of optimal leads to different species LIV-1 expressing cells were assessed using flow cytometry. Briefly, the cells were incubated with optimal leads (from 100 nM, 6 folds dilution, 8 points). After incubation at 4° C. for 60 minutes, the cells were washed with 2% FBS/PBS buffer twice, then stained with fluorescent conjugated secondary antibody at 4° C. for 30 minutes. After that the cells were washed twice and resuspended in 80 µL of 2% FBS/PBS buffer. Fluorescent signal of binding was detected using Agilent. The EC50 was calculated using the GraphPad Software (LaJolla, CA).

Figure 6:
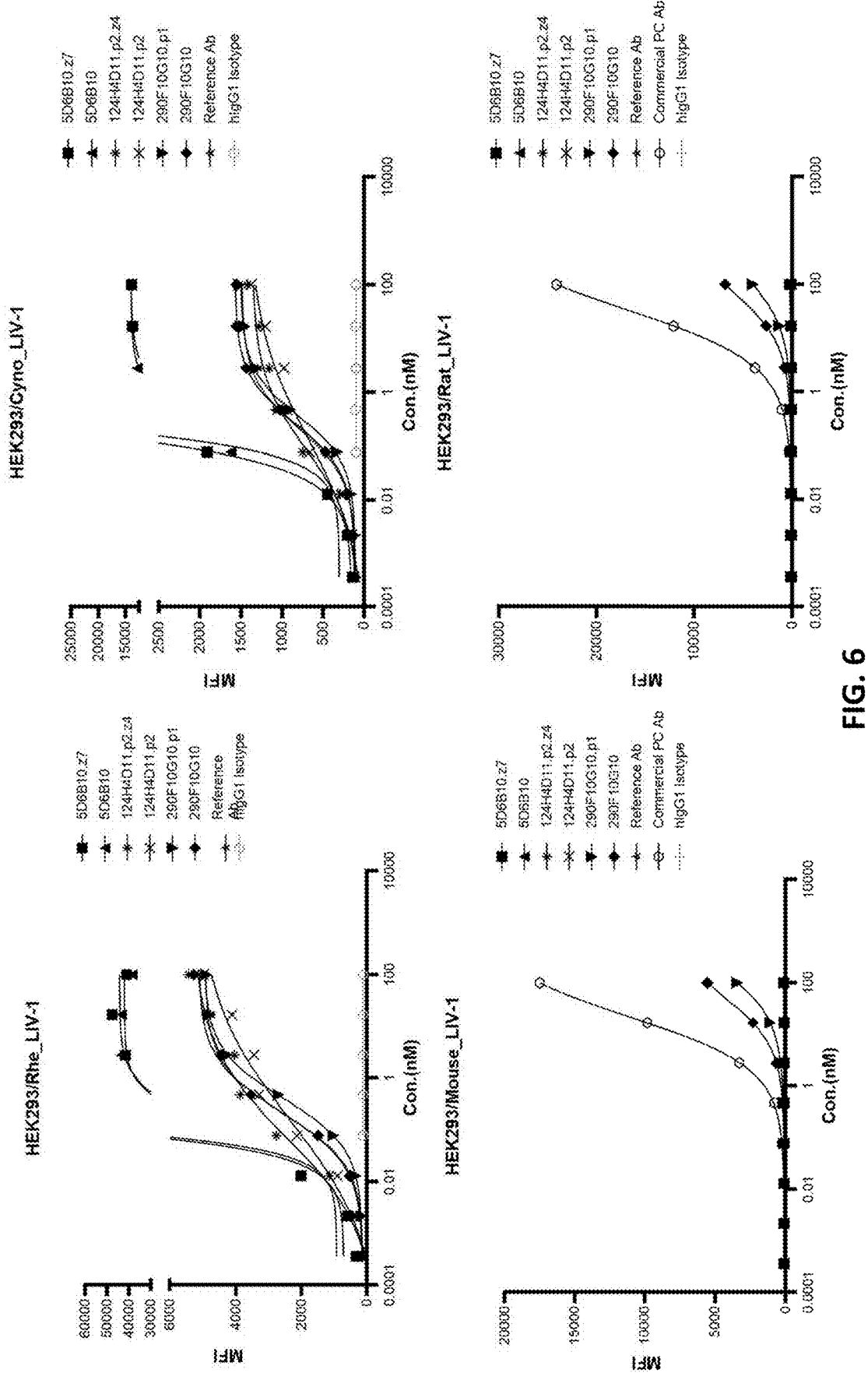

As shown in FIG. 6 and Table 11, the humanized antibodies outperformed the reference antibody in binding to rhesus and cyno LIV-1 but did not bind to mouse or rat LIV-1.

TABLE 11

Cross species binding of humanized antibodies

| | HEK293/Rhe_LIV-1 | | HEK293/Cyno_LIV-1 | |
|---|---|---|---|---|
| Antibody | $EC_{50}$ (nM) | Top (MFI) | $EC_{50}$ (nM) | Top (MFI) |
| 5D6B10.z7 | 0.30 | 41020 | 0.55 | 13946 |
| 5D6B10 | 0.27 | 38377 | 0.53 | 13891 |
| 124H4D11.p2.z4 | 0.07 | 5422 | 0.09 | 1423 |
| 124H4D11.p2 | 0.15 | 4970 | 0.14 | 1381 |
| 290F10G10.p1 | 0.40 | 4895 | 0.36 | 1522 |
| 290F10G10 | 0.22 | 5269 | 0.26 | 1555 |
| Reference Ab | 0.20 | 5108 | 0.21 | 1533 |
| hIgG1 Isotype | NA | 121 | NA | 100 |

| | HEK293/Mouse_LIV-1 | | HEK293/Rat_LIV-1 | |
|---|---|---|---|---|
| Antibody | $EC_{50}$ (nM) | Top (MFI) | $EC_{50}$ (nM) | Top (MFI) |
| 5D6B10.z7 | NA | 162 | NA | 255 |
| 5D6B10 | NA | 121 | NA | 150 |
| 124H4D11.p2.z4 | NA | 107 | NA | 106 |
| 124H4D11.p2 | NA | 107 | NA | 110 |
| 290F10G10.p1 | 359.2 | 3436 | 155.4 | 4038 |
| 290F10G10 | 51.1 | 5550 | 72.23 | 6822 |
| Reference Ab | NA | 114 | NA | 106 |
| Commercial PC Ab | 21.9 | 17511 | 34.26 | 24093 |
| hIgG1 Isotype | NA | 114 | NA | 119 |

Example 9. Internalization Potency of the Humanized Antibodies

This example tested the internalization activities of the humanized antibodies.

The humanized antibodies and human IgG1 isotype were conjugated with pHAb dye, which is not fluorescent at neutral pH but becomes highly fluorescent at acidic pH in lysosome with internalization. HEK293/H_LIV-1 cell lines were incubated with Abs-pH dye for 24 hours and detected fluorescence. Partial leads showed concentration-dependent internalization in both low- and High-expressing H-LIV1-positive cell lines, and HEK293/H_LIV-1 cell line.

Figure 7:
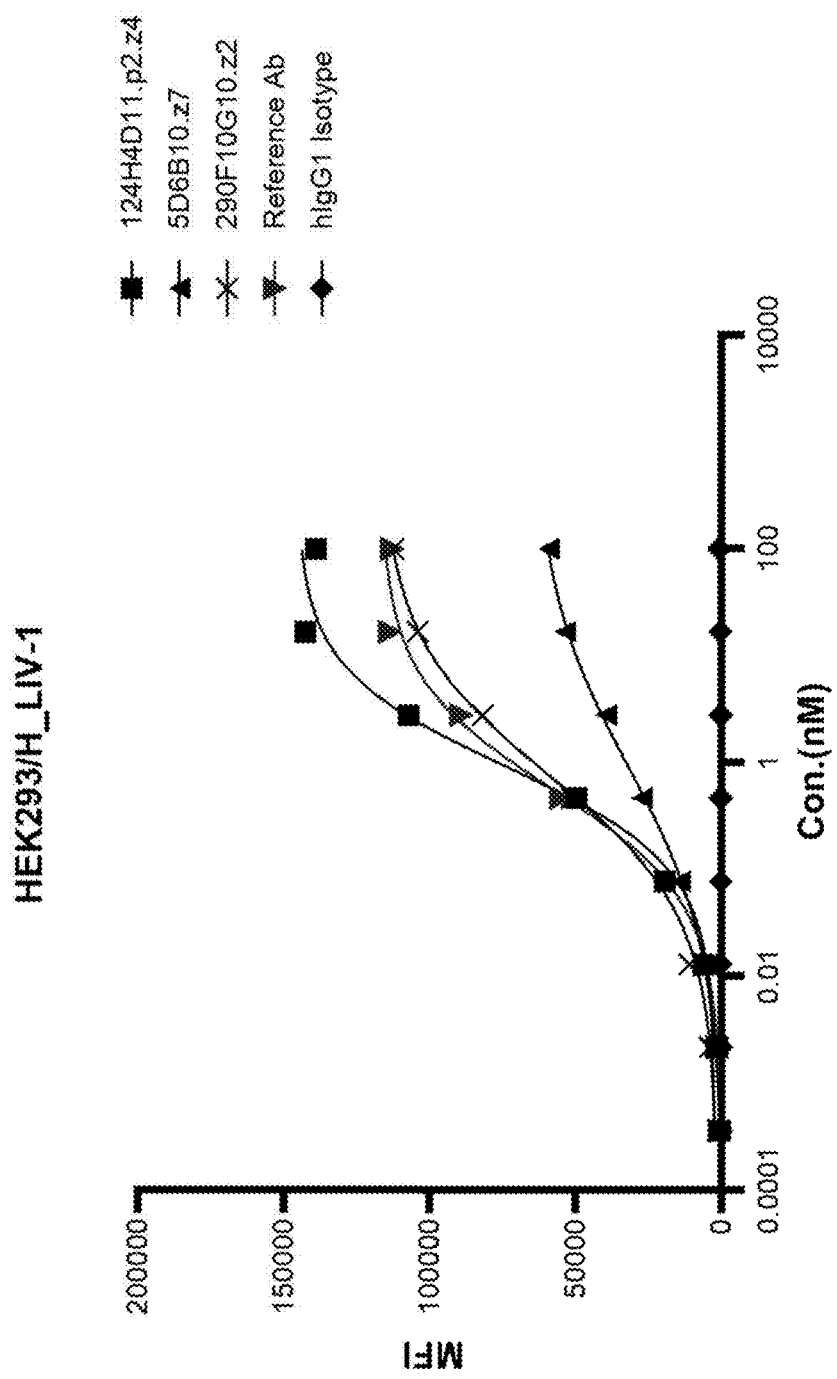

As shown in FIG. 7 and Table 12, all three humanized antibodies showed excellent internalization activity and at least 124H4D11.p2.z4 significantly outperformed the reference antibody.

TABLE 12

Internalization activity of the humanized antibodies

| | HEK293/H_LIV-1 | |
|---|---|---|
| Antibody | $EC_{50}$ (nM) | Top (MFI) |
| 124H4D11.p2.z4 | 5.6 | 139066 |
| 5D6B10.z7 | 5.7 | 59092 |
| 290F10G10.z2 | 5.0 | 112412 |
| Reference Ab | 4.2 | 112973 |
| hIgG1 Isotype | NA | 794 |

Example 10. FACS Binding of Humanized Antibodies and ADC to LIV-1-Overexpressing Cells In this example, FACS binding of the humanized antibodies and their antibody-drug conjugates to high LIV-1 expression human cells were assessed using flow cytometry.

Cell based binding of ADC and naked of ADC on human LIV-1 expressing cells were assessed using flow cytometry. Briefly, HEK293/H_LIV-1, both low- and high-expressing H-LIV1-positive cell lines were incubated with ADC and naked of ADC (from 100 nM, 6 folds dilution, 8 points), respectively. After incubation at 4° C. for 60 minutes, the cells were washed with FACS buffer twice, then stained with fluorescent conjugated secondary antibody at 4° C. for 30 minutes. After that the cells were washed twice and analyzed by flow cytometry. ADC and naked of ADC showed concentration-dependent binding affinity in both low- and High-expressing H-LIV1-positive cell lines and HEK293/H_LIV-1 cell line.

Figure 8:
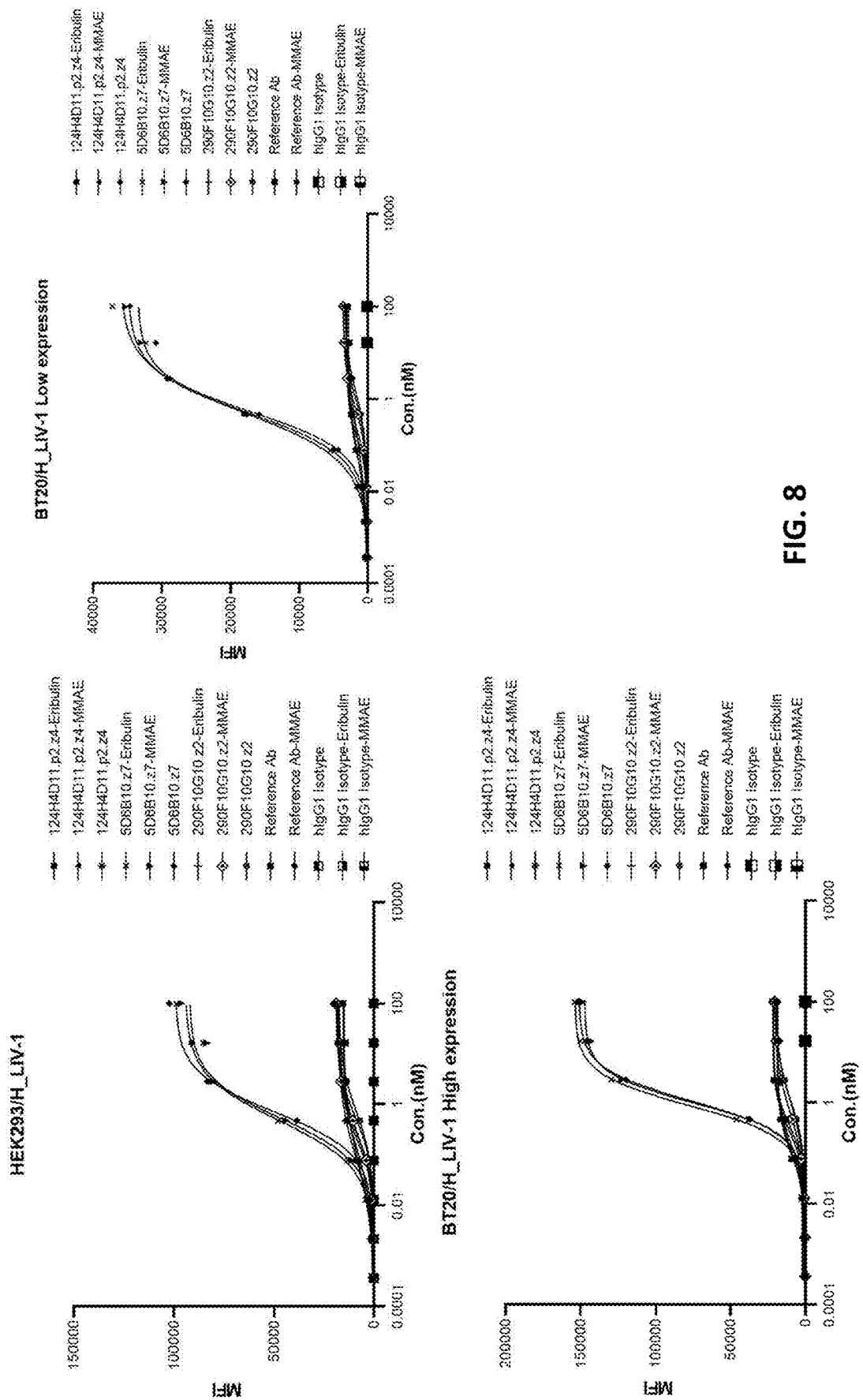

Results of this study (FIG. 8, Table 12) indicated that candidate antibody and reference antibody specific binding with human LIV-1 in a dose-dependent manner, respectively.

TABLE 12

FACS Binding of humanized antibodies and ADC to human LIV-1

| | | 124H4D11.p2.z4-Eribulin | 124H4D11.p2.z4-MMAE | 124H4D11.p2.z4 | 5D6B10.z7-Eribulin | 5D6B10.z7-MMAE | 5D6B10.z7 |
|---|---|---|---|---|---|---|---|
| HEK293/H_LIV-1 | EC50 (nM) | 0.10 | 0.08 | 0.16 | 0.47 | 0.51 | 0.69 |
| | Top (MFI) | 19383 | 20163 | 19888 | 98737 | 96410 | 102252 |
| BT20/H_LIV-1 Low | EC50 (nM) | 0.05 | 0.07 | 0.17 | 0.50 | 0.50 | 0.51 |
| | Top (MFI) | 3098 | 3425 | 3459 | 37196 | 35327 | 34665 |
| BT20/H_LIV-1 High | EC50 (nM) | 0.10 | 0.11 | 0.15 | 0.87 | 0.98 | 1.06 |
| | Top (MFI) | 19225 | 20037 | 20806 | 153933 | 148614 | 151648 |

| | | 290F10G10.z2-Eribulin | 290F10G10.z2-MMAE | 290F10G10.z2 | Reference Ab | Reference Ab-MMAE | hIgG1 Isotype |
|---|---|---|---|---|---|---|---|
| HEK293/H_LIV-1 | EC50 (nM) | 0.55 | 0.34 | 0.70 | 0.21 | 0.17 | NA |
| | Top (MFI) | 18848 | 19051 | 17841 | 15723 | 15757 | 125 |
| BT20/H_LIV-1 Low | EC50 (nM) | 1.14 | 0.68 | 1.43 | 0.18 | 0.15 | NA |
| | Top (MFI) | 3622 | 3568 | 3400 | 2938 | 3279 | 136 |
| BT20/H_LIV-1 High | EC50 (nM) | 1.20 | 0.66 | 1.06 | 0.36 | 0.29 | NA |
| | Top (MFI) | 20982 | 20789 | 18781 | 21856 | 22586 | 133 |

| | | hIgG1 Isotype-Eribulin | hIgG1 Isotype-MMAE |
|---|---|---|---|
| HEK293/H_LIV-1 | EC50 (nM) | NA | NA |
| | Top (MFI) | 143 | 141 |
| BT20/H_LIV-1 Low | EC50 (nM) | NA | NA |
| | Top (MFI) | 161 | 143 |
| BT20/H_LIV-1 High | EC50 (nM) | NA | NA |
| | Top (MFI) | 156 | 145 |

Example 11. Cytotoxic Effect of ADC Towards Human LIV-1-Expressing Cells

This example tested the cytotoxic activity of the tested ADC molecules.

The human LIV-1 expressing HEK293 engineering cells (HEK293/H_LIV-1), and both low- and High-expressing H-LIV1-positive cell lines were seeded to a 96-well plate. The cells were treated with ADC at respective concentrations for 5 days. The cell viability was measured by Cell Titer-Glo reagent, and the luciferase activity was detected by Envison. The results indicated that these ADC have strong killing activity against Human LIV-1 overexpressed cell line.

Figure 9:
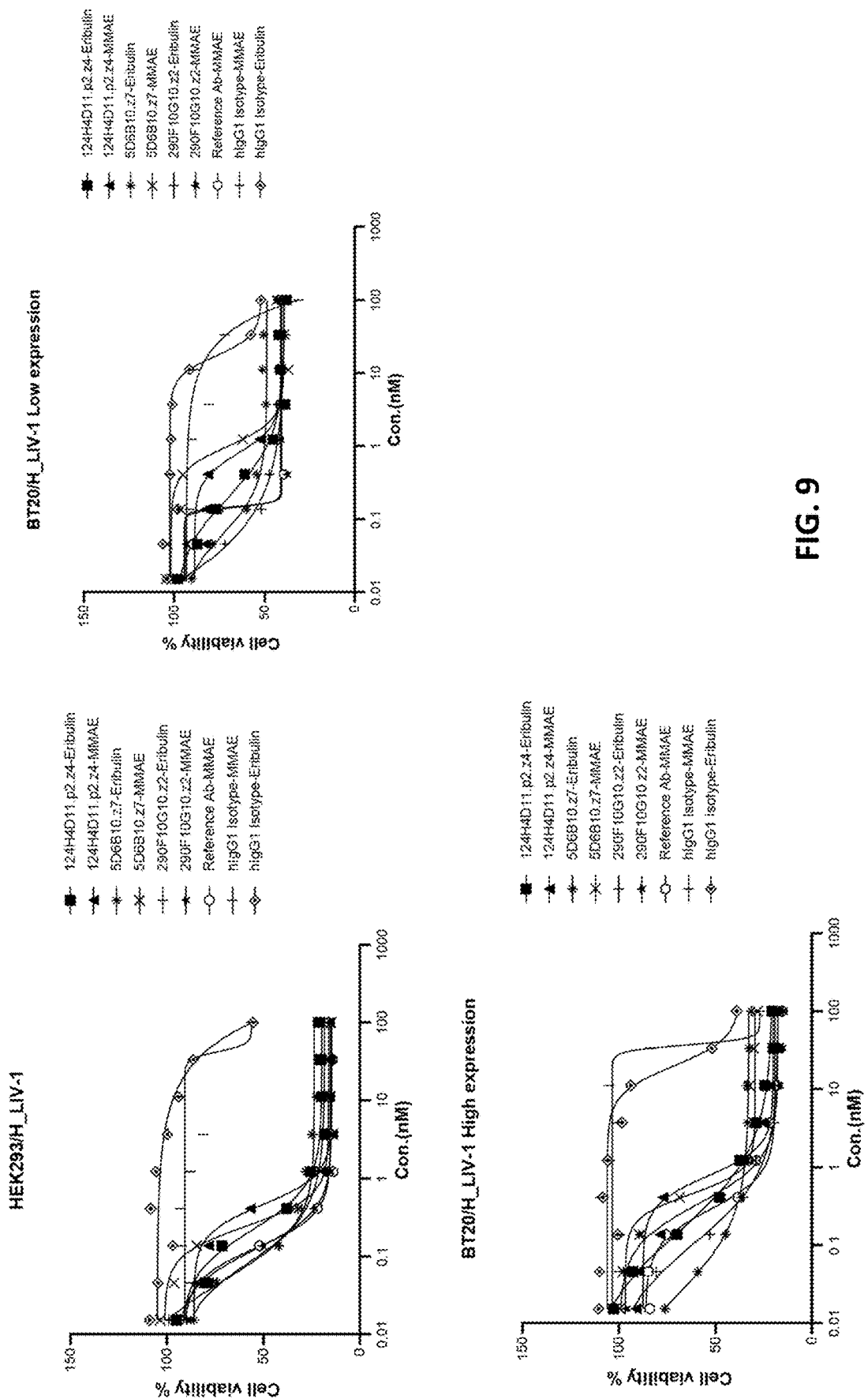
FIG. 9 shows the results of cytotoxic activity testing of the tested ADC molecules.

As shown in FIG. 9 and Table 13, the results indicated that these ADC had strong killing activity against Human LIV-1 overexpressed cell line.

TABLE 13

Cytotoxic activity of the ADC

| | | 124H4D11.p2.z4-Eribulin | 124H4D11.p2.z4-MMAE | 5D6B10.z7-Eribulin | 5D6B10.z7-MMAE | 290F10G10.z2-Eribulin |
|---|---|---|---|---|---|---|
| HEK293/H_LIV-1 | IC50 | 0.22 | 0.46 | 0.08 | 0.25 | 0.05 |
| | Min cell viability % | 21.5 | 15.8 | 21.2 | 15.0 | 18.4 |
| BT20/H_LIV-1 Low | IC50 | 0.21 | 0.79 | 0.06 | 0.98 | 0.01 |
| | Min cell viability % | 37.9 | 40.3 | 42.9 | 43.5 | 38.4 |
| BT20/H_LIV-1 High | IC50 | 0.15 | 0.78 | 0.03 | 0.45 | 0.11 |
| | Min cell viability % | 20.7 | 18.6 | 31.5 | 28.4 | 17.6 |

| | | 290F10G10.z2-MMAE | Reference Ab-MMAE | hIgG1 Isotype-MMAE | hIgG1 Isotype-Eribulin |
|---|---|---|---|---|---|
| HEK293/H_LIV-1 | IC50 | 0.13 | 0.12 | NA | NA |
| | Min cell viability % | 15.3 | 16.2 | 56.3 | 55.4 |
| BT20/H_LIV-1 Low | IC50 | 0.21 | 0.17 | NA | NA |
| | Min cell viability % | 37.9 | 42.2 | 30.9 | 52.3 |
| BT20/H_LIV-1 High | IC50 | 0.34 | 0.29 | NA | NA |
| | Min cell viability % | 14.7 | 15.2 | 27.1 | 39.1 |

Example 12. Cytotoxic Effects of ADCs Towards Human LIV-1 Expressing Cells

This example assessed the cytotoxic effect of candidate ADCs derived from 290F10G10.z2 (LM-001) towards human LIV-1 expressing cells.

LM-001 was conjugated to MMAE or DXD, LM-D01 or LM-D03 (see structures below) and were named LM-001-MMAE, LM-001-DXD, LM-001-LM-D01 or LM-001-LM-D03, respectively. BMK-MMAE, as a benchmark, is an LIV-1-directed ADC derived from an ADC developed by Seagen. The human LIV-1 expressing BT20 engineering cell lines (BT20/H_LIV-1-Low expression and BT20/H_LIV-1-high expression) were seeded to a 96-well plate and treated with ADCs at respective concentrations for 6 days. The cell viability was measured by Cell Titer-Glo reagent, and the luciferase activity was detected by Envison.

(LM-D01)

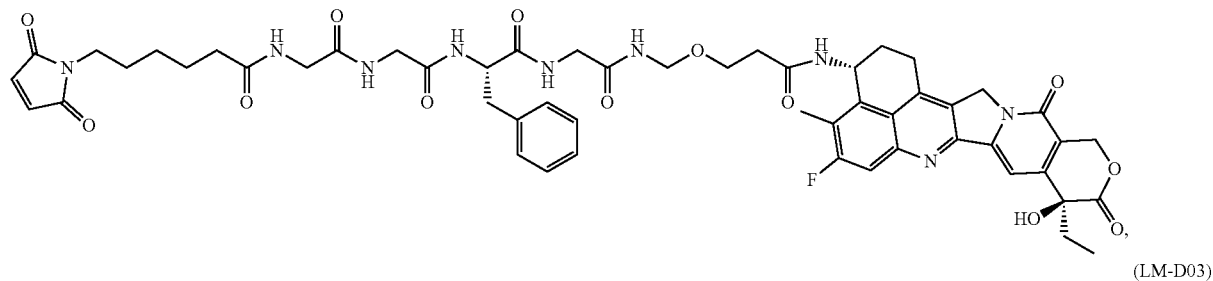

(LM-D03)

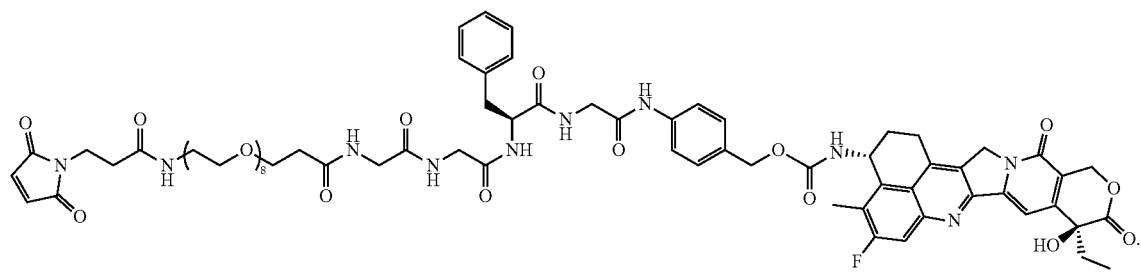

Figure 10:
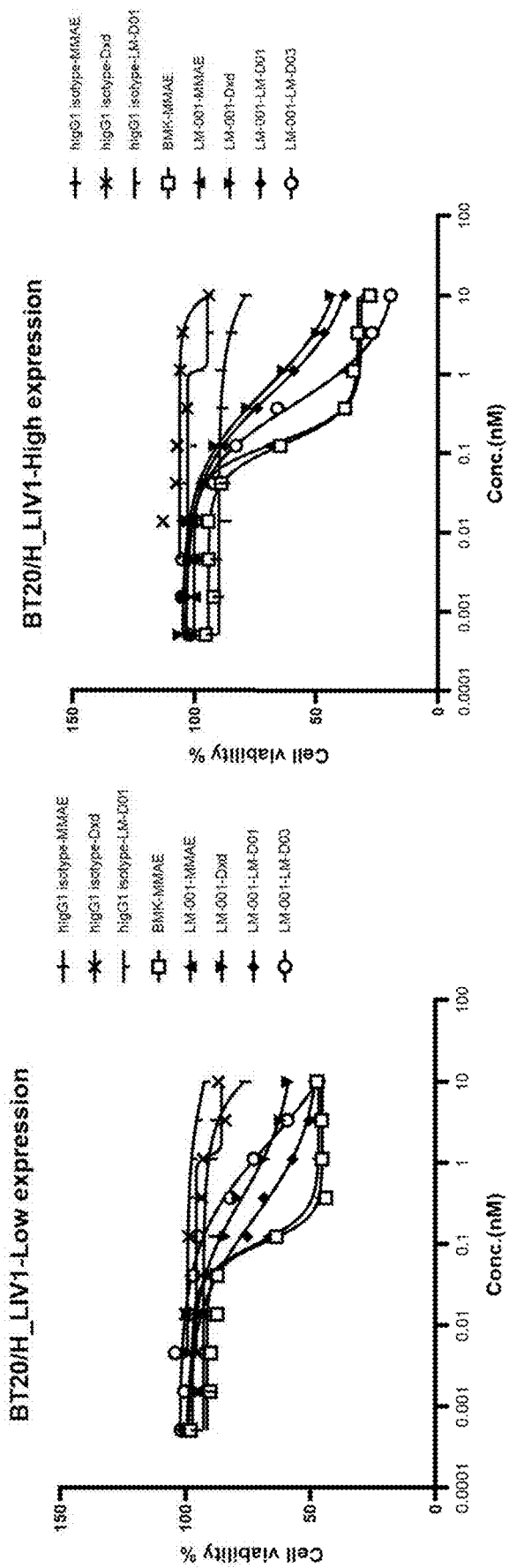
FIG. 10 shows the cytotoxic Effects of the tested ADCs towards human LIV-1-expressing cells.

The results (FIG. 10 and Table 14) show that BMK-MMAE and LM-001-MMAE had comparable killing activity against both low- and High-expressing H-LIV1-positive cell lines. LM-001-LM-D03 exhibited slightly stronger killing activity on BT20/H_LIV-1-high expression cell lines when compared to LM-001-DXD or LM-001-LM-D01.

TABLE 14

Cytotoxic Effects of ADCs

| Ab | BT20/H_LIV1-Low expression | | BT20/H_LIV1-High expression | |
|---|---|---|---|---|
| | $IC_{50}$ | Bottom (% viability) | $IC_{50}$ | Bottom (% viability) |
| BMK-MMAE | 0.10 | 47.31% | 0.13 | 27.74% |
| LM-001-MMAE | 0.10 | 46.76% | 0.13 | 29.11% |
| LM-001-Dxd | 0.38 | 58.92% | 0.65 | 43.70% |
| LM-001-LM-D01 | 0.21 | 48.36% | 0.58 | 37.85% |
| LM-001-LM-D03 | 1.74 | 46.88% | 0.40 | 19.48% |

Example 13. In Vitro Bystander Killing Effects

In this example, condition mediums (CM) were collected from the culture medium of BT20/H_LIV1 expression cell line treated with 0.08, 0.4, 2, and 10 nM ADCs for 6 days, respectively. BT20 cells (H_LIV-1 negative) were cultured with different CM of ADCs for 6 days. The cell viability was evaluated by Cell-Titer-Glo® viability assay kit.

Figure 11:
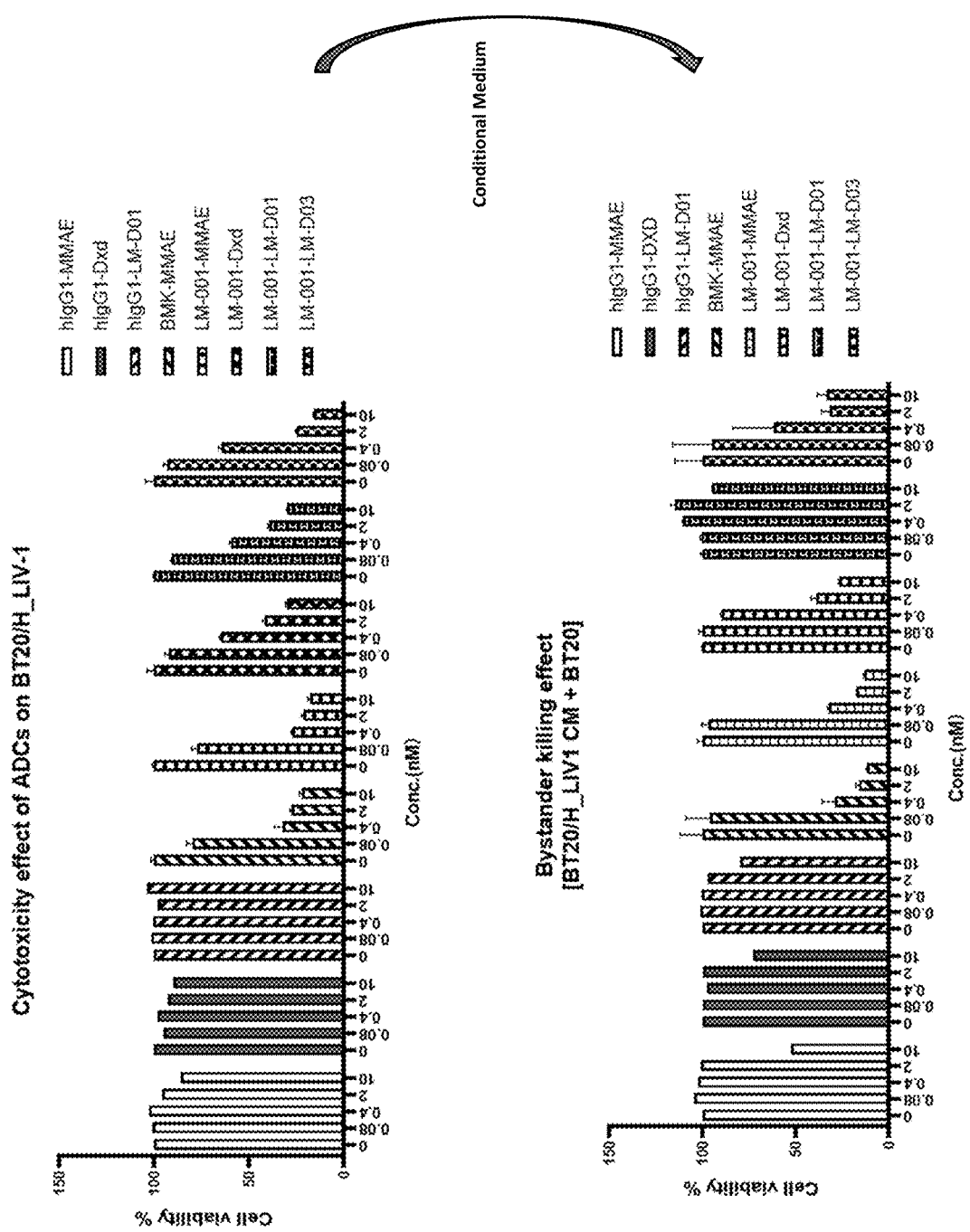
FIG. 11 shows in vitro bystander killing effects.

The results (FIG. 11) indicated that 5 ADCs showed dose-dependent cytotoxicity effect against BT20/H_LIV1 expression cell line. ADCs also showed dose-dependent bystander killing effector on BT20 cell lines except LM-001-Dxd. The bystander killing efficiency of LM-001-LM-D03 was slightly stronger when compared to LM-001-DXD.

Example 14. In Vivo Efficacy of BT20/H_LIV1 Expression CDX Model

This example measured the in vivo efficacy of the ADCs in a BT20/H_LIV1 expression CDX model.

The human LIV-1 expressing BT20 engineering cell lines (BT20/H_LIV-1-expression cell line) was cultivated under standard conditions. For engraftment, 6-8 weeks old female NCG mice were subcutaneously inoculated with $5\times10^6$ into the flank. In advanced treatment study, tumors were grown for 7 days and mice with established tumors of 80~100 mm$^3$ volume were randomized into vehicle and antibody groups before treatment. Animals were injected once i.v. with vehicle or ADCs (3 mg/kg or 6 mg/kg) for 4 weeks. The tumor volume and body weight were monitored twice a week.

Figure 12:
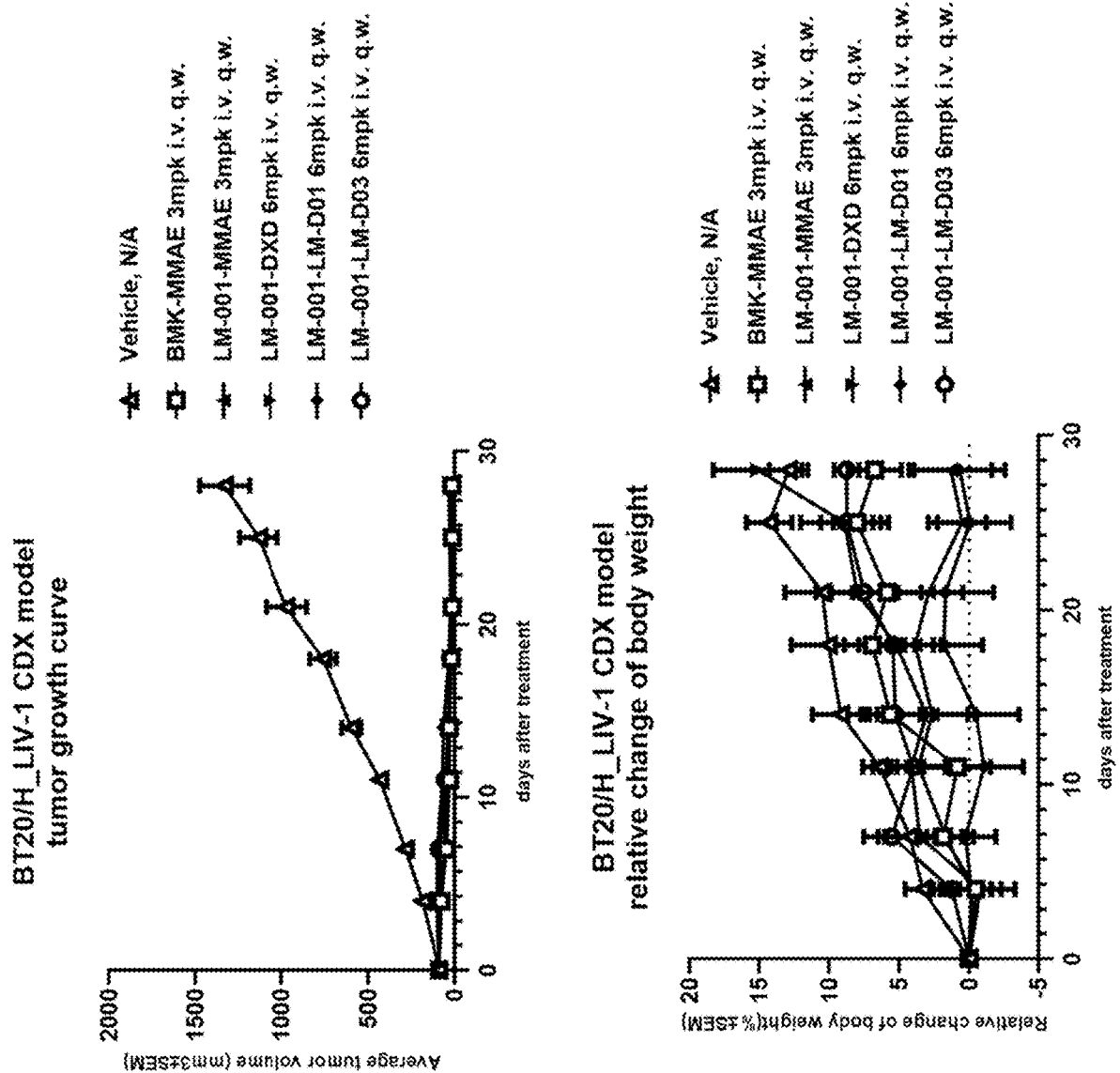
FIG. 12 shows in vivo efficacy of the tested ADCs in a BT20/H_LIV1-expressing CDX model.

The results of this in vivo study (FIG. 12) showed that all five tested ADCs almost completely eradicated tumors in the CDX model of BT20/H_LIV-1-expression cell line.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or antigen-binding fragment thereof that has binding specificity to the human liver receptor homolog 1 (LIV-1) protein, wherein the antibody or the fragment thereof comprises a heavy chain variable region (VH) comprising heavy chain complementarity determining regions (CDR) VH CDR1, VH CDR2, and VH CDR3, and a light chain variable region (VL) comprising VL CDR1, VL CDR2, and VL CDR3, and wherein the VH CDR1, VH CDR2, VH CDR3, VL CDR1, VL CDR2, and VL CDR3, respectively, comprise:
(a) the amino acid sequences of SEQ ID NO:213, 243, 215, 216, 217 and 218;
(b) the amino acid sequences of SEQ ID NO:213-218;
(c) the amino acid sequences of SEQ ID NO:57-62;
(d) the amino acid sequences of SEQ ID NO:165, 233, 167, 234, 169 and 170; or
(e) the amino acid sequences of SEQ ID NO:165-170.

2. The antibody or antigen-binding fragment thereof of claim 1, wherein
the VH CDR1 comprises the amino acid sequence of SEQ ID NO:213,
the VH CDR2 comprises the amino acid sequence of SEQ ID NO:243,
the VH CDR3 comprises the amino acid sequence of SEQ ID NO:215,
the VL CDR1 comprises the amino acid sequence of SEQ ID NO:216,
the VL CDR2 comprises the amino acid sequence of SEQ ID NO:217, and
the VL CDR3 comprises the amino acid sequence of SEQ ID NO:218.

3. The antibody or antigen-binding fragment thereof of claim 2, wherein the VH comprises the amino acid sequence of SEQ ID NO:244, 245, 246, 247, 248, or 249, and the VL comprises the amino acid sequence of SEQ ID NO:250, 251 or 252.

4. The antibody or antigen-binding fragment thereof of claim 2, wherein the VH comprises the amino acid sequence of SEQ ID NO:244, and the VL comprises the amino acid sequence of SEQ ID NO:251.

5. The antibody or antigen-binding fragment thereof of claim 1, wherein the VH CDR1, VH CDR2, VH CDR3, VL CDR1, VL CDR2, and VL CDR3, respective, comprise the amino acid sequences of SEQ ID NO: 213-218.

6. The antibody or antigen-binding fragment thereof of claim 5, wherein the VH comprises the amino acid sequence of SEQ ID NO:53, and the VL comprises the amino acid sequence of SEQ ID NO:54.

7. The antibody or antigen-binding fragment thereof of claim 1, wherein:
the VH CDR1 comprises the amino acid sequence of SEQ ID NO:57,
the VH CDR2 comprises the amino acid sequence of SEQ ID NO:58,
the VH CDR3 comprises the amino acid sequence of SEQ ID NO:59,
the VL CDR1 comprises the amino acid sequence of SEQ ID NO:60,
the VL CDR2 comprises the amino acid sequence of SEQ ID NO:61, and
the VL CDR3 comprises the amino acid sequence of SEQ ID NO:62.

8. The antibody or antigen-binding fragment thereof of claim 7, wherein the VH comprises the amino acid sequence of SEQ ID NO: 1, 225, 226, 227, 228 or 229, and the VL comprises the amino acid sequence of SEQ ID NO:2, 230, 231, or 232.

9. The antibody or antigen-binding fragment thereof of claim 7, wherein the VH comprises the amino acid sequence of SEQ ID NO:227, and the VL comprises the amino acid sequence of SEQ ID NO:230.

10. The antibody or antigen-binding fragment thereof of claim 1, wherein
the VH CDR1 comprises the amino acid sequence of SEQ ID NO:165,
the VH CDR2 comprises the amino acid sequence of SEQ ID NO:233,
the VH CDR3 comprises the amino acid sequence of SEQ ID NO:167,
the VL CDR1 comprises the amino acid sequence of SEQ ID NO:234,
the VL CDR2 comprises the amino acid sequence of SEQ ID NO:169, and
the VL CDR3 comprises the amino acid sequence of SEQ ID NO:170.

11. The antibody or antigen-binding fragment thereof of claim 10, wherein the VH comprises the amino acid sequence of SEQ ID NO:235, 236 or 237, and the VL comprises the amino acid sequence of SEQ ID NO:238, 239, 240, 241 or 242.

12. The antibody or antigen-binding fragment thereof of claim 10, wherein the VH comprises the amino acid sequence of SEQ ID NO:235, and the VL comprises the amino acid sequence of SEQ ID NO:238.

13. The antibody or antigen-binding fragment thereof of claim 1, wherein the VH CDR1, VH CDR2, VH CDR3, VL CDR1, VL CDR2, and VL CDR3, respective, comprise the amino acid sequences of SEQ ID NO:165-170.

14. The antibody or antigen-binding fragment thereof of claim 13, wherein the VH comprises the amino acid sequence of SEQ ID NO:37, and the VL comprises the amino acid sequence of SEQ ID NO:38.

15. One or more polynucleotide(s) encoding the antibody or antigen-binding fragment thereof of claim 1.

16. An antibody-drug conjugate comprising a drug moiety conjugated to the antibody or antigen-binding fragment thereof of claim 1.

17. The antibody-drug conjugate of claim 16, wherein the drug moiety is a maytansinoid, an auristatin, or a macrocyclic ketone.

18. The antibody-drug conjugate of claim 16, wherein the drug moiety is conjugated to the antibody or antigen-binding fragment thereof through a linker.

19. A method of treating cancer in a patient in need thereof, comprising administering to the patient the antibody or antigen-binding fragment thereof of claim 1.

20. The antibody-drug conjugate of claim 18, wherein the drug moiety comprises eribulin, monomethyl auristatin E (MMAE) or monomethyl auristatin F (MMAF), or the drug moiety and the linker collectively comprise (LM-D01)

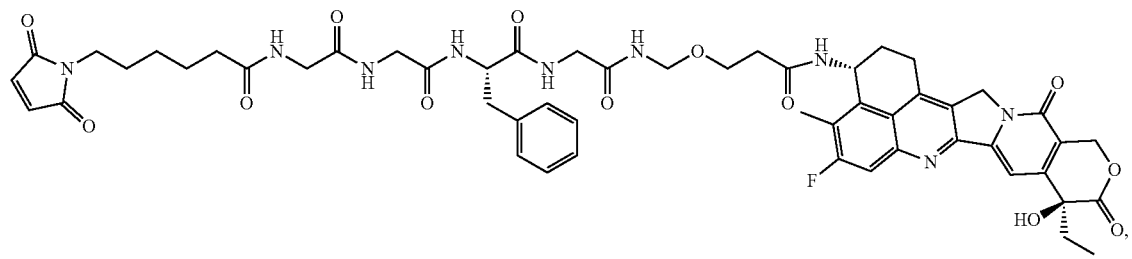

(LM-D02)

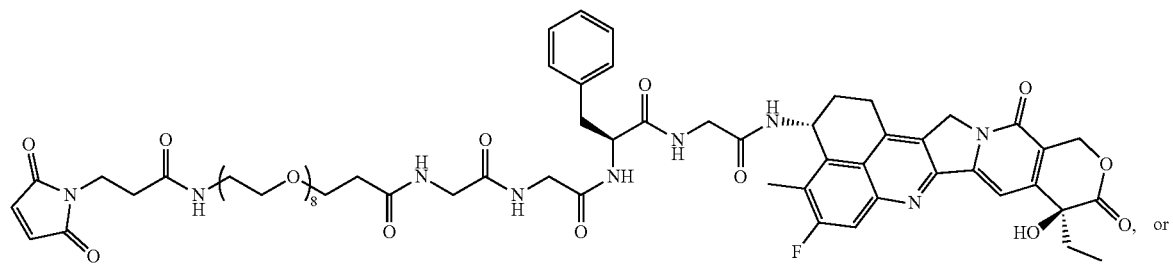

or

-continued
(LM-D03)
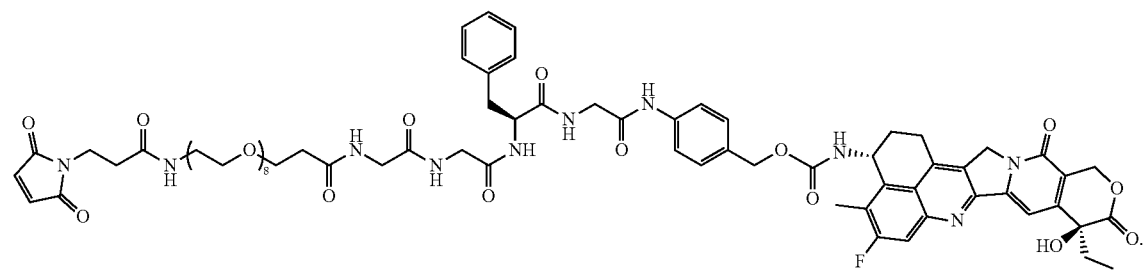
* * * * *

SEQUENCE LISTING

```
Sequence total quantity: 252
SEQ ID NO: 1                  moltype = AA    length = 113
FEATURE                       Location/Qualifiers
source                        1..113
                              mol_type = protein
                              organism = synthetic construct
SEQUENCE: 1
QVQLKQSGPG LVQPSQSLSI TCTVSGFSLT TYGIHWVRQS PGKGLEWLGV IWTGGTTDYN    60
AAFISRLSIS KDNSKSQVFF KMNSLQANDT AIYYCARGPS SYWGQGTLVT VSA           113

SEQ ID NO: 2                  moltype = AA    length = 107
FEATURE                       Location/Qualifiers
source                        1..107
                              mol_type = protein
                              organism = synthetic construct
SEQUENCE: 2
DIVMTQSQKF MSTSVGDRVS VTCKASQNVD TNVVWYQQKP GQSPKALIHS ASYRYSGVPD    60
RFTGSGSGTD FTLTISNVQS EDLAEYFCQQ YNNYPWTFGG GTKLEIK                  107

SEQ ID NO: 3                  moltype = AA    length = 119
FEATURE                       Location/Qualifiers
source                        1..119
                              mol_type = protein
                              organism = synthetic construct
SEQUENCE: 3
QVQLQQPGSE LVRPGASVKL SCKASGYTFT SSWMHWLKQR PGHGLAWIGR IYPGSGSTVY    60
DEKFKSKAIL TVDTSSNTAY MQLSSLTSED SAVYYCTRSM VTAAWFAYWG QGTLVTVSA    119

SEQ ID NO: 4                  moltype = AA    length = 112
FEATURE                       Location/Qualifiers
source                        1..112
                              mol_type = protein
                              organism = synthetic construct
SEQUENCE: 4
DFLMTQTPLS LPVSLGDQAS ISCRSSRSIV HSNGNTYLEW YLQKPGQSPK LLIYKVSNRF    60
SGVPDRFSGS GSGTDFTLKI SRVEAEDLGL YYCFQGSHVP YTFGGGTKLE IK           112

SEQ ID NO: 5                  moltype = AA    length = 113
FEATURE                       Location/Qualifiers
source                        1..113
                              mol_type = protein
                              organism = synthetic construct
SEQUENCE: 5
QVQLKQSGPG LVQPSQSLSI TCTVSGFSLT TYGVHWVRQS PGKGLEWLGV IWTGGTTDYN    60
AAFISRLSIS KDNSKSQVFF KMNSLQANDT AMYYCARGPS SYWGQGTLVT VSA           113

SEQ ID NO: 6                  moltype = AA    length = 107
FEATURE                       Location/Qualifiers
source                        1..107
                              mol_type = protein
                              organism = synthetic construct
SEQUENCE: 6
DIVMTQSQKF MSTSVGDRVS VTCKASQNVD TNVVWYQQKP GQSPKALIHS ASYRYSGVPD    60
RFTGSGSGTD FTLTISNVQS EDLAEYFCQQ YNNYPWTFGG GTKLEIK                  107

SEQ ID NO: 7                  moltype = AA    length = 113
FEATURE                       Location/Qualifiers
source                        1..113
                              mol_type = protein
                              organism = synthetic construct
SEQUENCE: 7
QVQLKQSGPG LVQPSQSLSI TCTVSGFSLT TYGVHWVRQS PGKGLEWLGV IWTGGTTDYN    60
AAFISRLSIS KDNSKSQVFF KMNSLQANDT AIYYCARGPS SYWGQGTLVT VSA           113

SEQ ID NO: 8                  moltype = AA    length = 107
FEATURE                       Location/Qualifiers
source                        1..107
                              mol_type = protein
                              organism = synthetic construct
SEQUENCE: 8
DIVMTQSQKF MSTSVGDRVS VTCKASQNVD TNVVWYQQKP GQSPKALIHS ASYRYSGVPD    60
RFTGSGSGTD FTLTISNVQS EDLAEYFCQQ YNNYPWTFGG GTKLEIK                  107

SEQ ID NO: 9                  moltype = AA    length = 113
FEATURE                       Location/Qualifiers
source                        1..113
                              mol_type = protein
                              organism = synthetic construct
```

```
SEQUENCE: 9
QVQLKQSGPG LVQPSQSLSI TCTVSGFSLT SYGVHWVRQS PGKGLEWLGV IWTGGTTDYN    60
AAFKSRLSIS KDNSKSQVFF KMNSLQANDT AIYYCARGPS SYWGQGTLVT VSA          113

SEQ ID NO: 10           moltype = AA   length = 107
FEATURE                 Location/Qualifiers
source                  1..107
                        mol_type = protein
                        organism = synthetic construct
SEQUENCE: 10
DIVMTQSQKF MSTSVGDRVS VTCKASQNVD TNVVWYQQKP GQSPKALIHS TSYRYSGVPD    60
RFTGSGSGTD FTLTISNVQS EDLAEYFCQQ YNNYPWTFGG GTKLEIK                 107

SEQ ID NO: 11           moltype = AA   length = 118
FEATURE                 Location/Qualifiers
source                  1..118
                        mol_type = protein
                        organism = synthetic construct
SEQUENCE: 11
EVQLQQSGAE LVRSGASVKL SCTASGFNIK DYYIHWVKQR PEQGLEWIGW IDPENDDTEY    60
APKFQGKATM TADTSSNTAY LHLSSLTSED TAVYYCPHGG GFRVFDSWGQ GTTLTVSS     118

SEQ ID NO: 12           moltype = AA   length = 112
FEATURE                 Location/Qualifiers
source                  1..112
                        mol_type = protein
                        organism = synthetic construct
SEQUENCE: 12
DVLMTQTPLS LPVSLGDQAS ISCRSSQDIV HSNGNTYLEW YLQKPGQSPK LLIYKVSNRF    60
SGVPDRFSGS GSGTDFTLKI SRVEAEDLGV YYCFQGSHVP WTFGGGTKLE IK           112

SEQ ID NO: 13           moltype = AA   length = 118
FEATURE                 Location/Qualifiers
source                  1..118
                        mol_type = protein
                        organism = synthetic construct
SEQUENCE: 13
EVQLQQSGAE LVRSGASVKL SCTASDFNIE DYYIHWVKQR PEQGLEWIGW IDPENGDTEY    60
APKFQGKATM TADTSSNTAY LQLSSLTSED TAVYYCPHGG GFRVFDYWGQ GTTLTVSS     118

SEQ ID NO: 14           moltype = AA   length = 112
FEATURE                 Location/Qualifiers
source                  1..112
                        mol_type = protein
                        organism = synthetic construct
SEQUENCE: 14
DVLMTQTPLS LPVSLGDQAS ISCRSSQRIV HSNGNTYLEW YLQKPGQSPK LLIYKVSNRF    60
SGVPDRFSGS GSGTDFTLKI SRVEAEDLGV YYCFQGSHVP WTFGGGTKLE IK           112

SEQ ID NO: 15           moltype = AA   length = 119
FEATURE                 Location/Qualifiers
source                  1..119
                        mol_type = protein
                        organism = synthetic construct
SEQUENCE: 15
QVQLQQSGPE LVKPGASVRI SCKASGYTFT SYHMHWVKQR PGQGLEWIGW IYPGNVKNQS    60
NEKFKGKATL TADKSSSTAY MQLSSLTSED SAVYFCARSD ITRAFFAYWG QGTLVTVSA    119

SEQ ID NO: 16           moltype = AA   length = 112
FEATURE                 Location/Qualifiers
source                  1..112
                        mol_type = protein
                        organism = synthetic construct
SEQUENCE: 16
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSHVP YTFGGGTKLE IK           112

SEQ ID NO: 17           moltype = AA   length = 119
FEATURE                 Location/Qualifiers
source                  1..119
                        mol_type = protein
                        organism = synthetic construct
SEQUENCE: 17
EVQLQQSGAE LVKPGASVKL SCTASGFNIK DTYMHWVKQR PEQGLEWIGR IDPANGNTKN    60
DPRFQGKATI TADTSSNTAY LQLSRLTSED TAVYYCAGGG ITTVVPDHWG QGTTLTVSS    119

SEQ ID NO: 18           moltype = AA   length = 112
FEATURE                 Location/Qualifiers
source                  1..112
```

```
                            mol_type = protein
                            organism = synthetic construct
SEQUENCE: 18
DVVMTQTPLS LPVSLGDQAS ISCRSSQSLV HSNGNTYLQW YLQKPGQSPK LLIYKVSNRF    60
SGVPDRFSGS GSGTDFTLKI SRVEAEDLGV YFCSQSTHVP YTFGGGTKLE IK            112

SEQ ID NO: 19           moltype = AA   length = 118
FEATURE                 Location/Qualifiers
source                  1..118
                        mol_type = protein
                        organism = synthetic construct
SEQUENCE: 19
EVQLQQSGAE LVRSGASVKL SCTASGFNIK DYYMHWVKQR PEQGLEWIGW IDPENGDTEY    60
APKFQGKATL TADTSSNTAY LQLSSLTFED TAVYYCPHGG GLRVFDYWGQ GTSLTVSS     118

SEQ ID NO: 20           moltype = AA   length = 112
FEATURE                 Location/Qualifiers
source                  1..112
                        mol_type = protein
                        organism = synthetic construct
SEQUENCE: 20
DVLMTQIPLS LSVSLGDQAS ISCRSSQSIV HSNGNTYLEW YLQKPGQSPK LLIYKVSNRF    60
SGVPDRFSGS GSGTDFTLKI SRVEAEDLGV YYCFQGSHVP WTFGGGTKLE IK            112

SEQ ID NO: 21           moltype = AA   length = 119
FEATURE                 Location/Qualifiers
source                  1..119
                        mol_type = protein
                        organism = synthetic construct
SEQUENCE: 21
EVQLQQSGAE LVKPGASIKL SCTPSGFNIK DTFIHWVKQR PEQGLEWIGR IDPANGNTRY    60
DPKFQGKATI TADTSSNTAY LQLISLTSED TAVYYCAGGS ISTVVPDYWG QGTTLTVSS    119

SEQ ID NO: 22           moltype = AA   length = 112
FEATURE                 Location/Qualifiers
source                  1..112
                        mol_type = protein
                        organism = synthetic construct
SEQUENCE: 22
DVVVTQTPLS LPVSLGDQAS ISCRSSQSLV HNNGNTYLHW YLQKPGQSPK LLIYKVSNRF    60
SGVPDRFSGS GSGTDFTLKI SRVEAEDLGV YFCSQSTHVP YTFGGGTKLE IK            112

SEQ ID NO: 23           moltype = AA   length = 119
FEATURE                 Location/Qualifiers
source                  1..119
                        mol_type = protein
                        organism = synthetic construct
SEQUENCE: 23
QVQLQQSGPE LVKPGASVRI SCKASGYTFT SYHMHWVKQR PGQGLEWIGW IYPGNVKNQS    60
NEKFKGKATL TADKSSSTAY MHLSSLTSED SAVYFCARSD ITRAFFAYWG QGTLVTVSA    119

SEQ ID NO: 24           moltype = AA   length = 112
FEATURE                 Location/Qualifiers
source                  1..112
                        mol_type = protein
                        organism = synthetic construct
SEQUENCE: 24
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSHGP YTFGGGTKLE IK            112

SEQ ID NO: 25           moltype = AA   length = 118
FEATURE                 Location/Qualifiers
source                  1..118
                        mol_type = protein
                        organism = synthetic construct
SEQUENCE: 25
EVQLQQSGTV LARPGASVKI SCKASGYRFT SYWMHWVKQR PGQGLEWIGA IYPGNSDTTY    60
NQKFKGKAKL TAVTSASTAY MDLSSLTNED SAVYYCTSLL LRSPFDYWGQ GTTLTVSS     118

SEQ ID NO: 26           moltype = AA   length = 112
FEATURE                 Location/Qualifiers
source                  1..112
                        mol_type = protein
                        organism = synthetic construct
SEQUENCE: 26
DVVMTQTPLT LSVTIGQPAS ISCKSSQSLL DSDGKTNLNW LLQRPGQSPK RLIYLVSKLD    60
SGVPDRFTGS GSGTDFTLKI SRVEAEDLGV YYCCQGIQFP RTFGGGTKLE IK            112

SEQ ID NO: 27           moltype = AA   length = 119
```

```
FEATURE                 Location/Qualifiers
source                  1..119
                        mol_type = protein
                        organism = synthetic construct
SEQUENCE: 27
EVQLQQSGTV LARPGASVKM SCKASGYTFI NYWMHWVKQR PGQGLEWIGA FYPGNSDTSY    60
NQKFKDKAKL TAVTSTSTAY MEFSSLTNED SAVYYCTRDF TAVPYFDYWG QGTTLTVSS    119

SEQ ID NO: 28           moltype = AA  length = 112
FEATURE                 Location/Qualifiers
source                  1..112
                        mol_type = protein
                        organism = synthetic construct
SEQUENCE: 28
DILMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSYVP LTFGVGTKLE LK           112

SEQ ID NO: 29           moltype = AA  length = 119
FEATURE                 Location/Qualifiers
source                  1..119
                        mol_type = protein
                        organism = synthetic construct
SEQUENCE: 29
EVQLQQSGTV LARPGTSVKM SCKASGYTFI NYWMHWVRQR PGQGLEWIGA FYPGNSDTSY    60
NQNFKDKAKL TAVTSTSTAY MEFSSLTNED SAVYYCTRDF TAVPFFDYWG QGTTLTVSS    119

SEQ ID NO: 30           moltype = AA  length = 112
FEATURE                 Location/Qualifiers
source                  1..112
                        mol_type = protein
                        organism = synthetic construct
SEQUENCE: 30
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSYVP LTFGVGTKLE LK           112

SEQ ID NO: 31           moltype = AA  length = 119
FEATURE                 Location/Qualifiers
source                  1..119
                        mol_type = protein
                        organism = synthetic construct
SEQUENCE: 31
QVHLQQSGPE LVRPGASVRI SCKASNYTFT SYYLHWVKQR PGQGLEWIGW IYPGNGNTQY    60
NGKFKGQATL TADKSSSTAD IHFSSLTSED SAVYFCARSD ISRAFFAYWG QGTLVTVSA    119

SEQ ID NO: 32           moltype = AA  length = 119
FEATURE                 Location/Qualifiers
source                  1..119
                        mol_type = protein
                        organism = synthetic construct
SEQUENCE: 32
QVHLQQSGPE LVRPGASVRI SCKASNYTFT SYYLHWVKQR PGQGLEWIGW IYPGNGNTQY    60
NGKFKGQATL TADKSSSTAD IHFSSLTSED SAVYFCARSD ISRAFFAYWG QGTLVTVSA    119

SEQ ID NO: 33           moltype = AA  length = 119
FEATURE                 Location/Qualifiers
source                  1..119
                        mol_type = protein
                        organism = synthetic construct
SEQUENCE: 33
EVKLVESGGG LVQPGGSRKL SCAASGFTFS DYGMAWVRQA PGKGPEWVTF ISNLAYSIYY    60
ADTVTGRFTI SRENAKNTLY LEMSSLRSED TAMYYCARVE ENGNYFDYWG QGTTLTVSS    119

SEQ ID NO: 34           moltype = AA  length = 107
FEATURE                 Location/Qualifiers
source                  1..107
                        mol_type = protein
                        organism = synthetic construct
SEQUENCE: 34
DIQMTQTTSS LSASLGDRVT IRCRASQDIG IYLHWYQQKP DGTVKLLIYY TSRLHSGVPS    60
RFSGSRSGTD YSLTIGNLEQ EDIATYFCLQ GNTIPPTFGG GTKLEIK                 107

SEQ ID NO: 35           moltype = AA  length = 119
FEATURE                 Location/Qualifiers
source                  1..119
                        mol_type = protein
                        organism = synthetic construct
SEQUENCE: 35
QVQLQQPGAE LVRPGASVKL SCKASGYTFT SYWMNWVKQR PGQGLKWIGM IDPSNSKTHY    60
NQMFKDKATL TVDKSSNTAY MQLSSLTSED SAVYYCARTS TTMATFAYWG QGTLVSVSA    119
```

```
SEQ ID NO: 36          moltype = AA   length = 112
FEATURE                Location/Qualifiers
source                 1..112
                       mol_type = protein
                       organism = synthetic construct
SEQUENCE: 36
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQASHFP LTFGAGTELD LN           112

SEQ ID NO: 37          moltype = AA   length = 116
FEATURE                Location/Qualifiers
source                 1..116
                       mol_type = protein
                       organism = synthetic construct
SEQUENCE: 37
EVPLQQSGAE LVRSGASVKL SCTASGFNIK DYYMHWVKQR PEQGLEWIGW IDPENGDTEY    60
DPKFQGKATM TADTSSNTAD LQLSSLTSED TAVYYCNARY YAFDYWGQGT TLTVSS       116

SEQ ID NO: 38          moltype = AA   length = 112
FEATURE                Location/Qualifiers
source                 1..112
                       mol_type = protein
                       organism = synthetic construct
SEQUENCE: 38
DVLMTQTPLS LPVSLGDQAS ISCRSSQSIV HSNGNTYLEW YLQKPGQSPK LLIYKVSNRF    60
SGVPDRFSGS GSGTEFTLKI SRVEAEDLGV YYCFQGSQVP PTFGGGTRLE IK           112

SEQ ID NO: 39          moltype = AA   length = 119
FEATURE                Location/Qualifiers
source                 1..119
                       mol_type = protein
                       organism = synthetic construct
SEQUENCE: 39
EVQLQESGPS LVKPSQTLSL TCSVTGDSIT SGYWNWIRKL PGNKLEYMGY ISYSGSTYYN    60
PSLKSRISIT RDTSKNQYYL QLNSVTTEDT ATYYCARIYY DYDGYFDVWG AGTTVTVSS    119

SEQ ID NO: 40          moltype = AA   length = 112
FEATURE                Location/Qualifiers
source                 1..112
                       mol_type = protein
                       organism = synthetic construct
SEQUENCE: 40
DIVMTQAAPS VPVTPGESVS ISCRSSKSLL HSNGNTFLYW FLQRPGQSPQ LLIYRMSNLA    60
SGVPDRFSGS GSGTAFTLRI SRVEAEDVGV YYCMQHLEYP YTFGGGTKLE IK           112

SEQ ID NO: 41          moltype = AA   length = 119
FEATURE                Location/Qualifiers
source                 1..119
                       mol_type = protein
                       organism = synthetic construct
SEQUENCE: 41
QVQLQQSGPE LVKPGASVRI FCKASGYTFT SFHIHWVKQR PGQGLEWIGW IYPGNDNTDH    60
NEKFKGKATL SADKSSSTVY MQLSSLTSED SAVYFCGRSN YYGPLFAYWG QGTLVTVSA    119

SEQ ID NO: 42          moltype = AA   length = 112
FEATURE                Location/Qualifiers
source                 1..112
                       mol_type = protein
                       organism = synthetic construct
SEQUENCE: 42
DILMTQTPLS LPVSLGDQAS ISCRSSQNIV RSNGNTYLEW YLQKPGQSPK VLIYRVSNRF    60
SGVPDRFSGS GSGTDFTLKI SRVEAEDLGV YYCFQGSYVP YTFGGGTKLE IK           112

SEQ ID NO: 43          moltype = AA   length = 121
FEATURE                Location/Qualifiers
source                 1..121
                       mol_type = protein
                       organism = synthetic construct
SEQUENCE: 43
EVQLVESGGG LVQPKGSLKL SCAASGFTFN TYAMNWVRQA PGKGLEWVAR IRSKYNSYAT    60
YYADSVKDRF TISRDDSQSI LYLQMNNLKT EDTAMYYCVR HEDYDGGFAY WGQGTLVTVS   120
A                                                                   121

SEQ ID NO: 44          moltype = AA   length = 113
FEATURE                Location/Qualifiers
source                 1..113
                       mol_type = protein
                       organism = synthetic construct
```

```
SEQUENCE: 44
DIVMSQSPSS LAVSVGEKVT MSCKSSQSLF KSRTRKNYLA WYQQKPGQSP KLLIYWASTR    60
ESGVPDRFTG SGSGTDFTLT ISSVQAEDLA VYYCKESYNL MYTFGGGTKL EIK          113

SEQ ID NO: 45           moltype = AA   length = 124
FEATURE                 Location/Qualifiers
source                  1..124
                        mol_type = protein
                        organism = synthetic construct
SEQUENCE: 45
EVKLVESGGD LVQPGGSRKL SCAASGFTFS DYGMAWFRQA PGKGPEWVAF ISNLAYNIYY    60
ADTVTGRFTI SRENARNTLY LEMSSLRSED TAMYYCAREG GITTVPATDY FDYWGQGTTL   120
TVSS                                                                124

SEQ ID NO: 46           moltype = AA   length = 107
FEATURE                 Location/Qualifiers
source                  1..107
                        mol_type = protein
                        organism = synthetic construct
SEQUENCE: 46
DIQMTQTTSS LSASLGDRVT FSCRASQDIR NYLNWYQQKP DGTVKLLIYY TSRLHSGVPS    60
RFSGSGSGTD YSLTINNLEQ EDLATYFCQQ VNALPLTFGA GTKLELK                 107

SEQ ID NO: 47           moltype = AA   length = 119
FEATURE                 Location/Qualifiers
source                  1..119
                        mol_type = protein
                        organism = synthetic construct
SEQUENCE: 47
EVQLQQSGPE LMKRGASVKI SCKTSTFTFT EFTIHWVKQS HGKSLEWIGG INPNTGGTSY    60
NQNFTGKATL TVDKSSITAY MELRSLTSED SAIYYCAPNW DGYWFFDVWG AGTTVTVSS    119

SEQ ID NO: 48           moltype = AA   length = 107
FEATURE                 Location/Qualifiers
source                  1..107
                        mol_type = protein
                        organism = synthetic construct
SEQUENCE: 48
DIQMTQSPAS LSASVGETVT ITCRASGNIQ NYLAWYQQKQ GKSPQLLVYG AKTLADGVPS    60
RFSGSGSGTQ FSLKINSLQP EDFGSYYCQH FWSPPLTFGA GTKLELK                 107

SEQ ID NO: 49           moltype = AA   length = 118
FEATURE                 Location/Qualifiers
source                  1..118
                        mol_type = protein
                        organism = synthetic construct
SEQUENCE: 49
QVQLQQSGAE LVRPGTSVKV SCKASGYALT KYLIEWIKQR PGQGLEWIGV INPGNAGNNY    60
NEKFKGKATL TVDQSSSTAY MQLSSLTSED SAVYFCARRG RDYAMDNWGQ GTSVTVSS     118

SEQ ID NO: 50           moltype = AA   length = 106
FEATURE                 Location/Qualifiers
source                  1..106
                        mol_type = protein
                        organism = synthetic construct
SEQUENCE: 50
EIVLTQSPAI MSASLGEKVT MSCRASSSIN YIYWYQQKSD ASPKLWIYYT SNLAPGVPAR    60
FSGSGSGNSY SLTISSMEDE DAATYYCQQF TSSPLTFGAG TKLELK                  106

SEQ ID NO: 51           moltype = AA   length = 121
FEATURE                 Location/Qualifiers
source                  1..121
                        mol_type = protein
                        organism = synthetic construct
SEQUENCE: 51
QVTLKESGPG ILQPSQTLSL TCSFSGFSLS TSGMGVSWIR QPSGKGLEWL AHIFWDDDKR    60
YNPSLKSRLT LSKDTSSNQV FLKITSVDTA DTATYYCARR ARHNYPWFPY WGQGTLVTVS   120
A                                                                   121

SEQ ID NO: 52           moltype = AA   length = 111
FEATURE                 Location/Qualifiers
source                  1..111
                        mol_type = protein
                        organism = synthetic construct
SEQUENCE: 52
DIVLTQSPAS LAVSLGQRAT ISCKASQSVD YDGDSYMNWY QQKPGQPPKL LIYAASNLES    60
GIPARFSGSG SGTDFTLNIH PVEEEDAATY YCQQSNEGPY TFGGGTKLEI K             111

SEQ ID NO: 53           moltype = AA   length = 122
```

```
FEATURE                 Location/Qualifiers
source                  1..122
                        mol_type = protein
                        organism = synthetic construct
SEQUENCE: 53
IQLQQSGAEL ARPGASVKLS CKASGYTFTS YWIHWVKERP GQGLEWIGTI YPGDGDTRST    60
QKFKDKATVT AEKSSSTVYM QLSSLASEDS AVYYCTRSLI HDDYDKYYFD YWGQGTTLTV   120
SS                                                                  122

SEQ ID NO: 54           moltype = AA  length = 106
FEATURE                 Location/Qualifiers
source                  1..106
                        mol_type = protein
                        organism = synthetic construct
SEQUENCE: 54
DIQMTQSPSS LSASLGGKVT ITCKARQDIN KYIAWYQHKP GKGPRLLIHY TSILQPGIPS    60
RFSGSGSGRD YSFSISNLEP EDIATYYCLQ YDYFFTFGSG TKLEIK                  106

SEQ ID NO: 55           moltype = AA  length = 121
FEATURE                 Location/Qualifiers
source                  1..121
                        mol_type = protein
                        organism = synthetic construct
SEQUENCE: 55
QVTLKESGPG MLQPSQTLNL TCSFSGFSLN TSGMGVSWIR QPSGKGLEWL AHIFWDDDKR    60
YNPSLKSRLT ISKDVSSNQV FLKITSVDTA DTATYFCARR ARNNYPWFPY WGQGTLVTVS   120
A                                                                   121

SEQ ID NO: 56           moltype = AA  length = 111
FEATURE                 Location/Qualifiers
source                  1..111
                        mol_type = protein
                        organism = synthetic construct
SEQUENCE: 56
DIVLTQSPAS LAVSLGQRAT ISCKASQSVD YDGDSYMNWY QQKPGQPPKL LIYAASNLDS    60
GIPARFSGSG SGTDFTLNIH PMEDEDVATY YCQQSNGAPF TFGGGTKLEI K            111

SEQ ID NO: 57           moltype = AA  length = 5
FEATURE                 Location/Qualifiers
source                  1..5
                        mol_type = protein
                        organism = synthetic construct
SEQUENCE: 57
TYGIH                                                                 5

SEQ ID NO: 58           moltype = AA  length = 16
FEATURE                 Location/Qualifiers
source                  1..16
                        mol_type = protein
                        organism = synthetic construct
SEQUENCE: 58
VIWTGGTTDY NAAFIS                                                    16

SEQ ID NO: 59           moltype = AA  length = 5
FEATURE                 Location/Qualifiers
source                  1..5
                        mol_type = protein
                        organism = synthetic construct
SEQUENCE: 59
GPSSY                                                                 5

SEQ ID NO: 60           moltype = AA  length = 11
FEATURE                 Location/Qualifiers
source                  1..11
                        mol_type = protein
                        organism = synthetic construct
SEQUENCE: 60
KASQNVDTNV V                                                         11

SEQ ID NO: 61           moltype = AA  length = 7
FEATURE                 Location/Qualifiers
source                  1..7
                        mol_type = protein
                        organism = synthetic construct
SEQUENCE: 61
SASYRYS                                                               7

SEQ ID NO: 62           moltype = AA  length = 9
FEATURE                 Location/Qualifiers
```

```
source                    1..9
                          mol_type = protein
                          organism = synthetic construct
SEQUENCE: 62
QQYNNYPWT                                                                        9

SEQ ID NO: 63             moltype = AA   length = 5
FEATURE                   Location/Qualifiers
source                    1..5
                          mol_type = protein
                          organism = synthetic construct
SEQUENCE: 63
SSWMH                                                                            5

SEQ ID NO: 64             moltype = AA   length = 17
FEATURE                   Location/Qualifiers
source                    1..17
                          mol_type = protein
                          organism = synthetic construct
SEQUENCE: 64
RIYPGSGSTV YDEKFKS                                                              17

SEQ ID NO: 65             moltype = AA   length = 10
FEATURE                   Location/Qualifiers
source                    1..10
                          mol_type = protein
                          organism = synthetic construct
SEQUENCE: 65
SMVTAAWFAY                                                                      10

SEQ ID NO: 66             moltype = AA   length = 16
FEATURE                   Location/Qualifiers
source                    1..16
                          mol_type = protein
                          organism = synthetic construct
SEQUENCE: 66
RSSRSIVHSN GNTYLE                                                               16

SEQ ID NO: 67             moltype = AA   length = 7
FEATURE                   Location/Qualifiers
source                    1..7
                          mol_type = protein
                          organism = synthetic construct
SEQUENCE: 67
KVSNRFS                                                                          7

SEQ ID NO: 68             moltype = AA   length = 9
FEATURE                   Location/Qualifiers
source                    1..9
                          mol_type = protein
                          organism = synthetic construct
SEQUENCE: 68
FQGSHVPYT                                                                        9

SEQ ID NO: 69             moltype = AA   length = 5
FEATURE                   Location/Qualifiers
source                    1..5
                          mol_type = protein
                          organism = synthetic construct
SEQUENCE: 69
TYGVH                                                                            5

SEQ ID NO: 70             moltype = AA   length = 16
FEATURE                   Location/Qualifiers
source                    1..16
                          mol_type = protein
                          organism = synthetic construct
SEQUENCE: 70
VIWTGGTTDY NAAFIS                                                               16

SEQ ID NO: 71             moltype = AA   length = 5
FEATURE                   Location/Qualifiers
source                    1..5
                          mol_type = protein
                          organism = synthetic construct
SEQUENCE: 71
GPSSY                                                                            5

SEQ ID NO: 72             moltype = AA   length = 11
```

```
FEATURE                 Location/Qualifiers
source                  1..11
                        mol_type = protein
                        organism = synthetic construct
SEQUENCE: 72
KASQNVDTNV V                                                                11

SEQ ID NO: 73           moltype = AA  length = 7
FEATURE                 Location/Qualifiers
source                  1..7
                        mol_type = protein
                        organism = synthetic construct
SEQUENCE: 73
SASYRYS                                                                      7

SEQ ID NO: 74           moltype = AA  length = 9
FEATURE                 Location/Qualifiers
source                  1..9
                        mol_type = protein
                        organism = synthetic construct
SEQUENCE: 74
QQYNNYPWT                                                                    9

SEQ ID NO: 75           moltype = AA  length = 5
FEATURE                 Location/Qualifiers
source                  1..5
                        mol_type = protein
                        organism = synthetic construct
SEQUENCE: 75
TYGVH                                                                        5

SEQ ID NO: 76           moltype = AA  length = 16
FEATURE                 Location/Qualifiers
source                  1..16
                        mol_type = protein
                        organism = synthetic construct
SEQUENCE: 76
VIWTGGTTDY NAAFIS                                                           16

SEQ ID NO: 77           moltype = AA  length = 5
FEATURE                 Location/Qualifiers
source                  1..5
                        mol_type = protein
                        organism = synthetic construct
SEQUENCE: 77
GPSSY                                                                        5

SEQ ID NO: 78           moltype = AA  length = 11
FEATURE                 Location/Qualifiers
source                  1..11
                        mol_type = protein
                        organism = synthetic construct
SEQUENCE: 78
KASQNVDTNV V                                                                11

SEQ ID NO: 79           moltype = AA  length = 7
FEATURE                 Location/Qualifiers
source                  1..7
                        mol_type = protein
                        organism = synthetic construct
SEQUENCE: 79
SASYRYS                                                                      7

SEQ ID NO: 80           moltype = AA  length = 9
FEATURE                 Location/Qualifiers
source                  1..9
                        mol_type = protein
                        organism = synthetic construct
SEQUENCE: 80
QQYNNYPWT                                                                    9

SEQ ID NO: 81           moltype = AA  length = 5
FEATURE                 Location/Qualifiers
source                  1..5
                        mol_type = protein
                        organism = synthetic construct
SEQUENCE: 81
SYGVH                                                                        5
```

| | | |
|---|---|---|
| SEQ ID NO: 82<br>FEATURE<br>source<br><br>SEQUENCE: 82<br>VIWTGGTTDY NAAFKS | moltype = AA   length = 16<br>Location/Qualifiers<br>1..16<br>mol_type = protein<br>organism = synthetic construct | <br><br><br><br><br>16 |
| SEQ ID NO: 83<br>FEATURE<br>source<br><br>SEQUENCE: 83<br>GPSSY | moltype = AA   length = 5<br>Location/Qualifiers<br>1..5<br>mol_type = protein<br>organism = synthetic construct | <br><br><br><br><br>5 |
| SEQ ID NO: 84<br>FEATURE<br>source<br><br>SEQUENCE: 84<br>KASQNVDTNV V | moltype = AA   length = 11<br>Location/Qualifiers<br>1..11<br>mol_type = protein<br>organism = synthetic construct | <br><br><br><br><br>11 |
| SEQ ID NO: 85<br>FEATURE<br>source<br><br>SEQUENCE: 85<br>STSYRYS | moltype = AA   length = 7<br>Location/Qualifiers<br>1..7<br>mol_type = protein<br>organism = synthetic construct | <br><br><br><br><br>7 |
| SEQ ID NO: 86<br>FEATURE<br>source<br><br>SEQUENCE: 86<br>QQYNNYPWT | moltype = AA   length = 9<br>Location/Qualifiers<br>1..9<br>mol_type = protein<br>organism = synthetic construct | <br><br><br><br><br>9 |
| SEQ ID NO: 87<br>FEATURE<br>source<br><br>SEQUENCE: 87<br>DYYIH | moltype = AA   length = 5<br>Location/Qualifiers<br>1..5<br>mol_type = protein<br>organism = synthetic construct | <br><br><br><br><br>5 |
| SEQ ID NO: 88<br>FEATURE<br>source<br><br>SEQUENCE: 88<br>WIDPENDDTE YAPKFQG | moltype = AA   length = 17<br>Location/Qualifiers<br>1..17<br>mol_type = protein<br>organism = synthetic construct | <br><br><br><br><br>17 |
| SEQ ID NO: 89<br>FEATURE<br>source<br><br>SEQUENCE: 89<br>GGGFRVFDS | moltype = AA   length = 9<br>Location/Qualifiers<br>1..9<br>mol_type = protein<br>organism = synthetic construct | <br><br><br><br><br>9 |
| SEQ ID NO: 90<br>FEATURE<br>source<br><br>SEQUENCE: 90<br>RSSQDIVHSN GNTYLE | moltype = AA   length = 16<br>Location/Qualifiers<br>1..16<br>mol_type = protein<br>organism = synthetic construct | <br><br><br><br><br>16 |
| SEQ ID NO: 91<br>FEATURE<br>source<br><br>SEQUENCE: 91<br>KVSNRFS | moltype = AA   length = 7<br>Location/Qualifiers<br>1..7<br>mol_type = protein<br>organism = synthetic construct | <br><br><br><br><br>7 |

```
SEQ ID NO: 92          moltype = AA   length = 9
FEATURE                Location/Qualifiers
source                 1..9
                       mol_type = protein
                       organism = synthetic construct
SEQUENCE: 92
FQGSHVPWT                                                           9

SEQ ID NO: 93          moltype = AA   length = 5
FEATURE                Location/Qualifiers
source                 1..5
                       mol_type = protein
                       organism = synthetic construct
SEQUENCE: 93
DYYIH                                                               5

SEQ ID NO: 94          moltype = AA   length = 17
FEATURE                Location/Qualifiers
source                 1..17
                       mol_type = protein
                       organism = synthetic construct
SEQUENCE: 94
WIDPENGDTE YAPKFQG                                                  17

SEQ ID NO: 95          moltype = AA   length = 9
FEATURE                Location/Qualifiers
source                 1..9
                       mol_type = protein
                       organism = synthetic construct
SEQUENCE: 95
GGGFRVFDY                                                           9

SEQ ID NO: 96          moltype = AA   length = 16
FEATURE                Location/Qualifiers
source                 1..16
                       mol_type = protein
                       organism = synthetic construct
SEQUENCE: 96
RSSQRIVHSN GNTYLE                                                   16

SEQ ID NO: 97          moltype = AA   length = 7
FEATURE                Location/Qualifiers
source                 1..7
                       mol_type = protein
                       organism = synthetic construct
SEQUENCE: 97
KVSNRFS                                                             7

SEQ ID NO: 98          moltype = AA   length = 9
FEATURE                Location/Qualifiers
source                 1..9
                       mol_type = protein
                       organism = synthetic construct
SEQUENCE: 98
FQGSHVPWT                                                           9

SEQ ID NO: 99          moltype = AA   length = 5
FEATURE                Location/Qualifiers
source                 1..5
                       mol_type = protein
                       organism = synthetic construct
SEQUENCE: 99
SYHMH                                                               5

SEQ ID NO: 100         moltype = AA   length = 17
FEATURE                Location/Qualifiers
source                 1..17
                       mol_type = protein
                       organism = synthetic construct
SEQUENCE: 100
WIYPGNVKNQ SNEKFKG                                                  17

SEQ ID NO: 101         moltype = AA   length = 10
FEATURE                Location/Qualifiers
source                 1..10
                       mol_type = protein
                       organism = synthetic construct
SEQUENCE: 101
```

SDITRAFFAY                                                                              10

SEQ ID NO: 102          moltype = AA  length = 16
FEATURE                 Location/Qualifiers
source                  1..16
                        mol_type = protein
                        organism = synthetic construct SEQUENCE: 102
RSSQSIVHSN GNTYLE                                                                       16

SEQ ID NO: 103          moltype = AA  length = 7
FEATURE                 Location/Qualifiers
source                  1..7
                        mol_type = protein
                        organism = synthetic construct SEQUENCE: 103
KVSNRFS                                                                                 7

SEQ ID NO: 104          moltype = AA  length = 9
FEATURE                 Location/Qualifiers
source                  1..9
                        mol_type = protein
                        organism = synthetic construct SEQUENCE: 104
FQGSHVPYT                                                                               9

SEQ ID NO: 105          moltype = AA  length = 5
FEATURE                 Location/Qualifiers
source                  1..5
                        mol_type = protein
                        organism = synthetic construct SEQUENCE: 105
DTYMH                                                                                   5

SEQ ID NO: 106          moltype = AA  length = 17
FEATURE                 Location/Qualifiers
source                  1..17
                        mol_type = protein
                        organism = synthetic construct SEQUENCE: 106
RIDPANGNTK NDPRFQG                                                                      17

SEQ ID NO: 107          moltype = AA  length = 10
FEATURE                 Location/Qualifiers
source                  1..10
                        mol_type = protein
                        organism = synthetic construct SEQUENCE: 107
GGITTVVPDH                                                                              10

SEQ ID NO: 108          moltype = AA  length = 16
FEATURE                 Location/Qualifiers
source                  1..16
                        mol_type = protein
                        organism = synthetic construct SEQUENCE: 108
RSSQSLVHSN GNTYLQ                                                                       16

SEQ ID NO: 109          moltype = AA  length = 7
FEATURE                 Location/Qualifiers
source                  1..7
                        mol_type = protein
                        organism = synthetic construct SEQUENCE: 109
KVSNRFS                                                                                 7

SEQ ID NO: 110          moltype = AA  length = 9
FEATURE                 Location/Qualifiers
source                  1..9
                        mol_type = protein
                        organism = synthetic construct SEQUENCE: 110
SQSTHVPYT                                                                               9

SEQ ID NO: 111          moltype = AA  length = 5
FEATURE                 Location/Qualifiers
source                  1..5
                        mol_type = protein
                        organism = synthetic construct

```
SEQUENCE: 111
DYYMH                                                                    5

SEQ ID NO: 112          moltype = AA  length = 17
FEATURE                 Location/Qualifiers
source                  1..17
                        mol_type = protein
                        organism = synthetic construct
SEQUENCE: 112
WIDPENGDTE YAPKFQG                                                      17

SEQ ID NO: 113          moltype = AA  length = 9
FEATURE                 Location/Qualifiers
source                  1..9
                        mol_type = protein
                        organism = synthetic construct
SEQUENCE: 113
GGGLRVFDY                                                                9

SEQ ID NO: 114          moltype = AA  length = 16
FEATURE                 Location/Qualifiers
source                  1..16
                        mol_type = protein
                        organism = synthetic construct
SEQUENCE: 114
RSSQSIVHSN GNTYLE                                                       16

SEQ ID NO: 115          moltype = AA  length = 7
FEATURE                 Location/Qualifiers
source                  1..7
                        mol_type = protein
                        organism = synthetic construct
SEQUENCE: 115
KVSNRFS                                                                  7

SEQ ID NO: 116          moltype = AA  length = 9
FEATURE                 Location/Qualifiers
source                  1..9
                        mol_type = protein
                        organism = synthetic construct
SEQUENCE: 116
FQGSHVPWT                                                                9

SEQ ID NO: 117          moltype = AA  length = 5
FEATURE                 Location/Qualifiers
source                  1..5
                        mol_type = protein
                        organism = synthetic construct
SEQUENCE: 117
DTFIH                                                                    5

SEQ ID NO: 118          moltype = AA  length = 17
FEATURE                 Location/Qualifiers
source                  1..17
                        mol_type = protein
                        organism = synthetic construct
SEQUENCE: 118
RIDPANGNTR YDPKFQG                                                      17

SEQ ID NO: 119          moltype = AA  length = 10
FEATURE                 Location/Qualifiers
source                  1..10
                        mol_type = protein
                        organism = synthetic construct
SEQUENCE: 119
GSISTVVPDY                                                              10

SEQ ID NO: 120          moltype = AA  length = 16
FEATURE                 Location/Qualifiers
source                  1..16
                        mol_type = protein
                        organism = synthetic construct
SEQUENCE: 120
RSSQSLVHNN GNTYLH                                                       16

SEQ ID NO: 121          moltype = AA  length = 7
FEATURE                 Location/Qualifiers
source                  1..7
                        mol_type = protein
```

-continued

```
                        organism = synthetic construct
SEQUENCE: 121
KVSNRFS                                                                 7

SEQ ID NO: 122          moltype = AA  length = 9
FEATURE                 Location/Qualifiers
source                  1..9
                        mol_type = protein
                        organism = synthetic construct
SEQUENCE: 122
SQSTHVPYT                                                               9

SEQ ID NO: 123          moltype = AA  length = 5
FEATURE                 Location/Qualifiers
source                  1..5
                        mol_type = protein
                        organism = synthetic construct
SEQUENCE: 123
SYHMH                                                                   5

SEQ ID NO: 124          moltype = AA  length = 17
FEATURE                 Location/Qualifiers
source                  1..17
                        mol_type = protein
                        organism = synthetic construct
SEQUENCE: 124
WIYPGNVKNQ SNEKFKG                                                     17

SEQ ID NO: 125          moltype = AA  length = 10
FEATURE                 Location/Qualifiers
source                  1..10
                        mol_type = protein
                        organism = synthetic construct
SEQUENCE: 125
SDITRAFFAY                                                             10

SEQ ID NO: 126          moltype = AA  length = 16
FEATURE                 Location/Qualifiers
source                  1..16
                        mol_type = protein
                        organism = synthetic construct
SEQUENCE: 126
RSSQSIVHSN GNTYLE                                                      16

SEQ ID NO: 127          moltype = AA  length = 7
FEATURE                 Location/Qualifiers
source                  1..7
                        mol_type = protein
                        organism = synthetic construct
SEQUENCE: 127
KVSNRFS                                                                 7

SEQ ID NO: 128          moltype = AA  length = 9
FEATURE                 Location/Qualifiers
source                  1..9
                        mol_type = protein
                        organism = synthetic construct
SEQUENCE: 128
FQGSHGPYT                                                               9

SEQ ID NO: 129          moltype = AA  length = 5
FEATURE                 Location/Qualifiers
source                  1..5
                        mol_type = protein
                        organism = synthetic construct
SEQUENCE: 129
SYWMH                                                                   5

SEQ ID NO: 130          moltype = AA  length = 17
FEATURE                 Location/Qualifiers
source                  1..17
                        mol_type = protein
                        organism = synthetic construct
SEQUENCE: 130
AIYPGNSDTT YNQKFKG                                                     17

SEQ ID NO: 131          moltype = AA  length = 9
FEATURE                 Location/Qualifiers
source                  1..9
```

```
                        mol_type = protein
                        organism = synthetic construct
SEQUENCE: 131
LLLRSPFDY                                                                        9

SEQ ID NO: 132          moltype = AA   length = 16
FEATURE                 Location/Qualifiers
source                  1..16
                        mol_type = protein
                        organism = synthetic construct
SEQUENCE: 132
KSSQSLLDSD GKTNLN                                                                16

SEQ ID NO: 133          moltype = AA   length = 7
FEATURE                 Location/Qualifiers
source                  1..7
                        mol_type = protein
                        organism = synthetic construct
SEQUENCE: 133
LVSKLDS                                                                          7

SEQ ID NO: 134          moltype = AA   length = 9
FEATURE                 Location/Qualifiers
source                  1..9
                        mol_type = protein
                        organism = synthetic construct
SEQUENCE: 134
CQGIQFPRT                                                                        9

SEQ ID NO: 135          moltype = AA   length = 5
FEATURE                 Location/Qualifiers
source                  1..5
                        mol_type = protein
                        organism = synthetic construct
SEQUENCE: 135
NYWMH                                                                            5

SEQ ID NO: 136          moltype = AA   length = 17
FEATURE                 Location/Qualifiers
source                  1..17
                        mol_type = protein
                        organism = synthetic construct
SEQUENCE: 136
AFYPGNSDTS YNQKFKD                                                               17

SEQ ID NO: 137          moltype = AA   length = 10
FEATURE                 Location/Qualifiers
source                  1..10
                        mol_type = protein
                        organism = synthetic construct
SEQUENCE: 137
DFTAVPYFDY                                                                       10

SEQ ID NO: 138          moltype = AA   length = 16
FEATURE                 Location/Qualifiers
source                  1..16
                        mol_type = protein
                        organism = synthetic construct
SEQUENCE: 138
RSSQSIVHSN GNTYLE                                                                16

SEQ ID NO: 139          moltype = AA   length = 7
FEATURE                 Location/Qualifiers
source                  1..7
                        mol_type = protein
                        organism = synthetic construct
SEQUENCE: 139
KVSNRFS                                                                          7

SEQ ID NO: 140          moltype = AA   length = 9
FEATURE                 Location/Qualifiers
source                  1..9
                        mol_type = protein
                        organism = synthetic construct
SEQUENCE: 140
FQGSYVPLT                                                                        9

SEQ ID NO: 141          moltype = AA   length = 5
FEATURE                 Location/Qualifiers
```

```
source                   1..5
                         mol_type = protein
                         organism = synthetic construct
SEQUENCE: 141
NYWMH                                                                     5

SEQ ID NO: 142           moltype = AA   length = 17
FEATURE                  Location/Qualifiers
source                   1..17
                         mol_type = protein
                         organism = synthetic construct
SEQUENCE: 142
AFYPGNSDTS YNQNFKD                                                        17

SEQ ID NO: 143           moltype = AA   length = 10
FEATURE                  Location/Qualifiers
source                   1..10
                         mol_type = protein
                         organism = synthetic construct
SEQUENCE: 143
DFTAVPFFDY                                                                10

SEQ ID NO: 144           moltype = AA   length = 16
FEATURE                  Location/Qualifiers
source                   1..16
                         mol_type = protein
                         organism = synthetic construct
SEQUENCE: 144
RSSQSIVHSN GNTYLE                                                         16

SEQ ID NO: 145           moltype = AA   length = 7
FEATURE                  Location/Qualifiers
source                   1..7
                         mol_type = protein
                         organism = synthetic construct
SEQUENCE: 145
KVSNRFS                                                                   7

SEQ ID NO: 146           moltype = AA   length = 9
FEATURE                  Location/Qualifiers
source                   1..9
                         mol_type = protein
                         organism = synthetic construct
SEQUENCE: 146
FQGSYVPLT                                                                 9

SEQ ID NO: 147           moltype = AA   length = 5
FEATURE                  Location/Qualifiers
source                   1..5
                         mol_type = protein
                         organism = synthetic construct
SEQUENCE: 147
SYYLH                                                                     5

SEQ ID NO: 148           moltype = AA   length = 17
FEATURE                  Location/Qualifiers
source                   1..17
                         mol_type = protein
                         organism = synthetic construct
SEQUENCE: 148
WIYPGNGNTQ YNGKFKG                                                        17

SEQ ID NO: 149           moltype = AA   length = 10
FEATURE                  Location/Qualifiers
source                   1..10
                         mol_type = protein
                         organism = synthetic construct
SEQUENCE: 149
SDISRAFFAY                                                                10

SEQ ID NO: 150           moltype = AA   length = 5
FEATURE                  Location/Qualifiers
source                   1..5
                         mol_type = protein
                         organism = synthetic construct
SEQUENCE: 150
SYYLH                                                                     5

SEQ ID NO: 151           moltype = AA   length = 17
```

```
FEATURE                 Location/Qualifiers
source                  1..17
                        mol_type = protein
                        organism = synthetic construct
SEQUENCE: 151
WIYPGNGNTQ YNGKFKG                                                      17

SEQ ID NO: 152          moltype = AA  length = 10
FEATURE                 Location/Qualifiers
source                  1..10
                        mol_type = protein
                        organism = synthetic construct
SEQUENCE: 152
SDISRAFFAY                                                              10

SEQ ID NO: 153          moltype = AA  length = 5
FEATURE                 Location/Qualifiers
source                  1..5
                        mol_type = protein
                        organism = synthetic construct
SEQUENCE: 153
DYGMA                                                                    5

SEQ ID NO: 154          moltype = AA  length = 17
FEATURE                 Location/Qualifiers
source                  1..17
                        mol_type = protein
                        organism = synthetic construct
SEQUENCE: 154
FISNLAYSIY YADTVTG                                                      17

SEQ ID NO: 155          moltype = AA  length = 10
FEATURE                 Location/Qualifiers
source                  1..10
                        mol_type = protein
                        organism = synthetic construct
SEQUENCE: 155
VEENGNYFDY                                                              10

SEQ ID NO: 156          moltype = AA  length = 11
FEATURE                 Location/Qualifiers
source                  1..11
                        mol_type = protein
                        organism = synthetic construct
SEQUENCE: 156
RASQDIGIYL H                                                            11

SEQ ID NO: 157          moltype = AA  length = 7
FEATURE                 Location/Qualifiers
source                  1..7
                        mol_type = protein
                        organism = synthetic construct
SEQUENCE: 157
YTSRLHS                                                                  7

SEQ ID NO: 158          moltype = AA  length = 9
FEATURE                 Location/Qualifiers
source                  1..9
                        mol_type = protein
                        organism = synthetic construct
SEQUENCE: 158
LQGNTIPPT                                                                9

SEQ ID NO: 159          moltype = AA  length = 5
FEATURE                 Location/Qualifiers
source                  1..5
                        mol_type = protein
                        organism = synthetic construct
SEQUENCE: 159
SYWMN                                                                    5

SEQ ID NO: 160          moltype = AA  length = 17
FEATURE                 Location/Qualifiers
source                  1..17
                        mol_type = protein
                        organism = synthetic construct
SEQUENCE: 160
MIDPSNSKTH YNQMFKD                                                      17
```

```
SEQ ID NO: 161           moltype = AA   length = 10
FEATURE                  Location/Qualifiers
source                   1..10
                         mol_type = protein
                         organism = synthetic construct
SEQUENCE: 161
TSTTMATFAY                                                                 10

SEQ ID NO: 162           moltype = AA   length = 16
FEATURE                  Location/Qualifiers
source                   1..16
                         mol_type = protein
                         organism = synthetic construct
SEQUENCE: 162
RSSQSIVHSN GNTYLE                                                          16

SEQ ID NO: 163           moltype = AA   length = 7
FEATURE                  Location/Qualifiers
source                   1..7
                         mol_type = protein
                         organism = synthetic construct
SEQUENCE: 163
KVSNRFS                                                                     7

SEQ ID NO: 164           moltype = AA   length = 9
FEATURE                  Location/Qualifiers
source                   1..9
                         mol_type = protein
                         organism = synthetic construct
SEQUENCE: 164
FQASHFPLT                                                                   9

SEQ ID NO: 165           moltype = AA   length = 5
FEATURE                  Location/Qualifiers
source                   1..5
                         mol_type = protein
                         organism = synthetic construct
SEQUENCE: 165
DYYMH                                                                       5

SEQ ID NO: 166           moltype = AA   length = 17
FEATURE                  Location/Qualifiers
source                   1..17
                         mol_type = protein
                         organism = synthetic construct
SEQUENCE: 166
WIDPENGDTE YDPKFQG                                                         17

SEQ ID NO: 167           moltype = AA   length = 7
FEATURE                  Location/Qualifiers
source                   1..7
                         mol_type = protein
                         organism = synthetic construct
SEQUENCE: 167
RYYAFDY                                                                     7

SEQ ID NO: 168           moltype = AA   length = 16
FEATURE                  Location/Qualifiers
source                   1..16
                         mol_type = protein
                         organism = synthetic construct
SEQUENCE: 168
RSSQSIVHSN GNTYLE                                                          16

SEQ ID NO: 169           moltype = AA   length = 7
FEATURE                  Location/Qualifiers
source                   1..7
                         mol_type = protein
                         organism = synthetic construct
SEQUENCE: 169
KVSNRFS                                                                     7

SEQ ID NO: 170           moltype = AA   length = 9
FEATURE                  Location/Qualifiers
source                   1..9
                         mol_type = protein
                         organism = synthetic construct
SEQUENCE: 170
FQGSQVPPT                                                                   9
```

```
SEQ ID NO: 171            moltype = AA   length = 5
FEATURE                   Location/Qualifiers
source                    1..5
                          mol_type = protein
                          organism = synthetic construct
SEQUENCE: 171
SGYWN                                                                      5

SEQ ID NO: 172            moltype = AA   length = 16
FEATURE                   Location/Qualifiers
source                    1..16
                          mol_type = protein
                          organism = synthetic construct
SEQUENCE: 172
YISYSGSTYY NPSLKS                                                         16

SEQ ID NO: 173            moltype = AA   length = 11
FEATURE                   Location/Qualifiers
source                    1..11
                          mol_type = protein
                          organism = synthetic construct
SEQUENCE: 173
IYYDYDGYFD V                                                              11

SEQ ID NO: 174            moltype = AA   length = 16
FEATURE                   Location/Qualifiers
source                    1..16
                          mol_type = protein
                          organism = synthetic construct
SEQUENCE: 174
RSSKSLLHSN GNTFLY                                                         16

SEQ ID NO: 175            moltype = AA   length = 7
FEATURE                   Location/Qualifiers
source                    1..7
                          mol_type = protein
                          organism = synthetic construct
SEQUENCE: 175
RMSNLAS                                                                    7

SEQ ID NO: 176            moltype = AA   length = 9
FEATURE                   Location/Qualifiers
source                    1..9
                          mol_type = protein
                          organism = synthetic construct
SEQUENCE: 176
MQHLEYPYT                                                                  9

SEQ ID NO: 177            moltype = AA   length = 5
FEATURE                   Location/Qualifiers
source                    1..5
                          mol_type = protein
                          organism = synthetic construct
SEQUENCE: 177
SFHIH                                                                      5

SEQ ID NO: 178            moltype = AA   length = 17
FEATURE                   Location/Qualifiers
source                    1..17
                          mol_type = protein
                          organism = synthetic construct
SEQUENCE: 178
WIYPGNDNTD HNEKFKG                                                        17

SEQ ID NO: 179            moltype = AA   length = 10
FEATURE                   Location/Qualifiers
source                    1..10
                          mol_type = protein
                          organism = synthetic construct
SEQUENCE: 179
SNYYGPLFAY                                                                10

SEQ ID NO: 180            moltype = AA   length = 16
FEATURE                   Location/Qualifiers
source                    1..16
                          mol_type = protein
                          organism = synthetic construct
SEQUENCE: 180
```

-continued

RSSQNIVRSN GNTYLE                                                              16

SEQ ID NO: 181        moltype = AA   length = 7
FEATURE               Location/Qualifiers
source                1..7
                      mol_type = protein
                      organism = synthetic construct SEQUENCE: 181
RVSNRFS                                                                         7

SEQ ID NO: 182        moltype = AA   length = 9
FEATURE               Location/Qualifiers
source                1..9
                      mol_type = protein
                      organism = synthetic construct SEQUENCE: 182
FQGSYVPYT                                                                       9

SEQ ID NO: 183        moltype = AA   length = 5
FEATURE               Location/Qualifiers
source                1..5
                      mol_type = protein
                      organism = synthetic construct SEQUENCE: 183
TYAMN                                                                           5

SEQ ID NO: 184        moltype = AA   length = 19
FEATURE               Location/Qualifiers
source                1..19
                      mol_type = protein
                      organism = synthetic construct SEQUENCE: 184
RIRSKYNSYA TYYADSVKD                                                           19

SEQ ID NO: 185        moltype = AA   length = 10
FEATURE               Location/Qualifiers
source                1..10
                      mol_type = protein
                      organism = synthetic construct SEQUENCE: 185
HEDYDGGFAY                                                                     10

SEQ ID NO: 186        moltype = AA   length = 17
FEATURE               Location/Qualifiers
source                1..17
                      mol_type = protein
                      organism = synthetic construct SEQUENCE: 186
KSSQSLFKSR TRKNYLA                                                             17

SEQ ID NO: 187        moltype = AA   length = 7
FEATURE               Location/Qualifiers
source                1..7
                      mol_type = protein
                      organism = synthetic construct SEQUENCE: 187
WASTRES                                                                         7

SEQ ID NO: 188        moltype = AA   length = 9
FEATURE               Location/Qualifiers
source                1..9
                      mol_type = protein
                      organism = synthetic construct SEQUENCE: 188
KESYNLMYT                                                                       9

SEQ ID NO: 189        moltype = AA   length = 5
FEATURE               Location/Qualifiers
source                1..5
                      mol_type = protein
                      organism = synthetic construct SEQUENCE: 189
DYGMA                                                                           5

SEQ ID NO: 190        moltype = AA   length = 17
FEATURE               Location/Qualifiers
source                1..17
                      mol_type = protein
                      organism = synthetic construct

```
SEQUENCE: 190
FISNLAYNIY YADTVTG                                                           17

SEQ ID NO: 191         moltype = AA  length = 15
FEATURE                Location/Qualifiers
source                 1..15
                       mol_type = protein
                       organism = synthetic construct
SEQUENCE: 191
EGGITTVPAT DYFDY                                                             15

SEQ ID NO: 192         moltype = AA  length = 11
FEATURE                Location/Qualifiers
source                 1..11
                       mol_type = protein
                       organism = synthetic construct
SEQUENCE: 192
RASQDIRNYL N                                                                 11

SEQ ID NO: 193         moltype = AA  length = 7
FEATURE                Location/Qualifiers
source                 1..7
                       mol_type = protein
                       organism = synthetic construct
SEQUENCE: 193
YTSRLHS                                                                      7

SEQ ID NO: 194         moltype = AA  length = 9
FEATURE                Location/Qualifiers
source                 1..9
                       mol_type = protein
                       organism = synthetic construct
SEQUENCE: 194
QQVNALPLT                                                                    9

SEQ ID NO: 195         moltype = AA  length = 5
FEATURE                Location/Qualifiers
source                 1..5
                       mol_type = protein
                       organism = synthetic construct
SEQUENCE: 195
EFTIH                                                                        5

SEQ ID NO: 196         moltype = AA  length = 17
FEATURE                Location/Qualifiers
source                 1..17
                       mol_type = protein
                       organism = synthetic construct
SEQUENCE: 196
GINPNTGGTS YNQNFTG                                                           17

SEQ ID NO: 197         moltype = AA  length = 10
FEATURE                Location/Qualifiers
source                 1..10
                       mol_type = protein
                       organism = synthetic construct
SEQUENCE: 197
NWDGYWFFDV                                                                   10

SEQ ID NO: 198         moltype = AA  length = 11
FEATURE                Location/Qualifiers
source                 1..11
                       mol_type = protein
                       organism = synthetic construct
SEQUENCE: 198
RASGNIQNYL A                                                                 11

SEQ ID NO: 199         moltype = AA  length = 7
FEATURE                Location/Qualifiers
source                 1..7
                       mol_type = protein
                       organism = synthetic construct
SEQUENCE: 199
GAKTLAD                                                                      7

SEQ ID NO: 200         moltype = AA  length = 9
FEATURE                Location/Qualifiers
source                 1..9
                       mol_type = protein
```

```
SEQUENCE: 200
QHFWSPPLT                                                               9

SEQ ID NO: 201          moltype = AA   length = 5
FEATURE                 Location/Qualifiers
source                  1..5
                        mol_type = protein
                        organism = synthetic construct
SEQUENCE: 201
KYLIE                                                                   5

SEQ ID NO: 202          moltype = AA   length = 17
FEATURE                 Location/Qualifiers
source                  1..17
                        mol_type = protein
                        organism = synthetic construct
SEQUENCE: 202
VINPGNAGNN YNEKFKG                                                     17

SEQ ID NO: 203          moltype = AA   length = 9
FEATURE                 Location/Qualifiers
source                  1..9
                        mol_type = protein
                        organism = synthetic construct
SEQUENCE: 203
RGRDYAMDN                                                               9

SEQ ID NO: 204          moltype = AA   length = 10
FEATURE                 Location/Qualifiers
source                  1..10
                        mol_type = protein
                        organism = synthetic construct
SEQUENCE: 204
RASSSINYIY                                                             10

SEQ ID NO: 205          moltype = AA   length = 7
FEATURE                 Location/Qualifiers
source                  1..7
                        mol_type = protein
                        organism = synthetic construct
SEQUENCE: 205
YTSNLAP                                                                 7

SEQ ID NO: 206          moltype = AA   length = 9
FEATURE                 Location/Qualifiers
source                  1..9
                        mol_type = protein
                        organism = synthetic construct
SEQUENCE: 206
QQFTSSPLT                                                               9

SEQ ID NO: 207          moltype = AA   length = 7
FEATURE                 Location/Qualifiers
source                  1..7
                        mol_type = protein
                        organism = synthetic construct
SEQUENCE: 207
TSGMGVS                                                                 7

SEQ ID NO: 208          moltype = AA   length = 16
FEATURE                 Location/Qualifiers
source                  1..16
                        mol_type = protein
                        organism = synthetic construct
SEQUENCE: 208
HIFWDDDKRY NPSLKS                                                      16

SEQ ID NO: 209          moltype = AA   length = 11
FEATURE                 Location/Qualifiers
source                  1..11
                        mol_type = protein
                        organism = synthetic construct
SEQUENCE: 209
RARHNYPWFP Y                                                           11

SEQ ID NO: 210          moltype = AA   length = 15
FEATURE                 Location/Qualifiers
source                  1..15
```

```
                            mol_type = protein
                            organism = synthetic construct
SEQUENCE: 210
KASQSVDYDG DSYMN                                                       15

SEQ ID NO: 211              moltype = AA   length = 7
FEATURE                     Location/Qualifiers
source                      1..7
                            mol_type = protein
                            organism = synthetic construct
SEQUENCE: 211
AASNLES                                                                 7

SEQ ID NO: 212              moltype = AA   length = 9
FEATURE                     Location/Qualifiers
source                      1..9
                            mol_type = protein
                            organism = synthetic construct
SEQUENCE: 212
QQSNEGPYT                                                               9

SEQ ID NO: 213              moltype = AA   length = 5
FEATURE                     Location/Qualifiers
source                      1..5
                            mol_type = protein
                            organism = synthetic construct
SEQUENCE: 213
SYWIH                                                                   5

SEQ ID NO: 214              moltype = AA   length = 17
FEATURE                     Location/Qualifiers
source                      1..17
                            mol_type = protein
                            organism = synthetic construct
SEQUENCE: 214
TIYPGDGDTR STQKFKD                                                     17

SEQ ID NO: 215              moltype = AA   length = 14
FEATURE                     Location/Qualifiers
source                      1..14
                            mol_type = protein
                            organism = synthetic construct
SEQUENCE: 215
SLIHDDYDKY YFDY                                                        14

SEQ ID NO: 216              moltype = AA   length = 11
FEATURE                     Location/Qualifiers
source                      1..11
                            mol_type = protein
                            organism = synthetic construct
SEQUENCE: 216
KARQDINKYI A                                                           11

SEQ ID NO: 217              moltype = AA   length = 7
FEATURE                     Location/Qualifiers
source                      1..7
                            mol_type = protein
                            organism = synthetic construct
SEQUENCE: 217
YTSILQP                                                                 7

SEQ ID NO: 218              moltype = AA   length = 8
FEATURE                     Location/Qualifiers
source                      1..8
                            mol_type = protein
                            organism = synthetic construct
SEQUENCE: 218
LQYDYFFT                                                                8

SEQ ID NO: 219              moltype = AA   length = 7
FEATURE                     Location/Qualifiers
source                      1..7
                            mol_type = protein
                            organism = synthetic construct
SEQUENCE: 219
TSGMGVS                                                                 7

SEQ ID NO: 220              moltype = AA   length = 16
FEATURE                     Location/Qualifiers
```

```
source                  1..16
                        mol_type = protein
                        organism = synthetic construct
SEQUENCE: 220
HIFWDDDKRY NPSLKS                                                        16

SEQ ID NO: 221          moltype = AA   length = 11
FEATURE                 Location/Qualifiers
source                  1..11
                        mol_type = protein
                        organism = synthetic construct
SEQUENCE: 221
RARNNYPWFP Y                                                             11

SEQ ID NO: 222          moltype = AA   length = 15
FEATURE                 Location/Qualifiers
source                  1..15
                        mol_type = protein
                        organism = synthetic construct
SEQUENCE: 222
KASQSVDYDG DSYMN                                                         15

SEQ ID NO: 223          moltype = AA   length = 7
FEATURE                 Location/Qualifiers
source                  1..7
                        mol_type = protein
                        organism = synthetic construct
SEQUENCE: 223
AASNLDS                                                                  7

SEQ ID NO: 224          moltype = AA   length = 9
FEATURE                 Location/Qualifiers
source                  1..9
                        mol_type = protein
                        organism = synthetic construct
SEQUENCE: 224
QQSNGAPFT                                                                9

SEQ ID NO: 225          moltype = AA   length = 113
FEATURE                 Location/Qualifiers
source                  1..113
                        mol_type = protein
                        organism = synthetic construct
SEQUENCE: 225
QVQLVESGGG VVQPGRSLRL SCAVSGFSLT TYGIHWVRQA PGKGLEWLAV IWTGGTTDYN         60
AAFISRFTIS KDNSKSTLYL QMNSLRAEDT AVYYCARGPS SYWGQGTLVT VSS                113

SEQ ID NO: 226          moltype = AA   length = 113
FEATURE                 Location/Qualifiers
source                  1..113
                        mol_type = protein
                        organism = synthetic construct
SEQUENCE: 226
QVQLVESGGG VVQPGRSLRL SCTVSGFSLT TYGIHWVRQS PGKGLEWLGV IWTGGTTDYN         60
AAFISRLTIS KDNSKSTLYF QMNSLRAEDT AVYYCARGPS SYWGQGTLVT VSS                113

SEQ ID NO: 227          moltype = AA   length = 113
FEATURE                 Location/Qualifiers
source                  1..113
                        mol_type = protein
                        organism = synthetic construct
SEQUENCE: 227
QVQLVQSGGG VVQPGRSLRL SCTVSGFSLT TYGIHWVRQS PGKGLEWLGV IWTGGTTDYN         60
AAFISRLTIS KDNSKSTVYF QMNSLQAEDT AIYYCARGPS SYWGQGTLVT VSS                113

SEQ ID NO: 228          moltype = AA   length = 113
FEATURE                 Location/Qualifiers
source                  1..113
                        mol_type = protein
                        organism = synthetic construct
SEQUENCE: 228
QVQLQESGPG LVKPSGTLSL TCAVSGFSLT TYGIHWVRQS PGKGLEWLGV IWTGGTTDYN         60
AAFISRLTIS KDKSKNQVSL KLSSVTAADT AVYYCARGPS SYWGQGTLVT VSS                113

SEQ ID NO: 229          moltype = AA   length = 113
FEATURE                 Location/Qualifiers
source                  1..113
                        mol_type = protein
                        organism = synthetic construct
```

```
SEQUENCE: 229
QVQLQQSGPG LVKPSGTLSL TCTVSGFSLT TYGIHWVRQS PGKGLEWLGV IWTGGTTDYN    60
AAFISRLTIS KDKSKNQVFF KMSSLTAADT AVYYCARGPS SYWGQGTLVT VSS          113

SEQ ID NO: 230          moltype = AA   length = 107
FEATURE                 Location/Qualifiers
source                  1..107
                        mol_type = protein
                        organism = synthetic construct
SEQUENCE: 230
EIVMTQSPAT LSVSPGERAT LSCKASQNVD TNVVWYQQKP GQSPRALIYS ASYRYSGVPA    60
RFSGSGSGTE FTLTISSLQS EDFAVYFCQQ YNNYPWTFGQ GTKVEIK                 107

SEQ ID NO: 231          moltype = AA   length = 107
FEATURE                 Location/Qualifiers
source                  1..107
                        mol_type = protein
                        organism = synthetic construct
SEQUENCE: 231
EIVMTQSPAT LSVSPGERAT VSCKASQNVD TNVVWYQQKP GQSPRALIHS ASYRYSGVPD    60
RFSGSGSGTD FTLTISSLQS EDFAVYFCQQ YNNYPWTFGQ GTKVEIK                 107

SEQ ID NO: 232          moltype = AA   length = 107
FEATURE                 Location/Qualifiers
source                  1..107
                        mol_type = protein
                        organism = synthetic construct
SEQUENCE: 232
DIVMTQSPAT LSVSPGERVT VSCKASQNVD TNVVWYQQKP GQSPRALIHS ASYRYSGVPD    60
RFSGSGSGTD FTLTISSVQS EDFAVYFCQQ YNNYPWTFGG GTKLEIK                 107

SEQ ID NO: 233          moltype = AA   length = 17
FEATURE                 Location/Qualifiers
source                  1..17
                        mol_type = protein
                        organism = synthetic construct
SEQUENCE: 233
WIDPENDDTE YDPKFQG                                                   17

SEQ ID NO: 234          moltype = AA   length = 16
FEATURE                 Location/Qualifiers
source                  1..16
                        mol_type = protein
                        organism = synthetic construct
SEQUENCE: 234
RSSQSIVHSN ANTYLE                                                    16

SEQ ID NO: 235          moltype = AA   length = 116
FEATURE                 Location/Qualifiers
source                  1..116
                        mol_type = protein
                        organism = synthetic construct
SEQUENCE: 235
QVQLVQSGAE VVKPGASVKV SCKASGFNIK DYYMHWVRQA PGQGLEWIGW IDPENDDTEY    60
DPKFQGRVTM TADTSTSTVY MELSSLRSED TAVYYCAARY YAFDYWGQGT MVTVSS       116

SEQ ID NO: 236          moltype = AA   length = 116
FEATURE                 Location/Qualifiers
source                  1..116
                        mol_type = protein
                        organism = synthetic construct
SEQUENCE: 236
QVPLVQSGAE VVKPGASVKV SCKASGFNIK DYYMHWVRQA PGQGLEWIGW IDPENDDTEY    60
DPKFQGRATM TADTSTSTAY MELSSLRSED TAVYYCNARY YAFDYWGQGT TVTVSS       116

SEQ ID NO: 237          moltype = AA   length = 116
FEATURE                 Location/Qualifiers
source                  1..116
                        mol_type = protein
                        organism = synthetic construct
SEQUENCE: 237
QVPLVQSGAE VVKPGASVKL SCKASGFNIK DYYMHWVKQA PGQGLEWIGW IDPENDDTEY    60
DPKFQGRATM TADTSTSTAY LELSSLRSED TAVYYCNARY YAFDYWGQGT TVTVSS       116

SEQ ID NO: 238          moltype = AA   length = 112
FEATURE                 Location/Qualifiers
source                  1..112
                        mol_type = protein
                        organism = synthetic construct
```

```
SEQUENCE: 238
DVLMTQSPLS LPVTLGQPAS ISCRSSQSIV HSNANTYLEW YLQRPGQSPR LLIYKVSNRF    60
SGVPDRFSGS GSGTDFTLKI SRVEAEDVGV YYCFQGSQVP PTFGQGTKLE IK           112

SEQ ID NO: 239           moltype = AA  length = 112
FEATURE                  Location/Qualifiers
source                   1..112
                         mol_type = protein
                         organism = synthetic construct
SEQUENCE: 239
DVLMTQSPLS LPVTLGQPAS ISCRSSQSIV HSNANTYLEW YLQRPGQSPK LLIYKVSNRF    60
SGVPDRFSGS GSGTEFTLKI SRVEAEDLGV YYCFQGSQVP PTFGGGTKLE IK           112

SEQ ID NO: 240           moltype = AA  length = 112
FEATURE                  Location/Qualifiers
source                   1..112
                         mol_type = protein
                         organism = synthetic construct
SEQUENCE: 240
DVQMTQSPSS LSASVGDRVT ITCRSSQSIV HSNANTYLEW YLQKPGKSPK LLIYKVSNRF    60
SGVPDRFSGS GSGTDFTLTI SSLQPEDFAT YYCFQGSQVP PTFGQGTRLE IK           112

SEQ ID NO: 241           moltype = AA  length = 112
FEATURE                  Location/Qualifiers
source                   1..112
                         mol_type = protein
                         organism = synthetic construct
SEQUENCE: 241
DVLMTQSPSS LSASVGDRVT ITCRSSQSIV HSNANTYLEW YLQKPGKSPK LLIYKVSNRF    60
SGVPDRFSGS GSGTEFTLTI SSVQPEDFAV YYCFQGSQVP PTFGQGTRLE IK           112

SEQ ID NO: 242           moltype = AA  length = 112
FEATURE                  Location/Qualifiers
source                   1..112
                         mol_type = protein
                         organism = synthetic construct
SEQUENCE: 242
DVLMTQSPSS LSVSVGDRAT ISCRSSQSIV HSNANTYLEW YLQKPGKSPK LLIYKVSNRF    60
SGVPDRFSGS GSGTEFTLTI SSVQPEDFGV YYCFQGSQVP PTFGGGTRLE IK           112

SEQ ID NO: 243           moltype = AA  length = 17
FEATURE                  Location/Qualifiers
source                   1..17
                         mol_type = protein
                         organism = synthetic construct
SEQUENCE: 243
TIYPGDADTR STQKFKD                                                    17

SEQ ID NO: 244           moltype = AA  length = 123
FEATURE                  Location/Qualifiers
source                   1..123
                         mol_type = protein
                         organism = synthetic construct
SEQUENCE: 244
EVQLVQSGAE VKKPGASVKV SCKASGYTFT SYWIHWVRQA PGQGLEWMGT IYPGDADTRS    60
TQKFKDRVTM TADTSTSTVY MELSSLRSED TAVYYCARSL IHDDYDKYYF DYWGQGTTVT   120
VSS                                                                  123

SEQ ID NO: 245           moltype = AA  length = 123
FEATURE                  Location/Qualifiers
source                   1..123
                         mol_type = protein
                         organism = synthetic construct
SEQUENCE: 245
EVQLVQSGAE VKKPGASVKV SCKASGYTFT SYWIHWVRQA PGQGLEWMGT IYPGDADTRS    60
TQKFKDRVTV TADKSTSTVY MELSSLRSED TAVYYCARSL IHDDYDKYYF DYWGQGTTVT   120
VSS                                                                  123

SEQ ID NO: 246           moltype = AA  length = 123
FEATURE                  Location/Qualifiers
source                   1..123
                         mol_type = protein
                         organism = synthetic construct
SEQUENCE: 246
EVQLVQSGAE VKKPGASVKV SCKASGYTFT SYWIHWVRQA PGQGLEWIGT IYPGDADTRS    60
TQKFKDKATV TADKSTSTVY MELSSLRSED TAVYYCARSL IHDDYDKYYF DYWGQGTTVT   120
VSS                                                                  123

SEQ ID NO: 247           moltype = AA  length = 123
```

```
FEATURE                 Location/Qualifiers
source                  1..123
                        mol_type = protein
                        organism = synthetic construct
SEQUENCE: 247
EVQLVQSGAE VKKPGASVKV SCKASGYTFT SYWIHWVRQA PGQGLEWMGT IYPGDADTRS    60
TQKFKDRVTV TADKSTSTVY MELSSLRSED TAVYYCTRSL IHDDYDKYYF DYWGQGTTVT   120
VSS                                                                 123

SEQ ID NO: 248          moltype = AA  length = 123
FEATURE                 Location/Qualifiers
source                  1..123
                        mol_type = protein
                        organism = synthetic construct
SEQUENCE: 248
EVQLVQSGAE VKKPGASVKV SCKASGYTFT SYWIHWVRQA PGQGLEWIGT IYPGDADTRS    60
TQKFKDKATV TADKSTSTVY MELSSLRSED TAVYYCTRSL IHDDYDKYYF DYWGQGTTVT   120
VSS                                                                 123

SEQ ID NO: 249          moltype = AA  length = 123
FEATURE                 Location/Qualifiers
source                  1..123
                        mol_type = protein
                        organism = synthetic construct
SEQUENCE: 249
EIQLVQSGAE VKKPGASVKV SCKASGYTFT SYWIHWVREA PGQGLEWIGT IYPGDADTRS    60
TQKFKDKATV TADKSTSTVY MELSSLRSED TAVYYCTRSL IHDDYDKYYF DYWGQGTTVT   120
VSS                                                                 123

SEQ ID NO: 250          moltype = AA  length = 106
FEATURE                 Location/Qualifiers
source                  1..106
                        mol_type = protein
                        organism = synthetic construct
SEQUENCE: 250
DIQMTQSPSS LSASVGDRVT ITCKARQDIN KYIAWYQQKP GKAPKLLIYY TSILQPGVPS    60
RFSGSGSGRD YTFTISSLQP EDIATYYCLQ YDYFFTFGGG TKVEIK                  106

SEQ ID NO: 251          moltype = AA  length = 106
FEATURE                 Location/Qualifiers
source                  1..106
                        mol_type = protein
                        organism = synthetic construct
SEQUENCE: 251
DIQMTQSPSS LSASVGDRVT ITCKARQDIN KYIAWYQQKP GKAPKLLIHY TSILQPGIPS    60
RFSGSGSGRD YTFTISSLQP EDIATYYCLQ YDYFFTFGGG TKVEIK                  106

SEQ ID NO: 252          moltype = AA  length = 106
FEATURE                 Location/Qualifiers
source                  1..106
                        mol_type = protein
                        organism = synthetic construct
SEQUENCE: 252
DIQMTQSPSS LSASVGDRVT ITCKARQDIN KYIAWYQHKP GKGPKLLIHY TSILQPGIPS    60
RFSGSGSGRD YTFTISSLQP EDIATYYCLQ YDYFFTFGGG TKVEIK                  106
```